United States Patent
Donahoe et al.

(10) Patent No.: US 9,289,492 B2
(45) Date of Patent: Mar. 22, 2016

(54) COLLECTING OVARIAN CANCER STEM CELLS FROM OVARIAN CANCER CELLS

(75) Inventors: Patricia K Donahoe, Boston, MA (US); Paul P Szotek, Indianapolis, IN (US); David T MacLaughlin, Glouchester, MA (US); Frederic Preffer, Cambridge, MA (US); Rafael Pieretti-Vanmarcke, Boston, MA (US); David Michael Dombkowski, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 268 days.

(21) Appl. No.: 12/669,136

(22) PCT Filed: Jul. 17, 2008

(86) PCT No.: PCT/US2008/070273
§ 371 (c)(1),
(2), (4) Date: Jul. 7, 2010

(87) PCT Pub. No.: WO2009/012357
PCT Pub. Date: Jan. 22, 2009

(65) Prior Publication Data
US 2010/0273160 A1    Oct. 28, 2010

Related U.S. Application Data

(60) Provisional application No. 60/959,866, filed on Jul. 17, 2007.

(51) Int. Cl.
| | |
|---|---|
| C12N 5/00 | (2006.01) |
| A61K 45/06 | (2006.01) |
| A61K 31/00 | (2006.01) |
| A61K 31/277 | (2006.01) |
| A61K 31/7088 | (2006.01) |
| C12N 5/095 | (2010.01) |
| G01N 33/50 | (2006.01) |
| G01N 33/574 | (2006.01) |
| C12N 5/071 | (2010.01) |

(52) U.S. Cl.
CPC ............... *A61K 45/06* (2013.01); *A61K 31/00* (2013.01); *A61K 31/277* (2013.01); *A61K 31/7088* (2013.01); *C12N 5/0695* (2013.01); *G01N 33/5011* (2013.01); *G01N 33/5091* (2013.01); *G01N 33/57449* (2013.01); *C12N 5/0672* (2013.01); *C12N 2501/998* (2013.01); *C12N 2503/00* (2013.01); *C12N 2503/02* (2013.01); *G01N 2800/44* (2013.01); *G01N 2800/54* (2013.01)

(58) Field of Classification Search
CPC . A61K 31/00; A61K 31/277; A61K 31/7088; A61K 45/06; C12N 5/0672
See application file for complete search history.

(56) References Cited

U.S. PATENT DOCUMENTS

| | | | |
|---|---|---|---|
| 7,504,225 B2 | 3/2009 | Ring et al. | |
| 2003/0119080 A1* | 6/2003 | Mangano | 435/7.23 |
| 2004/0037815 A1 | 2/2004 | Clarke et al. | |
| 2007/0026469 A1* | 2/2007 | Fuchs et al. | 435/7.23 |
| 2007/0254319 A1* | 11/2007 | Donnenberg et al. | 435/7.23 |
| 2008/0187938 A1* | 8/2008 | Wicha et al. | 435/7.4 |

OTHER PUBLICATIONS

Li et al (Cancer Res, 67: 1030-1037. Published online Feb. 5, 2007).*
Teixeira et al (Endocrine reviews, 22(5): 667-674, 2001).*
Yan et al. (2000, Science 290:523-527).*
Heinzelmann-Schwarz et al (Clinical Cancer Research, 10: 4427-4436, 2004).*
Patrawala, et al (Cancer Res, 65 (14): 6207-6.*
Doyle et al (Oncogene, 22: 7340-7358, 2003);.*
Kondo et al (PNAS, 101(3): 781-786, 2004).*
Mao et al (The AAPS Journal; 7 (1): E118-E133, 2005).).*
Hirschmann-Jax et al (PNAS, 101: pp. 14228-14233, 2004).*
Szotek, P. P. et al., "Ovarian cancer side population defines cells with stem cell-like characteristics and Mullerian Inhibiting Substance responsiveness." PNAS 103(3):11154-11159, 2006.
Arango et al., Developmental Biology, 288:276-283 (2005). "Conditional deletion of beta-catenin in the mesenchyme of the developing mouse uterus in a switch to adipogenesis in the myometrium."
Auersperg et al., Proc. Natl. Acad. Sci., 96:6249-6254 (1999). "E-cadherin induces mesenchymal-to-epithelial transition in human ovarian surface epithelium."
Bjersing et al., Cell Tiss. Res., 149:287-300 (1974). "Ovulation and the Mechanism of Follicle Rupture."
Bjersing et al., Experientia, 31:605-608 (1975). "Ovulation and the role of the ovarian surface epithelium."
Cannistra et al., J Clin Oncol., 21(10 Suppl):129s-132s (2003). "Progress in the management of gynecologic cancer: consensus summary statement."
Cannistra, The New England Journal of Medicine, 351:2519-2529 (2004). "Cancer of the Ovary."
Cheng et al., Nature Medicine, 11(5):531-537 (2005). "Lineage infidelity of epithelial ovarian cancers is controlled by HOX genes that specify regional identity in the reproductive tract."

(Continued)

*Primary Examiner* — Deborah Crouch
*Assistant Examiner* — Magdalene Sgagias
(74) *Attorney, Agent, or Firm* — Nixon Peabody LLP

(57) ABSTRACT

The present invention relates to compositions and methods for treating, characterizing and diagnosing ovarian cancer. In particular, the present invention provides methods for treating and/or preventing ovarian cancer in a subject by administering to the subject an effective amount of Mullerian Inhibiting substance and/or an effective amount of an agent that inhibits BCRP1. The present invention further provides methods to identify and/or enrich for populations of ovarian cancer stem cells and populations of somatic ovarian stem cells, in particular, enrichment for populations of coelomic somatic ovarian stem cells, subcoelomic/stromal somatic ovarian stem cells and periphilar medullary somatic ovarian stem cells. The present invention also provides somatic ovarian stem cell markers and ovarian cancer stem cell markers, as well as methods to identify agents which selectively inhibit the proliferation of ovarian cancer stem cells as compared to somatic ovarian stem cells.

11 Claims, 38 Drawing Sheets

(56) References Cited

OTHER PUBLICATIONS

Doyle et al., Oncogene, 22:7340-7358 (2003). "Multidrug resistance mediated by the breast cancer resistance protein BCRP (ABCG2)."
Drapkin et al., Hum Pathol, 35:1014-1021 (2004). "Expression of Candidate Tumor Markers in Ovarian Carcinoma and Benign Ovary: Evidence for a Link Between Epithelial Phenotype and Neoplasia."
Eggan et al., Nature, 441:1109-1114 (2006). "Ovulated oocytes in adult mice derive from non-circulating germ cells."
Gottesman et al., Annu. Rev. Biochem., 62:385-427 (1993). "Biochemistry of Multidrug Resistance Mediated by the Multidrug Transporter."
Gottesman et al., Nature, 2:48-58 (2001). "Multidrug Resistance in Cancer: Role of ATP-Dependent Transporters."
Ha et al., The Journal of Biological Chemistry, 275(47):37101-37109 (2000). "Mullerian Inhibiting Substance Inhibits Ovarian Cell Growth through an Rb-independent Mechanism."
Haraguchi et al., Stem Cells, 24:506-513 (2006). "Characterization of a Side Population of Cancer Cells from Human Gastrointestinal System."
Heinzelmann-Schwarz et al., Clinical Cancer Research, 10:4427-4436 (2004). "Overexpression of the Cell Adhesion Molecules DDR1, Claudin 3, and Ep-CAM in Metaplastic Ovarian Epithelium and Ovarian Cancer."
Hirschmann-Jax et al., PNAS, 101(39):14228-14233 (2004). "A distinct 'side population' of cells with high drug efflux capacity in human tumor cells."
Kim et al., Clinical Cancer Research, 9:4782-4791 (2003). "Identification of Epithelial Cell Adhesion Molecule Autoantibody in Patients with Ovarian Cancer."
Konstantinopoulos et al., PLoS One, 6(3):e18202 (2011). "Integrated Analysis of Multiple Microarray Datasets Identifies a Reproducible Survival Predictor in Ovarian Cancer."
Leedham et al., J. Cell. Mol. Med., 9(1):11-24 (2005). "Intestinal stem cells."
Liu et al., Current Topics in Developmental Biology, 64:33-56 (2004). "Airway Glandular Development and Stem Cells."
Maliepaard et al., Cancer Research, 59:4559-4563 (1999). "Overexpression of the BCRP/MXR/ABCP Gene in a Topotecan-selected Ovarian Tumor Cell Line."
Morris et al., Cell Prolif., 27:279-289 (1994). "Slowly cycling (label-retaining) epidermal cells behave like clonogenic stem cells in vitro."
Morrison et al., Immunity, 1:661-673 (1994). "The Long-Term Repopulating Subset of Hematopoietic Stem Cells Is Deterministic and Isolatable by Phenotype."
Parker et al., CA Cancer J Clin, 47(1):5-27 (1997). "Cancer Statistics, 1997."
Pieretti-Vanmarcke et al., Clin Cancer Res, 12(5):1593-1598 (2006). "Recombinant Human Mullerian Inhibiting Substance Inhibits Long-term Growth of MIS Type II Receptor-Directed Transgenic Mouse Ovarian Cancers In Vivo."
Poste et al., Invasion Metastasis, 2:137-176 (1982). "On the Genesis and Regulation of Cellular Heterogeneity in Malignant Tumors."
Poste et al., Proc. Natl. Acad. Sci., 79:6574-6578 (1982). "Evolution of tumor cell heterogeneity during progressive growth of individual lung metastases."
Scully, Human Pathology, 1(1):73-98 (1970). "Recent Progress in Ovarian Cancer."
Seigel et al., Molecular Vision, 11:729-737 (2005). "Cancer stem cell characteristics in retinoblastoma."
Sell, Critical Reviews in Oncology/Hematology, 51:1-28 (2004). "Stem cell origin of cancer and differentiation therapy."
Siegel et al., CA Cancer J Clin, 63:11-30 (2013). "Cancer Statistics, 2013."
Smalley et al., Journal of Mammary Gland Biology and Neoplasia, 10(1):37-47 (2005). "The Mammary Gland 'Side Population': A Putative Stem-Progenitor Cell Marker?"
Tu et al., the Lancet Oncology, 3:508-513 (2002). "Stem-cell origin of metastasis and heterogeneity in solid tumours."
Wu et al., Methods in Molecular Biology, 289: Epidermal Cells: Methods and Protocols:73-77 (2005). "In Vivo Labeling and Analysis of Epidermal Stem Cells."
Wulf et al., Blood, 98(4):1166-1173 (2001). "A leukemic stem cell with intrinsic drug efflux capacity in acute myeloid leukemia."
Young, Modern Pathology, 18:S3-S17 (2005). "A brief history of the pathology of the gonads."
Donnenberg et al., "Constitutive multiple drug resistance in tumor stem cells." American Association for Cancer Research 46:479 (2005) Abstract Only.
Albert et al., (2001). Murine epidermal label-retaining cells isolated by flow cytometry do not express the stem cell markers CD34, Sca-1, or Flk-1. J Invest Dermatol 117, 943-948.
Al-Hajj et al., (2003). Prospective identification of tumorigenic breast cancer cells. Proc Natl Acad Sci USA 100(7), 3983-3988.
Alvarez-Buylla et al. (2004). For the long run: maintaining germinal niches in the adult brain. Neuron 41, 683-686.
Behbod et al., 2004 Will cancer stem cells provide new therapeutic targets? Carcinogenesis 26, 703-711.
Berns, A. (2005). Stem cells for lung cancer? Cell 121, 811-817.
Bhatt et al., (2003). Novel method for the isolation and characterisation of the putative prostatic stem cell. Cytometry A 54A, 89-99.
Blanpain et al. (2004). Self-renewal, multipotency, and the existence of two cell populations within an epithelial stem cell niche. Cell 118, 635-648.
Braun et al., (2004). Epidermal label-retaining cells: background and recent applications. J Investig Dermatol Symp Proc 9, 196-201.
Bukovsky et al., (2004). Origin of germ cells and formation of new primary follicles in adult human ovaries. Reprod Biol Endocrinol 2, 20.
Clow et al., (2002). Changes in the mouse ovarian surface epithelium with age and ovulation number. Mol Cell Endocrinol 191, 105-111.
Fuchs et al., (2004). Socializing with the neighbors: stem cells and their niche. Cell 116, 769-778.
Goodell et al., (1996). Isolation and functional properties of murine hematopoietic stem cells that are replicating in vivo. J Exp Med 183, 1797-1806.
Haraguchi et al., (2005). Characterization of a Side Population of Cancer Cells from Human Gastrointestinal System. Stem Cells 24, 506-513.
Imitola et al., (2004). Neural stem/progenitor cells express costimulatory molecules that are differentially regulated by inflammatory and apoptotic stimuli. Am J Pathol 164(5), 1615-1625.
Jonker et al., (2005). Contribution of the ABC transporters Bcrp1 and Mdr1a/1b to the side population phenotype in mammary gland and bone marrow of mice. Stem Cells 23, 1059-1065.
Kenney et al., (2001). Identification of Stem Cell Units in the Terminal End Bud and Duct of the Mouse Mammary Gland. J Biomed Biotechnol 1(3), 133-143.
Kondo et al., (2003). Biology of hematopoietic stem cells and progenitors: implications for clinical application. Annu Rev Immunol 21, 759-806.
Li et al., (2005). Stem Cell Niche: Structure and Function. Annu. Rev. Cell Dev. Biol. 21, 605-631.
Lowry et al., (2005). Defining the impact of beta-catenin/Tcf transactivation on epithelial stem cells. Genes Dev 19, 1596-1611.
Mills et al., (2001). The intestinal stem cell niche: there grows the neighborhood. Proc Natl Acad Sci USA 98(22), 12334-12336.
Morris et al., (1986). Evidence that a slowly cycling subpopulation of adult murine epidermal cells retains carcinogen. Cancer Res 46, 3061-3066.
Morris et al., (1999). Highly persistent label-retaining cells in the hair follicles of mice and their fate following induction of anagen. J Invest Dermatol 112, 470-475.
Murdoch et al., (2001). Ovulation-induced DNA damage in ovarian surface epithelial cells of ewes: prospective regulatory mechanisms of repair/survival and apoptosis. Biol Reprod 65, 1417-1424.
Oliver et al., (2004). The renal papilla is a niche for adult kidney stem cells. J Clin Invest 114(6), 795-804.

(56) References Cited

OTHER PUBLICATIONS

Patrawala et al., (2005). Side Population is Enriched in Tumorigenic, Stem-Like Cancer Cells, whereas ABCG2+ and ABCG2− Cancer Cells Are Similarly Tumorigenic. Cancer Res 65(14), 6207-6219.

Preffer et al., (2002). Lineage-negative side-population (SP) cells with restricted hematopoietic capacity circulate in normal human adult blood: immunophenotypic and functional characterization. Stem Cells 20, 417-427.

Reya et al., (2001). Stem cells, cancer, and cancer stem cells. Nature 414, 105-111.

Smalley et al., (2005). An improved definition of mouse mammary epithelial side population cells. Cytotherapy 7(6), 497-508.

Spradling et al., (2001). Stem cells find their niche. Nature 414, 98-104.

Szotek et al., (2006). Ovarian cancer side population defines cells with stem cell-like characteristics and Mullerian Inhibiting Substance responsiveness. Proc Natl Acad Sci USA 103(30), 11154-11159.

Szotek et al., (2007). Adult Mouse Myometrial Label-Retaining Cells Divide in Response to Gonadotropin Stimulation. Stem Cells 25, 1317-1325.

Tan et al., (2004). Proliferating cell nuclear antigen immunoreactivity in the ovarian surface epithelium of mice of varying ages and total lifetime ovulation No. following ovulation. Biol Reprod 71, 1501-1507.

Tsujimura et al., (2002). Proximal location of mouse prostate epithelial stem cells: a model of prostatic homeostasis. J Cell Biol 157(7), 1257-1265.

Tumbar et al., (2004). Defining the epithelial stem cell niche in skin. Science 303, 359-363.

Vidrich et al., (2003). Intestinal stem cells and mucosal gut development. Curr Opin Gastroenterol 19, 583-590.

Watt et al., (2000). Out of Eden: stem cells and their niches. Science 287, 1427-1430.

Welm et al., (2002). Sca-1(pos) cells in the mouse mammary gland represent an enriched progenitor cell population. Dev Biol 245, 42-56.

Welm et al., (2003). Isolation and characterization of functional mammary gland stem cells. Cell Prolif 36 Suppl 1, 17-32.

Williams et al., (1992). A stem cell niche theory of intestinal crypt maintenance based on a study of somatic mutation in colonic mucosa. Am J Pathol 141(4), 773-776.

Wong, M.H., (2004). Regulation of intestinal stem cells. J Investig Dermatol Symp Proc 9, 224-228.

Wulf et al., (2001). A leukemic stem cell with intrinsic drug efflux capacity in acute myeloid leukemia. Blood 98(4), 1166-1173.

Zhan et al., (2006). Mullerian inhibiting substance regulates its receptor/SMAD signaling and causes mesenchymal transition of the coelomic epithelial cells early in Mullerian duct regression. Development 133, 2359-2369.

\* cited by examiner

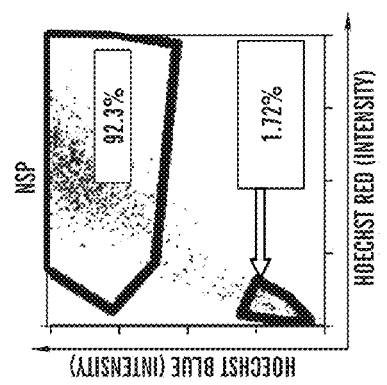
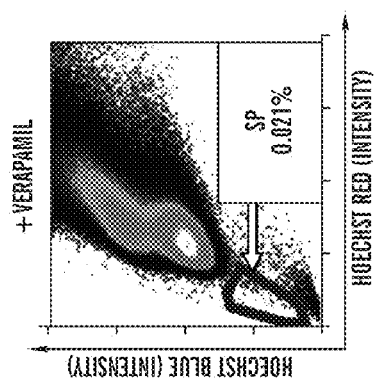
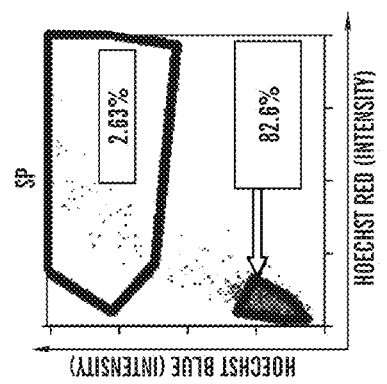
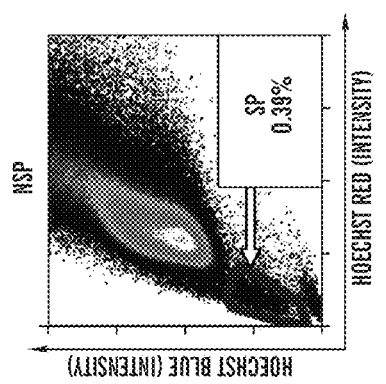
FIG. 4C
FIG. 4D
FIG. 4E
FIG. 4F

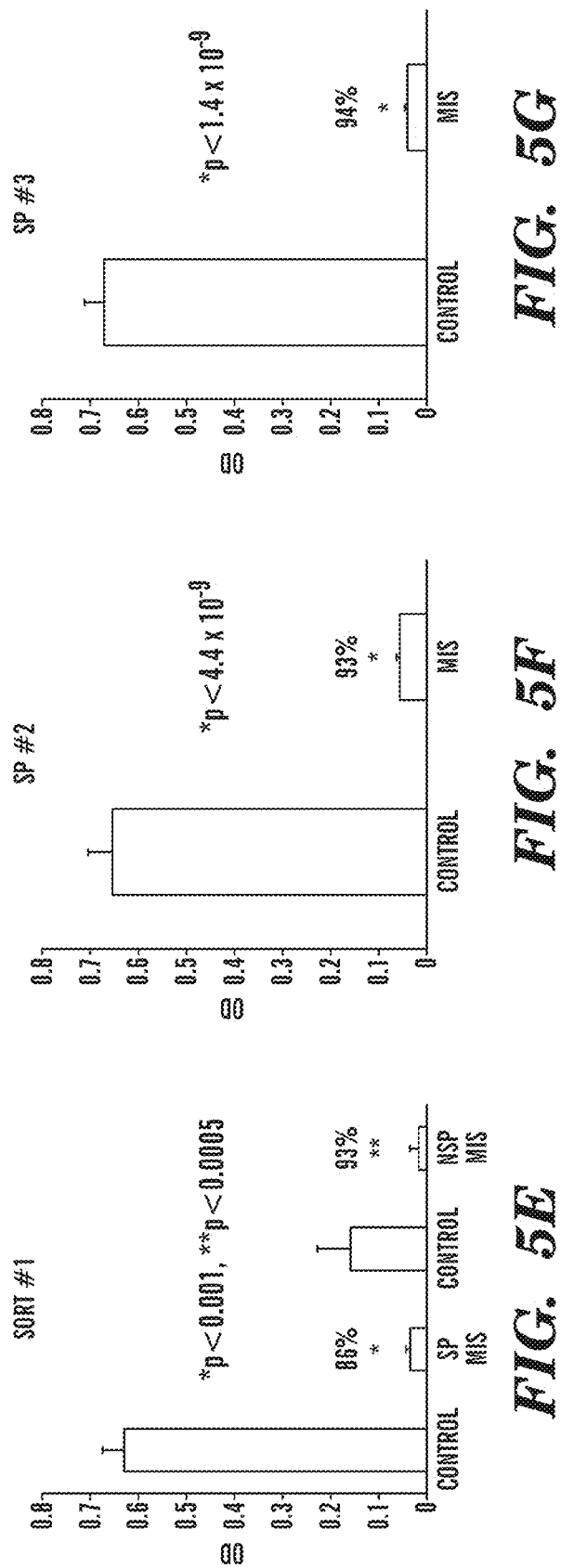

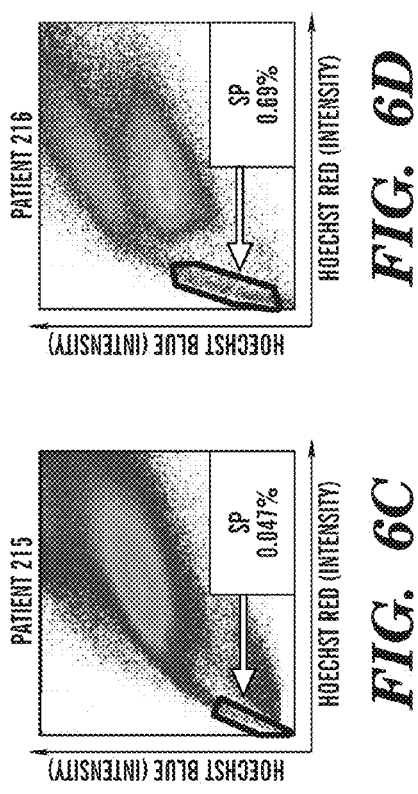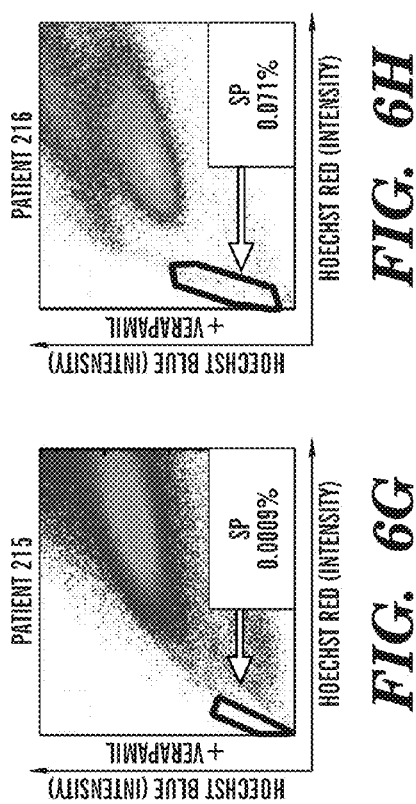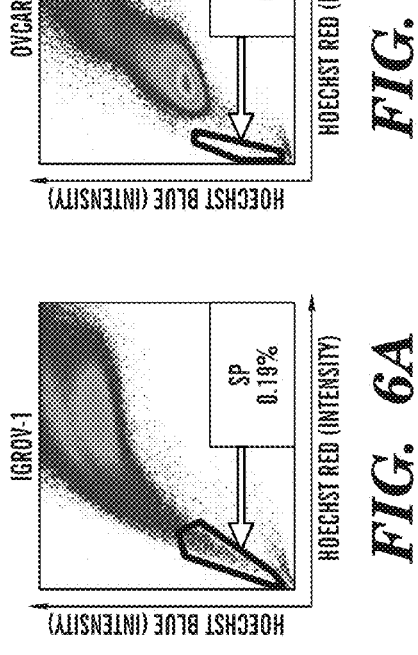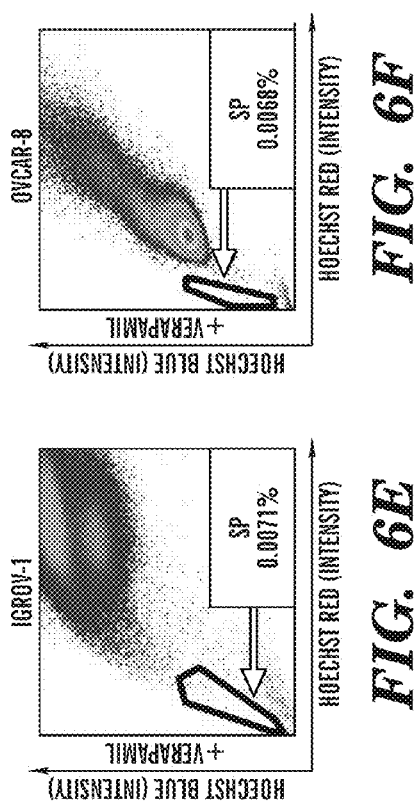

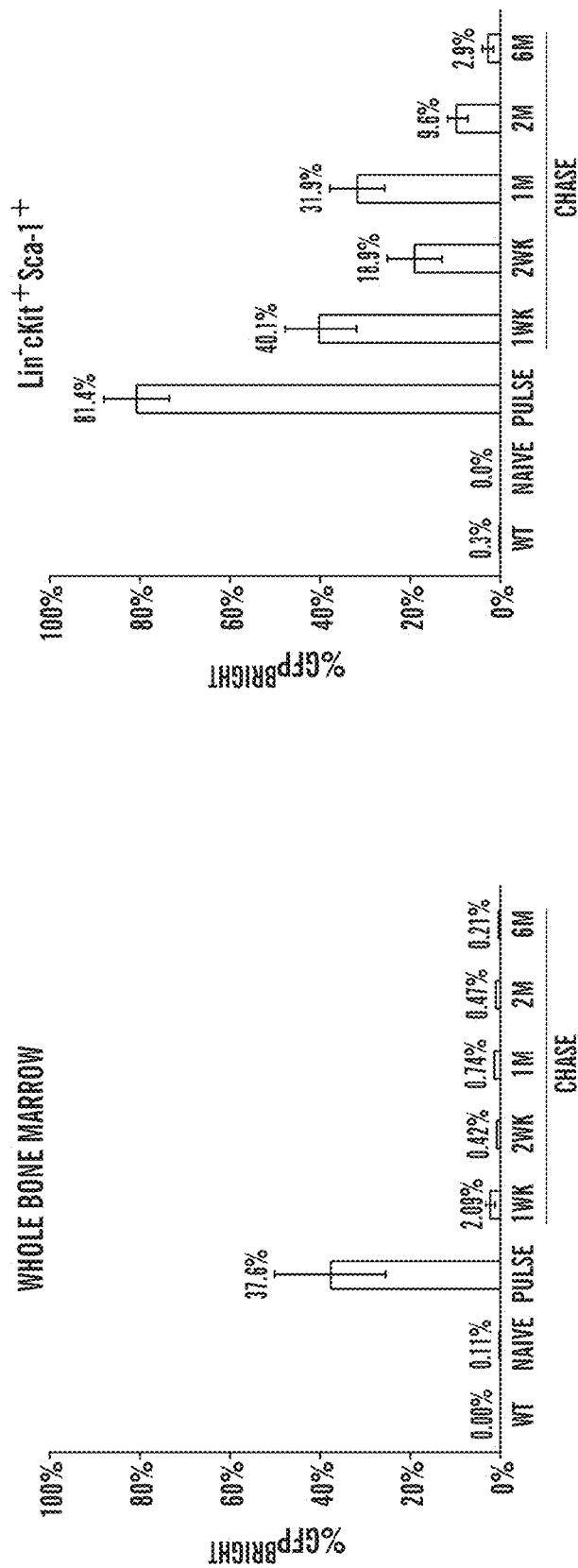

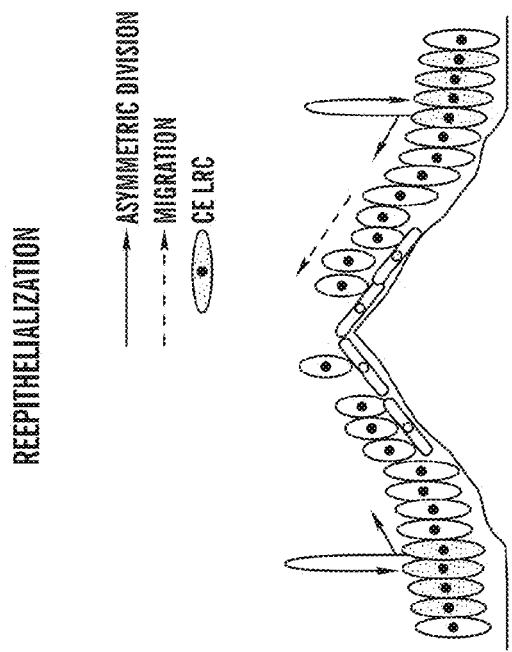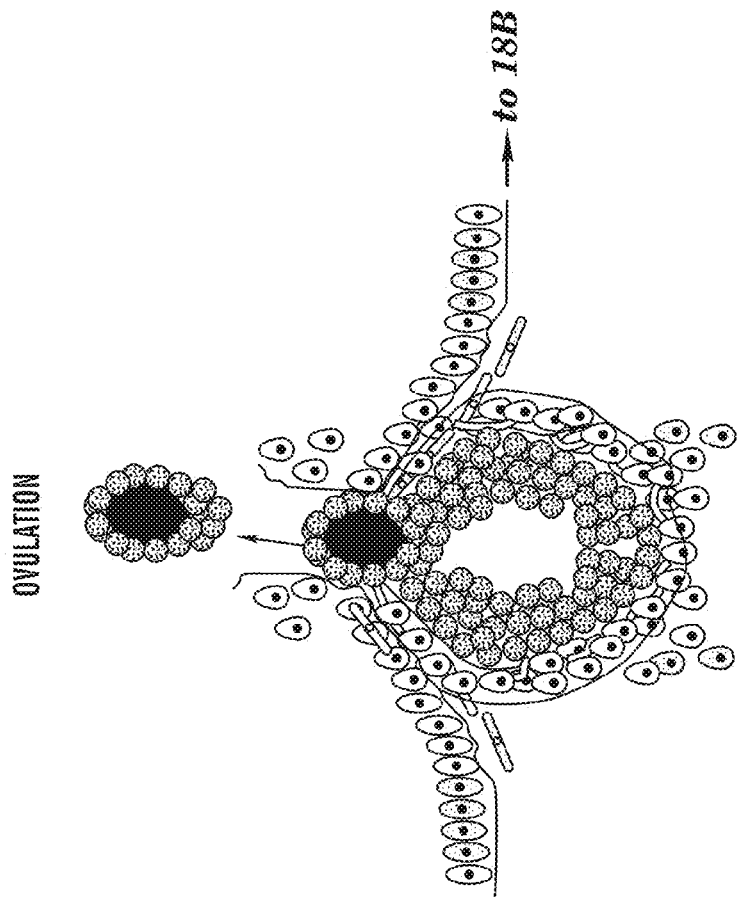

COLLECTING OVARIAN CANCER STEM CELLS FROM OVARIAN CANCER CELLS

CROSS REFERENCE TO RELATED APPLICATIONS

This application is a 371 National Phase Entry Application of co-pending International Application PCT/US2008/070273 filed Jul. 17, 2008, which designated the U.S., and claims the benefit under 35 U.S.C. 119(e) of U.S. Provisional Application Ser. No. 60/959,866 filed on Jul. 17, 2007, the contents of which is incorporated herein by reference.

The sequence listing of the present application has been submitted electronically via EFS-Web as an ASCII formatted sequence listing with a file name "20100113_SEQ_030258-059682-US", creation date of Jan. 14, 2010 and a size of 29,443 bytes. The sequence listing submitted via EFS-Web is part of the specification and is herein incorporated by reference in its entirety.

GOVERNMENT SUPPORT

The present application was made with Government support under Grant Numbers CA17393 and HD32112 awarded by the National Institutes for Health (NIH). The Government of the United States has certain rights in the invention.

FIELD OF THE INVENTION

The present invention relates generally to methods and compositions to treat cancer, and more particularly to treating and/or preventing ovarian cancer, in particular where the ovarian cancer comprises ovarian cancer stem cells. The present invention further provides methods to identify and/or enrich for populations of ovarian cancer stem cells and populations of somatic ovarian stem cells, in particular, enrichment for populations of coelomic somatic ovarian stem cells, sub-coelomic/stromal somatic ovarian stem cells and periphilar medullary somatic ovarian stem cells.

BACKGROUND

Recently, two human primary cancers, leukemia and breast, and several human cancer cell lines, such as central nervous system, gastrointestinal tumors, and retinoblastoma, were shown to possess "side population" (SP) cells that have been described as cancer stem cells (1-5). Cancer stem cells, like somatic stem cells, are thought to be capable of unlimited self-renewal and proliferation. Multipotent cancer stem cells may explain the histologic heterogeneity often found in tumors (6-9).

In addition, cancer progression and metastasis may involve tumor stem cell escape from innate somatic niche regulators. Quiescent somatic stem cells residing in specific tissue niches until activation by injury or other stimuli have been described in skin and hair follicles, mammary glands, intestines, and other organs (10). The evolving evidence that somatic stem cells contribute to normal tissue repair and regeneration suggests the potential for multipotent somatic stem cells in the ovary responsible for regulated surface epithelial repair after ovulatory rupture and possibly the generation of oocyte nurse cells for folliculogenesis (11). Ovarian somatic stem cells would be expected to divide asymmetrically, yielding both a daughter cell that proceeds to terminal differentiation for epithelial repair and an undifferentiated self-copy. Repeated asymmetric self-renewal sets the stage for somatic stem cells or their immediate progenitors to accrue mutations over time, which might ultimately lead to their transformation into cancer stem cells and malignant progression.

Epithelial ovarian cancer, thought to emanate from the surface epithelium of the ovary (12, 13), consists of various histologic subtypes of Mullerian origin (serous, mucinous, and endometrioid), affects >22,000 women in North America per year, and accounts for >16,000 deaths per year with a projected 5 year mortality rate exceeding 70% (14). Aggressive surgical cytoreduction followed by chemotherapy results in complete clinical response in 50-80% of patients with stage III and IV disease. However, the majority of patients will relapse and become drug-resistant (16).

Various types of membrane-spanning ATP-binding cassette transporters, such as the multidrug-resistant gene 1 and breast cancer-resistance protein 1 (BCRP1), contribute to the drug resistance of many cancers, by pumping lipophilic drugs out of the cell (17). Within bone marrow, researchers have defined a subset of verapamil-sensitive BCRP1-expressing cells with the ability to efflux the lipophilic dye Hoechst 33342. This subset has been described as the side population (SP) (18).

Like somatic stem cells, cancer stem cells have the properties of self-renewal, heterologous descendent cells, slow cell-cycle times, and, unlike somatic stem cells, enriched tumor formation (8, 24).

Ovarian cancer patients initially respond well to surgical cytoreduction and chemotherapy. Chemotherapy alone can yield several logs of tumor cytoreduction but seldom a cure. The majority of patients who respond to primary chemotherapy ultimately develop recurrent, usually drug-resistant, disease that is likely due to the ability of ovarian cancer stem cells to escape these drugs.

The ovarian coelomic epithelium covers the ovary as a layer of simple squamous or cuboidal cells. In early embryonic development, the portion of the coelomic epithelium that covers the lateral tip of the urogenital ridge invaginates, while simultaneously undergoing an epithelial to mesenchymal transition (Zhan et al., 2006), giving rise to the mesenchyme of the Mullerian ducts (the anlagen of the oviduct, endometrium, and endocervix). This close embryonic relationship between ovarian coelomic epithelium and Mullerian structures is thought to explain the acquisition of Mullerian architecture and function during neoplastic progression.

Folliculogenesis in the adult ovary is characterized by extensive architectural remodeling that culminates in disruption of the coelomic epithelium and extrusion of the ovum at ovulation (Bjersing and Cajander, 1974, 1975; Bukovsky et al., 2004). After disruption, a subsequent series of molecular events initiates and executes repair of the epithelial wound (Clow et al., 2002; Tan and Fleming, 2004) by either non-stem mediated epithelial cell self-duplication or by stem cell mediated asymmetric division. Asymmetric somatic stem cell division has been proposed as a mechanism by which mutations may be accumulated and perpetuated to future generations (Reya et al., 2001) leading to neoplastic transformation. Concomitantly, previous studies of the coelomic epithelium implicating cyclic re-epithelialization as the source of accrued mutations leading to ovarian cancer (Murdoch et al., 2001) raise the possibility that an asymmetrically dividing coelomic epithelial somatic stem cell can have the propensity for transformation into an ovarian cancer stem cell.

Somatic stem cells are a subset of normal tissue cells that, through asymmetric division, have the ability to self renew and produce lineage committed daughter cells responsible for tissue regeneration and repair (Li and Xie, 2005). Such injury responsive somatic (non-hematopoietic) stem cells and their niches have been described in skin and hair follicle (Blanpain et al., 2004; Fuchs et al., 2004; Lowry et al., 2005; Tumbar et al., 2004), mammary gland (Welm et al., 2003; Welm et al., 2002), intestine (Leedham et al., 2005; Li and Xie, 2005; Mills and Gordon, 2001; Spradling et al., 2001; Vidrich et al., 2003; Williams et al., 1992; Wong, 2004), and other tissues (Alvarez-Buylla and Lim, 2004; Berns, 2005; Imitola et al., 2004; Liu et al., 2004). In some tissues, slow cycling somatic stem cells were initially identified by their ability to retain labels for long periods of time, while asymmetrically derived lineage committed daughter cells dilute out the label during rapid proliferation and terminal differentiation (Albert et al., 2001; Braun and Watt, 2004; Kenney et al., 2001; Morris et al., 1986; Morris and Potten, 1994, 1999; Oliver et al., 2004; Tsujimura et al., 2002; Tumbar et al., 2004; Watt and Hogan, 2000; Wu and Morris, 2005). These studies, as well as those leading to the recent identification of LRCs in the uterine endometrial stroma and myometrium (Szotek et al., 2007), used BrdU (or 3H-Thymidine) or histone H2Bj-GFP labeling to identify and isolate somatic stem cells which, in turn, permitted the discovery of tissue specific surface markers.

Concurrently, Goodell et al. devised another method to isolate previously unidentified stem or progenitor cells by demonstrating that hematopoietic and mammary gland stem cells have the ability to efflux Hoechst 33342 dye through ATP-binding-cassette (ABC) transporters such as Abcg2/Bcrp1 (Goodell et al., 1996; Welm et al., 2002). These "side population" (SP) cells have since been correlated with somatic and cancer stem cells from various tissues (Al-Hajj et al., 2003; Behbod and Rosen, 2005; Bhatt et al., 2003; Haraguchi et al., 2005; Jonker et al., 2005; Kondo et al., 2003; Patrawala et al., 2005; Preffer et al., 2002; Smalley and Clarke, 2005; Smalley et al., 2005; Wulf et al., 2001), including our recent identification of SP cells in ovarian cancer populations (Szotek et al., 2006). Thus, label retention and Hoechst dye efflux are two distinct methods based on stem cell functional properties that can be used individually or potentially in combination to identify candidate somatic stem cells without known surface markers and to define a signature stem cell marker profile.

SUMMARY OF THE INVENTION

In accordance with the present invention, the inventors have discovered a population of ovarian cancer cells that are ovarian cancer stem cells or tumor-initiating cells. The inventors have also discovered that the ovarian cancer stem cells are responsive to Mullerian Inhibiting Substance (MIS). The inventors have also discovered that ovarian cancer stem cells are also more resistant to inhibition by lipophilic chemotherapeutic agents, for example mitoxantrone, daunorubicin, doxorubicin, indolcabazole. The inventors have also discovered that the ovarian cancer stem cells have the ability to efflux liphophilic dyes, for example Hoechst 33342 and are herein termed Hoeschst$^{LOW}$ cells. The inventors have further discovered that the ovarian cancer stem cells are positive for the expression of breast cancer-resistance protein 1 (BCRP1).

The inventors have also discovered the intrinsic repair capacity of the coelomic epithelium emanates from ovarian somatic stem cells such as coelomic somatic stem/progenitor cells. Using a variety of transgenic and cell based techniques, the inventors have discovered three somatic stem cell label-retaining populations in the ovary. The inventors have demonstrated that these somatic ovarian stem cells exist in defined perivascular microenvironments, and have characterized one somatic ovarian stem cell population, the coelomic epithelial label retaining cells (LRCs) in vitro, and have discovered a functional response by coelomic epithelial LRCs to the estrous cycle in vivo.

In further experiments, the inventors have validated the presence of ovarian cancer stem cells by comparing them to a normal somatic ovarian stem cell population, for example somatic ovarian stem cells in the coelomic epithelium that the inventors have also discovered. In some instances, the inventors have discovered a method to study and determine how a normal somatic ovarian stem cell population transforms to become stem cells of ovarian cancer pathology, such as ovarian cancer stem cells as disclosed herein. The inventors have discovered a method whereby the somatic ovarian stem cells can be compared with ovarian cancer stem cells. For example, such methods are useful to determine how, when, and where transformation and progression to the ovarian cancer phenotype occurs, as well as identifying agent that are selective for ovarian cancer stem cells as compared to ovarian somatic stem cells. Using traditional and transgenic pulse chase techniques in conjunction with immunohistochemistry, parabosis and flow cytochemistry, the inventors demonstrate three somatic ovarian cell populations and define their perivascular niche microenvironment and characterize their surface marker profiles.

Accordingly, in one embodiment the present invention is related to methods to identify and enrich for a population of somatic ovarian stem cells, for example methods to identify and enrich for populations of coelomic somatic ovarian stem cells, or populations of subcoelomic/stromal somatic ovarian stem cells, or populations of periphilar medullary somatic ovarian stem cells.

Another embodiment of the present invention is related to methods to identify and enrich for a population of ovarian cancer stem cells.

Another embodiment of the present invention is related to methods to screen for agents that inhibit the growth and/or kill ovarian cancer stem cells as compared to somatic ovarian stem cells.

In another embodiment, the present invention relates to methods for the treatment of ovarian cancer by targeting ovarian cancer stem cells. In such embodiments, a method to prevent and/or treat a subject with ovarian cancer is provided, where the subject is identified to have ovarian cancer comprising ovarian cancer stem cells, and the subject is administered a pharmaceutical composition comprising MIS or a derivative, fragment, analogue or homologue thereof. In some embodiments, the subject is also administered additional cancer therapies, for example chemotherapies, radiotherapy, immune therapy and other agent. In some embodiments, the subject is also administered a BCRP1 inhibitor, for example verapamil.

In such embodiments, a method to prevent and/or treat a subject with ovarian cancer is provided, where the subject is identified to have ovarian cancer comprising ovarian cancer stem cells, and the subject is administered a pharmaceutical composition comprising a BCRP1 inhibitor, for example verapamil. In some embodiments, the pharmaceutical composition comprising a BCRP1 inhibitor also comprises MIS or a derivative, fragment, analogue or homologue thereof.

In another aspect of the invention, methods to treat ovarian cancers by targeting cancer stem cells are disclosed, the method comprising targeting the ovarian cancer stem cell with agents that are agonists to the MIS receptor type II (MISRII). Examples of agonists of MISRII are MIS protein and derivatives and variants thereof. Other agonists of MIS-RII are MIS mimetics, for example pyrazoloanthrone and derivatives thereof.

In some embodiments, the methods of the present invention relate to the treatment of ovarian cancers by targeting ovarian cancer stem cells, the method comprising administering a pharmaceutical composition comprising MIS or derivatives or analogues thereof to the subject with ovarian cancer stem cells. In some embodiments, the pharmaceutical composition administered to the subject comprises additional therapies, for example agents that function as BCRP1 inhibitors. Examples of BCRP1 inhibitors are well known by persons skilled in the art, and one exemplary BCRP1 is a small molecule, for example verapamil. In alternative embodiments, agent that function as BCRP1 inhibitors are nucleic acids, nucleic acid analogues, proteins, peptides, peptidomimetics, antibodies, ribozymes, aptamer etc.

In one aspect of the invention, methods to prevent and/or treat a subject for ovarian cancers, wherein the method comprises the steps (i) of identifying the presence of ovarian cancer stem cells in a subject using the methods as disclosed herein, and wherein if the subject is identified to have ovarian cancer stem cells, the subject is administered a pharmaceutical composition comprising MIS or a derivative, homologue, analogue or fragment thereof and/or a pharmaceutical composition comprising an inhibitor of BCRP1.

As a non-limiting example, pharmaceutical compositions comprising at least one agent that activates MISRII and/or inhibits the expression or activity of BCRP1 is administered to an ovarian cancer stem cell in an effective amount for the treatment of ovarian cancer, wherein the ovarian cancer comprises ovarian cancer stem cells.

In another embodiment, methods for diagnosing a subject at risk of having a recurrent ovarian cancer are disclosed. In some embodiments, the methods comprise assessing the presence of ovarian cancer stem cells in a subject as disclosed herein, for example assessing ovarian cancer cells obtained from a biological sample of a subject for (i) presence of BCRP1 expression and/or (ii) ability to efflux lipophilic dyes (or uptake lipophilic dyes), wherein ovarian cancer cells positive for BCRP1 expression and/or do not retain a lipophilic dye, the subject is identified as being at risk of a recurrent ovarian cancer. In some embodiments, the biological sample is from a biopsy.

In some embodiments, the present invention provides a method for identifying and isolating for ovarian cancer stem cells which comprises contacting a population of ovarian cells with agents reactive for BCRP1 and separating cells positive for the agent reactive for BCRP1 from cells non-reactive to agents for BCRP1, where the cells that are reactive for BCRP1 (i.e cells that express BCRP1) identify ovarian cancer stem cells and can be isolated.

In some embodiments, agents that are reactive to BCRP1 are agents that are reactive to the nucleic acid encoding BCRP1 and/or agents reactive to the protein BCRP1. In some embodiments, the agent is a nucleic acid, nucleic acid analogue, protein or fragment thereof. In some embodiments, the agent is further labeled with a detectable marker, for example a fluorescent marker, or a label that can be used to isolate the agent that is associated, for example interacting with, BCRP1. Such a label is, for example but not limited to metallic beads and streptavidin. In some embodiments, the agent reactive to BCRP1 is a protein or polypeptide, for example but not limited to an antibody with binding affinity for BCRP1, or fragment thereof, for example an anti-BCRP1 antibody, and in some embodiments, a protein agent is a protein binding-partner to BCRP1 or a fragment thereof, for example a BCRP1 ligand or BCRP1 co-factor.

In another aspect, the present invention provides methods for identifying and isolating ovarian cancer stem cells comprising contacting a population of ovarian cells with a lipophilic dye, for example but not limited to Hoeschts 33342, and separating cells that do not incorporate the liphophilic dye or cells that only incorporate a small amount of the dye, from the cells which do incorporate the lipophilic dye, where the cells that do not incorporate the liphophilic dye are identified as ovarian cancer stem cells and can be isolated. In some embodiments, one can identify and isolate ovarian cancer stem cells using both methods as disclosed herein, for example using agents reactive to BCRP1 and using lipophilc dyes, where ovarian cancer stem cells are cells which are positive for BCRP1 expression and do not take up the lipophilic dye.

Method to separate the ovarian cancer cells reactive for agents to BCRP1 and/or liphophilic dyes are well known in the art and can include, for example separation methods such as, but are not limited to fluorescence cell sorting (FACS), fluorometry, flow cytometry, microscopy techniques.

In some embodiments, the ovarian cancer stem cells are identified in a population of ovarian cancer cells, for example a population of ovarian cancer cells present in a biological sample. Such biological samples may be a tissue sample, for example a tumor tissue sample or biopsy tissue sample, for example a biopsy of a cancer or tumor, for example ovarian cancer biopsy. In some embodiments, the tissue sample is obtained from a subject, for example a mammalian, for example but not limited to a human subject.

In some embodiments, the population of ovarian cancer cell comprises ovarian cancer cells, ovarian cancer cells, vulvar epidermal carcinoma cells, cervical carcinoma cells, endometrial edenocarinaoma cells and ovarian adenocarcinoma cells. In alternative embodiments, the population of ovarian cells is a population of primary ascite cells, and in some embodiments, the population of ovarian cells is a population of ovarian cancer cell line cells, for example human or rodent ovarian cancer cell lines. Examples of human and mouse ovarian cancer cells are well known by person skilled in the art, for example, human ovarian cancer cells can include but are not limited to IGROV-1, SK-OV3, OVCAR-3 human cancer cell lines. Examples of mouse ovarian cancer cell lines include, for example but are not limited to MOVCAR7 or 4306 ovarian cancer cell lines.

In some embodiments, ovarian cancer stem cells as disclosed herein are further characterized. Such further characterization includes assessment of multi-drug resistance sensitivity, for example ovarian cancer stem cells that are identified as having multi-drug resistance are identified as being ovarian cancer stem cells. In some embodiments, sensitivity to multi-drug resistance can be determined by assessing sensitivity to an agent which inhibits BCRP1 (herein termed a BCRP1 inhibitor), wherein ovarian cancer cells as disclosed herein that are sensitive to agents BCRP1 inhibitors are identified as ovarian cancer stem cells. In some embodiments, an agent that inhibits BCRP1 is nucleic acid, nucleic acid analogue, small molecule, protein, aptamer, or fragments or variants thereof. In some embodiments, a BCRP1 inhibitor is verapamil or analogues thereof.

Another aspect of the present invention relates to method to identify a population of ovarian cancer stem cells in a biological sample, comprising measuring the biological sample for at least one of: (i) BCRP1 expression, or (ii) ability to efflux a lipophilic dye (iii) multi-drug resistance sensitivity, wherein the biological sample comprises ovarian cells and wherein positiveity for at least one of (i), (ii) or (iii) in the biological sample identifies a population of ovarian cancer stem cells.

Another aspect of the present invention relates to methods to treating ovarian cancer in a subject by targeting ovarian cancer stem cells. In such an embodiment, method for treating a subject with ovarian cancer are provided, comprising administering to the subject an effective amount of MIS or a homologue or variant or derivative thereof, wherein the subject is identified to have an ovarian cancer comprising ovarian cancer stem cells. In some embodiments, the subject has recurrent ovarian cancer.

In some embodiments, the MIS is a functional derivative, analogue or variant thereof. For example, a functional derivative of MIS is a pyrazoloanthrone or derivative or analogue thereof. In alternative embodiments, the MIS is recombinant human MIS. In some embodiments, the effective amount of MIS is an effective amount of a pharmaceutical composition comprising MIS or a variant or derivative thereof. In some embodiments, the pharmaceutical composition further comprises a pharmaceutically acceptable carrier. In additional embodiments, the pharmaceutical composition optionally further comprises a chemotherapeutic agent or an inhibitor of BCRP1.

In further embodiments, MIS can further comprise a targeting moiety, for example a targeting moiety where the targeting moiety targets BCRP1. As a non-limiting example, such a targeting moiety useful in the methods of the present invention is a binding partner to BCRP1, for example a protein ligand to BCRP1 and/or a co-factor of BCRP1.

In some embodiments, the administration of MIS is administered more than once, and in further embodiments, the MIS or derivative thereof is administered before, after or at the same time as the additional therapy.

In some embodiments, the subject is further administered one or more additional therapies, for example but not limited to chemotherapy, radiotherapy, thermotherapy, immunotherapy, hormone therapy, laser therapy and surgery. In some embodiments, the chemotherapy is an agent that inhibits BCRP1. In some embodiments, the agents that inhibit BCRP1 are, for example but not limited to nucleic acids, nucleic acid analogues, small molecule, proteins, aptamer or fragments or derivatives thereof. In some embodiments, a BCRP1 inhibitor is verapamil or a functional derivative, analogue or variant thereof. In alternative embodiments, the chemotherapy is selected from chemotherapeutic agents, for example but not limited to paclitaxel, cisplatin, doxorubicin or analogues thereof.

In some embodiments, the pharmaceutical composition comprising MIS, and optionally comprising additional agents is administered to the subject via intravenous, intradermal, intramuscular, intraarterial, intralesional, percutaneous, subcutaneous, intratumoral, or by aerosol routes. In some embodiments, the subject is administered prophylactic administration and/or therapeutic administration.

In some embodiments, the subject to be treated is a mammal, for example a human. In some instances, the subject undergone one or more cancer therapies, for example but not limited to cancer therapies such as surgery, chemotherapy, radiotherapy, thermotherapy, immunotherapy, hormone therapy and laser therapy.

In another aspect of the present invention, methods to determine if a subject is at risk of having a recurrent ovarian cancer are provided, comprising assessing the presence of ovarian cancer stem cells in a biological sample from the subject, where if the biological sample comprises ovarian cancer stem cells, the subject is identified as being at risk of having a metastasis or recurrent ovarian cancer.

In another aspect of the present invention, methods to identify agents that reduce the self-renewal capacity of an ovarian cancer stem cell are provided, comprising contacting an ovarian cancer stem cell with an agent, and measuring the proliferation of the ovarian cancer cell, whereby an agent that decreases the proliferation as compared to a reference agent or absence of an agent identifies an agent that inhibits the self-renewal capacity of the ovarian cancer stem cell. In such embodiments, the agent is any agent, for example but not limited to nucleic acids, nucleic acid analogues, small molecule, proteins, aptamers, ribosomes etc. Proliferation assays useful in the methods are commonly known by persons of ordinary skill in the art, for example but not limited to the methyliazoletetrazolium (MTT) proliferation assay.

In another aspect of the present invention, methods of treating a subject affected with cancer are also provided, the method comprising assessing the presence of ovarian cancer stem cells in a biological sample obtained from the subject, wherein a clinician reviews the results and if the results indicate the presence of ovarian cancer stem cells in the biological sample, the clinician directs the subject to be treated with an effective amount of a pharmaceutical composition comprising MIS or a homologue or variant or derivative thereof, and/or an BCRP1 inhibitor.

Another aspect of the present invention relates to methods to determine if a subject is at risk of having a recurrent ovarian cancer, the method comprising assessing the presence of ovarian cancer stem cells by the methods as disclosed herein, and if the biological sample is identified to comprise ovarian cancer stem cells, the subject is at risk of having a metastasis or recurrent ovarian cancer. In such embodiments, the subject can be administered an anti-cancer agent or therapy such as administration of BCRP1 inhibitor or MIS or an analogue or derivative thereof according to the methods as disclosed herein, or any other cancer therapy known by a person of ordinary skill in the art.

Another aspect of the present invention relates to methods for identifying and/or isolating and/or enriching for a population of somatic ovarian stem cells, for example somatic coelomic ovarian stem cells, the method comprising contacting a population of cells comprising ovarian cells with agents reactive to cytokeratin-8, β-catenin and E-cadherin and separating reactive positive cells from non-reactive cells, wherein the reactive positive cells are somatic ovarian stem cells. In some embodiments, such a method can further comprise contacting the population of with agents reactive to EpCam and separating reactive positive cells from non-reactive cells, wherein the non-reactive cells are somatic ovarian stem cells such as somatic coelomic ovarian stem cells. In alternative embodiments, where the cells are reactive to agents selective for EpCam, the reactive positive cells are identified as ovarian cancer stem cells.

In further embodiments, the present invention provides methods for isolating or enriching for a population of somatic ovarian stem cells, for example subcoelomic or stromal ovarian stem cells, the method comprising contacting a population of cells comprising ovarian cells with agents reactive to cKIT, αSMA, PDGFRb, NG2, CD44, CD105 and separating reactive positive cells from non-reactive cells are somatic ovarian stem cells such as subcoelomic or stromal ovarian stem cells. In such embodiments, the method can further comprise contacting the population of cells comprising ovarian cells with agents reactive to CD45 or CD 31 and separating reactive positive cells from non-reactive cells, wherein the non-reactive cells are somatic ovarian stem cells, for example somatic subcoelomic or stromal ovarian stem cells.

In further embodiments, the present invention further also provides methods for isolating or enriching for a population of somatic ovarian stem cells, for example periphilar medullary ovarian stem cells, the method comprising contacting a population of cells comprising ovarian cells with agents reactive to cKIT, SF-1, GATA-4, CD44, CD105 and separating reactive positive cells from non-reactive cells are somatic ovarian stem cells such as periphilar medullary ovarian stem cells. In such an embodiment, such a method can further comprise contacting a population of cells comprising ovarian cells with agents reactive to CD45 and/or CD 31 and/or αSMA and separating reactive positive cells from non-reactive cells, wherein the non-reactive cells are somatic ovarian stem cells, for example the non-reactive cells are somatic periphilar medullary ovarian stem cells.

Another aspect of the present invention provides a method for isolating or enriching for a population of ovarian cancer stem cells, the method comprising contacting a population of cells comprising ovarian cells with agents reactive to EpCam, cytokeratin-8, β-catenin and E-cadherin and separating reactive positive cells from non-reactive cells, wherein the reactive positive cells are ovarian cancer stem cells. In such an embodiment, such a method can further comprise contacting a population of cells comprising ovarian cells with agents reactive to MISRII and/or BCRP1 and separating reactive positive cells from non-reactive cells, wherein the reactive positive cells are ovarian cancer stem cells.

In some embodiments, the present invention further provides a method to identify agents that reduce the self-renewal capacity of an ovarian cancer stem cell, comprising contacting an ovarian cancer stem cell as identified according the methods as disclosed herein with an agent, and measuring the proliferation of the ovarian cancer cell, whereby an agent that decreases the proliferation as compared to a reference agent or absence of an agent identifies an agent that inhibits the self-renewal capacity of the ovarian cancer stem cell. In some embodiments, the method can further comprise contacting a somatic ovarian stem cell identified according to the methods as disclosed herein with an agent, and measuring the proliferation of the somatic ovarian cell, and comparing the rate of proliferation of the somatic ovarian stem cell in the presence of the agent with the rate of proliferation of an ovarian cancer stem cell in the presence of the same agent, whereby if the agent decreases the rate of proliferation of the ovarian cancer stem cells as compared to the rate of proliferation of somatic ovarian stem cells identifies an agent that inhibits the self-renewal capacity of the ovarian cancer stem cell.

In another embodiment, the present invention further provides a method for identifying agents which kill or decrease the rate of proliferation of ovarian cancer stem cells, the method comprising: (a) culturing a population of ovarian cancer stem cells as identified according to the methods as disclosed herein, (b) culturing a population of somatic ovarian stem cells as identified according to the methods as disclosed herein, (c) adding to the media of the population of ovarian cancer stem cells one or more agents and adding to the media of the population of somatic ovarian stem cells one or more of the same agents; (d) measuring the rate of proliferation of the population of ovarian cancer stem cells and measuring the rate of proliferation of the population of somatic ovarian stem cells; (e) comparing the rate of proliferation of the population of ovarian cancer stem cells with rate of proliferation of the population of somatic ovarian stem cells, wherein an agent which decreases the rate of proliferation of the ovarian cancer stem cells as compared to the rate of proliferation of somatic ovarian stem cells identifies an agent that kills or decreases the rate of proliferation of an ovarian cancer stem cell. In particular embodiments, the population of somatic ovarian stem cell used in such an assay to identify agents that selectively inhibit the ovarian cancer stem cells are coelomic ovarian stem cell population. In some embodiments, agents used in the methods to identify agents that kill or decrease the rate of proliferation of an ovarian cancer stem cell, such an agent is a nucleic acid, nucleic acid analogue, small molecule, protein, peptiomimetic, antibody, peptide, aptamer, ribozyme, and variants and fragments thereof. Further, proliferation assays useful in identifying agents that kill or decrease the rate of proliferation of an ovarian cancer stem cell are the methyliazoletetrazolium (MTT) proliferation assay or the colony forming unit (CFU) assay, as disclosed herein.

In further aspect, the present invention provides a method of treating a subject affected with cancer, the method comprising assessing the presence of ovarian cancer stem cells in a biological sample obtained from the subject, wherein a clinician reviews the results and if the results indicate the presence of ovarian cancer stem cells in the biological sample, the clinician directs the subject to be treated with an effective amount of a pharmaceutical composition comprising MIS or a homologue or variant or derivative thereof, and/or an BCRP1 inhibitor. In some embodiments, the biological sample is a tissue sample, for example a tissue sample such as a cancer or a tumor, and/or a biopsy tissue sample. In some embodiments, the tissue sample comprises ovarian cancer cells, vulvar epidermal carcinoma cells, cervical carcinoma cells, endometrial edenocarinaoma cells and ovarian adenocarcinoma cells. In a particular embodiment, the tissue sample comprises ascite cells.

In some embodiments, where agent is used to identify and/or enrich for a population of somatic ovarian stem cells or a population of ovarian cancer stem cells, the agent can be a nucleic acid or protein or analogues or fragments thereof. For example, an agent can be reactive to an expression product, for example protein and/or gene transcript such as mRNA, or fragments of an expression product, encoded by genes cytokeratin-8, β-catenin and E-cadherin, EpCam, cKIT, αSMA, PDGFRb, NG2, CD31, CD44, CD105, SF-1 or GATA-4. In some embodiment, the gene transcript is selected from the group consisting of RNA, messenger RNA, or genomic DNA. In some embodiments, a nucleic acid agent is DNA, RNA or nucleic acid analogues, such as PNA (peptide nucleic acid), pc-PNA (pseudo-complementary PNA), LNA (locked nucleic acid) and analogues and derivatives thereof. In some embodiments, a protein agent useful in the methods as disclosed herein is an antibody or antibody fragment thereof. In further embodiments, an agent reactive to the genes to identify somatic ovarian stem cell population and/or an ovarian cancer stem cell populations are small molecule agents or aptamer agents or antibody fragment agents.

A further embodiment of the present invention relates to kits to identify or enrich for a population of ovarian cancer stem cells in a biological sample, the kit comprising agents reactive to EpCam, cytokeratin-8, β-catenin and E-cadherin, and can optionally further comprise agents reactive to BCRP1 and/or MIS. Another embodiment provides a kit to identify somatic coelomic ovarian stem cells in a biological sample, the kit comprising agents reactive to EpCam, cytokeratin-8, β-catenin and E-cadherin. Another kit useful according to the present invention is a kit to identify or enrich for a population of subcoelomic/stromal ovarian stem cells in a biological sample, the kit comprising agents reactive to cKIT, αSMA, PDGFRb, NG2, CD44, CD105, and can optionally comprise an agent reactive to CD45 and/or an agent reactive to CD31. A further embodiment of the present invention relates to a kit to identify or enrich for a population of somatic periphilar medullary ovarian stem cells in a biological sample, the kit comprising agents reactive to cKIT, SF-1, GATA-4, CD44, CD105, and can optionally comprise agents reactive to CD 45 and/or CD31 and/or αSMA. A further embodiment provides a kit to identify or enrich for a population of ovarian stem cells in a biological sample, the kit comprising at least 3 agents reactive to cytokeratin-8, β-catenin and E-cadherin, EpCam, cKIT, αSMA, PDGFRb, NG2, CD31, CD44, CD105, SF-1 or GATA-4, MIS or BCRP1. In some embodiments, the kits comprise agent that are nucleic acid agents, nucleic acid analogue agents or protein agents or fragments or analogues thereof. In some embodiments, the protein agents are antibody, anitmer, aptamer or fragments thereof, and in some embodiments, the kits can be in the form of ELISAs and/or protein chip array formats. In alternative embodiments, where the agent is a nucleic acid agent, the kit can be in the format of, for example a microarray chip or nucleic acid binding chip. In some embodiments, the kits as disclosed herein can be used for isolation of the ovarian stem cell of interest.

BRIEF DESCRIPTION OF FIGURES

FIGS. 4A-4F shows In vivo growth characteristics of MOVCAR 7 SP and NSP cells. MOVCAR 7 cells were sorted for SP and NSP (4A), and nude mice were injected with equal numbers of SP and NSP cells [group I, $5\times10^5$ cells per animal (4B); group II, $7.5\times10^5$ cells per animal (data not shown)]. Measurable tumors were detected in SP-injected group I animals at 10 weeks (three of three) (4B) and SP-injected group II animals at 7 weeks (Table 1) after implantation, whereas group I (zero of three) (4B) and group II NSP-injected animals did not demonstrate tumors at the first appearance of SP tumors. The appearance of NSP tumors was delayed in group I and II NSP tumors until 14 and 11 weeks after injection. Sorting purity analysis (4C and 4D) showed ~93% purity in both SP and NSP sorts, identifying contamination by NSP sorts with SP cells. NSP tumors harvested after euthanization revealed the presence of a verapamil-sensitive SP of similar percentage to that initially injected due to incomplete sorting (4E and 4F).

FIGS. 5A-5G show MOVCAR 7 SP cells respond to MIS in vitro. MOVCAR 7 cells express the MISRII by epifluorescent and confocal microscopy (5A-5C). RT-PCR evaluation of SP cells demonstrated the presence of an intact MIS signaling pathway (5D, left to right: SMAD 1, SMAD 5, SMAD 8, MIS type I receptors Alk 2 and Alk 3, and the MISRII). The proliferation of MOVCAR 7 SP and NSP cells were analyzed after the first sort by MTT assay (5E) and demonstrate inhibition of both SP (86%) and NSP (93%) cells by MIS versus vehicle. SP cells were serially sorted two more times, demonstrating that enriched SP cells remain responsive to MIS (5F, 93% inhibition; 5G, 94% inhibition). All experiments were performed in triplicate.

FIGS. 6A-6H show human ovarian cancer cell lines and primary ascites from patients have SPs and express the BCRP1 transporter. Human ovarian cancer cell line IGROV-1 had a verapamil-sensitive SP (6A and 6E), whereas OVCAR-8 did not (6B and 6F). Human serous adenocarcinoma ascites patients 215 and 216 have small verapamil-sensitive SPs (6C, 6D, 6G, and 6H).

FIG. 8A shows ovarian cancer cell lines OVCAR-3, OVCAR-8, SKOV-3, IGROV-1 and AC-01. FIG. 8B shows primary ascite cells from 5 different patients. OVCAR-3, OVCAR-8, SKOV-3 (dim), IGROV-1, patient 203 (dim), and patient 216 were ESA-positive. OVCAR-3, OVCAR-8, and patient 214 (dim) were positive for CD24. AC-01 and patient 214 demonstrated CD44 staining. No significant c-kit staining was observed.

FIG. 11A depicts the uniform loss of BrdU/IdU or GFP signal predicted by a self-duplication coelomic repair model (left) and in contrast, the predicted retention of label by a stem cell asymmetric division coelomic repair model (right). Gross inspection of 3 month chase H2Bj-GFP ovaries demonstrated that GFP LRCs congregated in a perivascular location following the vascular supply (11B & 11C). Label retention in 3 month chase ovaries identified coelomic LRCs, subcoelomic/stromal LRCs, and perihilar medullary LRCs (11D) FIGS. 11E-11F represent higher magnification of CE and SC/Str LRCs by both H2Bj-GFP (11E) and BrdU (11F) pulse-chase methods. FIG. 11G-11H represent higher magnification of peri-hilar medullary (PHM) LRCs by both H2Bj-GFP (11G) and BrdU (11H) pulse-chase methods. Number of mice (n=) at each timepoint is shown. FIG. 11I is a schematic diagram depicting the three identified LRC populations and their relationship to each other, the vasculature, and maturing follicles (CE=coelomic; SC/Str subcoelomic/stromal, and PHM=peri-hilar medullary). (O=Oocyte; GC=Granulosa Cells; T=Theca; BV=Blood Vessel).

FIGS. 16A-16B shows characterization of $Lin^-cKit^+Sca-1^+$ hematopoietic stem cell label retention. Flow cytometry analysis of embryonic pulse H2Bj-GFP bone marrow was used to characterize Rosa26-rtTA; tetO-H2Bj-GFP in hematopoietic stem cells by colocalization with the known hematopoietic stem cell phenotype $Lin^-cKit^+Sca-1^+$. Whole bone marrow demonstrated a significantly lower labeling efficiency (37.6±12% SE, standard error, panel 16A) as compared to $Lin^-cKit^+Sca-1^+$ hematopoietic stem cells (81.36±7.6%, panel 16B, p=0.016). After 2 and 6 month chase periods there was significant enrichment of GFP label retention in $Lin^-Kit^+Sca-1^+$ hematopoietic stem cells (9.64±2.1% & 2.93±1.09%, panel 16B) as compared to the whole bone marrow (0.47±0.22% & 0.21±0.10%, panel 16A, p=0.017 & p=0.003). These findings demonstrate the ability of the Rosa26-rtTA; tetO-H2Bj-GFP to identify hematopoietic and thus somatic stem cells.

FIGS. 18A-18D show a schematic of a proposed mechanism of coelomic LRC mediated ovulatory wound healing and the role of SC/Str and PHM LRCs in folliculogenesis. Ovulation of the oocyte results in disruption of both the sub-coelomic/stromal and coelomic cells (panel 18A). Reepithelialization of the wound occurs by a combined mechanism of stem cell proliferation and daughter cell migration as depicted in panel 18B. SC/Str and PHM LRCs appear to play a role in folliculogenesis as depicted in panel 18C & 18D. First, during follicular recruitment the SC/Str LRCs proliferate and incorporate/assist in the development of the thecal capillary network. At the same time, as granulosa cells develop previous work has shown that they begin to produce Kit-ligand which has been proposed to play a role in theca cell recruitment (panel 18C). Our observation that the PHM LRCs are c-Kit receptor positive and are observed to proliferate and incorporate in the maturing follicle (panel 18D) suggests that the PHM LRCs may serve as a reservoir for Kit-ligand induced theca cell differentiation and recruitment.

DETAILED DESCRIPTION

Figure 1A:
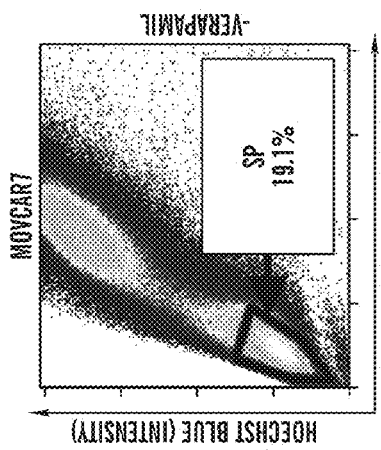
FIGS. 1A-1H show identification of SP cells in established mouse ovarian cancer cell lines. MOVCAR 7 and 4306 cell lines were labeled with Hoechst 33342 dye and analyzed by flow cytometry before (A and B) and after (C and D) treatment with verapamil. MOVCAR 7 and 4306 cells were examined for colocalization of Brcp1 immunoreactivity and Hoechst dye uptake. Hoechst$^{Low}$ cells (E and F; dashed circle and arrows) show Bcrp1 immunoreactivity (G and H; arrows).

As disclosed herein, one aspect of the present invention relates to methods to identify a population of ovarian cancer stem cells present in a biological sample. In another aspect of the present invention, methods to isolate ovarian cancer stem cells are provided. In one embodiment, one method to isolate and identify a population of ovarian cancer stem cells comprises contacting a population of ovarian cells with a agent reactive to breast cancer-resistance protein 1 (BCRP1) and selecting and isolating cells that are reactive with the agent for BCRP1. In another embodiment, the method comprises contacting a population of ovarian cells with a liphophilic dye, for example Hoechst 33342 and selecting for the cells that do not take up the dye.

As disclosed herein, the inventors have discovered a population of ovarian cancer cells that are ovarian cancer stem cells or tumor-initiating cells. The inventors have also discovered that the ovarian cancer stem cells are responsive to Mullerian Inhibiting Substance (MIS). The inventors have also discovered that ovarian cancer stem cells are also more resistant to inhibition by lipophilic chemotherapeutic agents, for example mitoxantrone, daunorubicin, doxorubicin, indolcabazole. The inventors have also discovered that the ovarian cancer stem cells have the ability to efflux liphophilic dyes, for example Hoechst 33342 and are herein termed Hoechst-$^{LOW}$ cells. The inventors have further discovered that the ovarian cancer stem cells are positive for the expression of breast cancer-resistance protein 1 (BCRP1). Accordingly, in one embodiment the present invention is related to methods As disclosed herein, the inventors have discovered that distinct histologic types of genetically engineered mouse ovarian cancer cells (MOVCAR 7 and 4306) have a proportionately large side population (SP), and thus the inventors have discovered a new model to study ovarian cancer stem cell biology. The inventors also discovered a SP in human ovarian cancer cell lines (IGROV-1, SK-OV3, and OVCAR-3) and in patient primary ascites cells. The inventors used the MOVCAR 7 cell line to demonstrate that SP cells can reconstitute colonies in vitro, form tumors earlier than non-side population (NSP) cells in vivo, and remain responsive to Mullerian Inhibiting Substance (MIS). The inventors have discovered that the SP phenotype is a marker for ovarian cancer stem cells and that MIS can inhibit proliferation of both stem cell and non-stem cancer cells, as compared with the lipophilic chemotherapeutic doxorubicin, which more effectively inhibited the NSP. The inventors discoveries are useful in methods to treat and to develop therapeutic strategies to treat recurrent ovarian cancer, for example recurrent ovarian cancers after treatment with transporter substrates such as anthracyclines, which typically cytoreduce the ovarian cancer but essentially never cure. The inventors discovery of the ovarian cancer stem cell population in subjects is also useful in advancing the development of novel therapeutic strategies in the management of this ovarian cancer.

Accordingly, the in another aspect of the invention, the method to treat a subject with ovarian cancer are provided, where the subject is identified to have ovarian cancer comprising ovarian cancer stem cells, and the subject is administered a pharmaceutical composition comprising MIS or a derivative or homologue thereof. In some embodiments, the subject is also administered additional cancer therapies, for example chemotherapies and other agent. In some embodiments, the subject is also administered a BCRP1 inhibitor, for example verapamil.

The inventors have also discovered the intrinsic repair capacity of the coelomic epithelium emanates from ovarian somatic stem cells such as coelomic somatic stem/progenitor cells in the normal ovary. Using a variety of transgenic and cell based techniques, the inventors have discovered three ovarian somatic stem cell populations which are also label-retaining cell (LRC) populations in the ovary. The inventors have demonstrated that these somatic ovarian stem cells exist in defined perivascular microenvironments, and have characterized one somatic ovarian stem cell population, the coelomic epithelial label retaining cells (LRCs) in vitro, and have discovered a functional response by coelomic epithelial LRCs to the estrous cycle in vivo.

Using traditional and transgenic pulse chase techniques in conjunction with immunohistochemistry, parabosis and flow cytochemistry, the inventors have discovered the surface marker profiles of three somatic ovarian cell populations. The inventors discovered that somatic coelomic ovarian stem cell population was characterized to have positive surface marker profiles for cytokeratin-8, β-catenin and E-cadherin, but negative expression for EpCam. In contrast, the inventors discovered ovarian cancer stem cells have positive surface marker profiles for EpCam as well as positive for cytokeratin-8, β-catenin and E-cadherin, thereby the inventors have discovered a method to identify and distinguish a population of ovarian cancer stem cells from a population of coelomic ovarian stem cells.

The inventors further discovered that a subcoelomic or stromal ovarian stem cell population was characterized to have positive surface marker profiles for cKIT, αSMA, PDG- FRb, NG2, CD44, CD105, but negative for the expression CD45 and CD31. The inventors further discovered that a periphilar medullary ovarian stem cell population was characterized to have positive surface marker profiles for cKIT, SF-1, GATA-4, CD44, CD105, but negative for the expression CD45 and/or CD 31 and/or αSMA.

Accordingly, the inventors have discovered methods to identify, isolate and enrich for three populations of somatic ovarian stem cells; a coelomic ovarian stem cell population, a subcoelomic/stromal ovarian stem cell population and a periphilar medullary ovarian stem cell population, as well as methods to identify, isolate and enrich for populations of ovarian cancer stem cells.

In further experiments, the inventors have validated the presence of ovarian cancer stem cells by comparing them to a normal somatic ovarian stem cell population the inventors the inventors discovered in the coelomic epithelium. In some instances, the inventors have discovered a method to study and determine how a normal somatic ovarian stem cell population transforms to become stem cells of ovarian cancer pathology, such as ovarian cancer stem cells as disclosed herein. The inventors have discovered a method whereby the somatic ovarian stem cells can be compared with ovarian cancer stem cells, for example, such methods are useful to determine how, when, and where transformation and progression to the ovarian cancer phenotype occurs, as well as identifying agent that are selective for ovarian cancer stem cells as compared to ovarian somatic stem cells.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "Mullerian Inhibiting Substance" and "MIS" are used interchangeably herein and is also known as anti-Müllerian hormone or AMH, refer to compounds and materials which are structurally similar to MIS. Examples of such intended substances are for example, salts, derivatives and aglycone forms of MIS. Additionally, the present invention is intended to include mutant forms of MIS which have substantially the same biological activity as MIS. Examples of such mutant MIS molecules carrying a deletion, insertion, or alteration in amino acid sequence. MIS can be obtained from any mammalian source or from non-mammalian sources through the use of recombinant DNA technology, or from chemical synthesis of the MIS protein. For reference purposes only, the human MIS nucleic acid corresponds to Accession No: NM_000479 or RefSeq ID No: $KO_{3474}$ (GeneID: 268), herein referred to as SEQ ID NO: 15 which are incorporated herein by reference. The amino acid sequence for MIS corresponds to SEQ ID NO: 16, and corresponds to Accession No: NP_000470.

The term "Mullerian Inhibiting Substance type II receptor" or "MISRII" are used interchangeably herein refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 and GenBank No: AF172932, and corresponds to SEQ ID NO: 17 and is incorporated herein by reference. The amino acid sequence for MISRII corresponds to SEQ ID NO: 18, and corresponds to Accession No: NP_065434.

The term "functional derivative" and "mimetic" are used interchangeably, and refers to compounds which possess a biological activity (either functional or structural) that is substantially similar to a biological activity of the entity or molecule for which it's a functional derivative. The term functional derivative is intended to include the fragments, variants, analogues or chemical derivatives of a molecule.

The term "derivative" as used herein refers to peptides which have been chemically modified, for example but not limited to by techniques such as ubiquitination, labeling, pegylation (derivatization with polyethylene glycol) or addition of other molecules.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a MIS for example, is meant to refer to a molecule substantially similar in structure and function, i.e. where the function is the ability to bind with MISRII, to either bind to the entire MISRII molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

For example, a variant of an MIS can contain a mutation or modification that differs from a reference amino acid in NM_000479 (SEQ ID NO: 16). In some embodiments, a variant can be a different isoform of MIS or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W.H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of, for example MIS to bind and activate MISRII). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents. As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

"Insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "functional derivative" and "mimetic" are used interchangeably, and refers to a compound which possess a biological activity (either functional or structural) that is substantially similar to a biological activity of the entity or molecule its is a functional derivative of. The term functional derivative is intended to include the fragments, variants, analogues or chemical derivatives of a molecule.

A "fragment" of a molecule, is meant to refer to any contiguous polypeptide subset of the molecule. Fragments of, for example MIS which have the same activity as that of MIS encoded by NM_000479, referred to herein as SEQ ID NO: 15 (i.e. a fragment of an MIS peptide which can bind and activate MISRII as the MIS polypeptide corresponding to SEQ ID NO: 16) and which are soluble (i.e. not membrane bound) are also encompassed for use in the present invention.

An "analog" of a molecule such as MIS, for example an analogue of the protein encoded by NM_000479 (SEQ ID NO: 15) is meant to refer to a molecule similar in function to either the entire molecule or to a fragment thereof of SEQ ID NO: 16. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

As used herein, the term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions. The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

Determination of homologs of the genes or peptides of the present invention can be easily ascertained by the skilled artisan. The terms "homology" or "identity" or "similarity" are used interchangeably herein and refers to sequence similarity between two peptides or between two nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

In one embodiment, the term "MIS peptide homolog" refers to an amino acid sequence that has 40% homology to the full length amino acid sequence of the MIS as disclosed herein, for example the MIS peptide such as SEQ ID NO: 16 or a polypeptide encoded by NM_000479 (SEQ ID NO: 15) as disclosed herein, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.).

For sequence comparison, typically one sequence acts as a reference sequence, to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=4, and a comparison of both strands.

The term "analog" as used herein, is indented to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

The term "substitution" when referring to a peptide, refers to a change in an amino acid for a different entity, for example another amino acid or amino-acid moiety. Substitutions can be conservative or non-conservative substitutions.

As used herein, the term "subject" refers to any living organism which can be administered to the pharmaceutical compositions of the present invention and in which cancer or a proliferative disorder can occur. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" also includes living organisms susceptible to conditions or disease states as generally disclosed, but not limited to, throughout this specification. Examples of subjects include humans, dogs, cats, cows, goats, and mice, including transgenic species The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposition, affection.

The term "effective amount" as used herein refers to the amount of an agent and/or a pharmaceutical composition required to reduce at least one of the symptom of the disease or disorder. For example, an effective amount is the amount of required to reduce a symptom of ovarian cancer by at least 10%. An effective amount is also the amount sufficient to prevent the development of a disease symptom, or to reduce a symptom or reduce the rate if a symptom progression.

The term 'malignancy' and 'cancer' are used interchangeably herein, refers to diseases that are characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "treating" includes preventing the progression and/or reducing or reversing at least one adverse effect or symptom of a condition, disease or disorder associated with inappropriate proliferation, for example cancer.

As used herein, the terms "administering" and "introducing" are used interchangeably herein and refer to the placement of the pharmaceutical compositions as disclosed herein into a subject by a method or route which results in at least partial localization of the pharmaceutical compositions at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions of the present invention comprising pyrazoloanthrones and optionally other agents or material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising; nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within an ovarian cancer cell.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular to a cell type, or molecules expressed by the cell type. Preferably, such markers are proteins, and more preferably, possess an epitope for antibodies or other binding molecules available in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes as disclosed herein, ability to migrate under particular conditions, and the ability to differentiate along particular lineages. Markers may be detected by any method available to one of ordinary skill in the art. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

The term 'lineages" as used herein refers to a term to describe cells with a common ancestry, for example cells that are derived from the same ovarian cancer stem cell.

As used herein, the term "clonal cell line" refers to a cell lineage that can be maintained in culture and has the potential to propagate indefinitely. A clonal cell line can be a stem cell line or be derived from a stem cell, and where the clonal cell line is used in the context of clonal cell line comprising stem cells, the term refers to stem cells which have been cultured under in vitro conditions that allow proliferation without differentiation for months to years. Such clonal stem cell lines can have the potential to differentiate along several lineages of the cells from the original stem cell.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not cardiovascular stem cells or cardiovascular stem cell progeny of the invention.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

The articles "a" and "an" are used herein to refer to one or to more than one (i.e., to at least one) of the grammatical object of the article. By way of example, "an element" means one element or more than one element.

Isolating and/or Enriching for Populations of Ovarian Cancer Stem Cells

As disclosed herein, the inventors have discovered a method to identify, isolate and enrich for ovarian cancer stem cells. One aspect of the present invention provides methods for identification, isolation and enrichment of ovarian cancer stem cells. The inventors have discovered ovarian cancer stem cells are positive for the expression of the Breast cancer resistance protein 1 (BCRP1) gene. Encompassed in the methods of the present invention are methods for identification, isolation and enrichment of ovarian cancer stem cells using agents that are reactive to BCRP1, for example agents reactive to the nucleic acids encoding BCRP1, for example mRNA BCRP1 and in another embodiment, agents are reactive to the expression products of the nucleic acid encoding BCRP1, for example agent reactive to BCRP1 protein or fragments thereof are useful in the methods as disclosed herein. In another embodiment encompasses methods for the identification, isolation and enrichment of populations of ovarian cancer stem cells, the methods comprising using conventional methods of using reporter genes operatively linked to the promoters of BCRP1 or homologues or variants thereof. In such embodiments, when cells express the BCRP1 protein the cells will also express the reporter gene operatively linked to the promoter of BCRP1, and the expression of the reporter gene can be used to isolate, identity and enrich for populations of ovarian cancer stem cells.

BCRP1, is also known in the art as the ABCG2 transporter is shown herein as a marker for stem cell-like Hoechst 33342- excluding SP of ovarian cancer stem cells. Also disclosed herein, BCRP1 can confer ovarian cancer cell drug resistance-associated efflux of many lipophilic chemotherapeutic agents, such as for example mitoxantrone, daunorubicin, doxorubicin, indolcarbazole, and others (22). BCRP1 is known in the art under alias of ATP binding cassette transporter G2, placenta specific MDR, mxr1, abcg2, ATP binding cassette sub family g white member 2, cdw338, mitoxantrone resistance, breast cancer resistance, est157481, BCRP, mgc102821, BCRP1, BMDP, ABC transporter, MRX, MRX, ABC15, ABCP, ATP binding cassette sub family g member 2, and for references purposes, the human BCRP1 nucleic acid sequence corresponds to RefSeq ID: NM_004827 and Accession Number AF103796, which correspond to SEQ ID NO: 19 and is incorporated herein by reference. The amino acid sequence for BCRP1 is Accession No: NP_004818.2 and corresponds to SEQ ID NO: 20.

As disclosed herein, the ovarian cancer stem cells have the ability to efflux lipophilic molecules, for example lipophilic dyes for example but not limited to Hoechst 33342. In another embodiment, methods for the identification, isolation and enrichment of populations of ovarian cancer stem cells comprises contacting a population of cells with a lipophilic dye, for example Hoechst 33342 and selecting for cells that do not take up the dye, or take up only a small amount of dye as compared to other cells. In such an embodiment, cells that do not comprise as much dye as compared to other, such as somatic non-stem cells are ovarian cancer stem cells.

As used herein, the present invention provides methods to enrich a population of ovarian cancer stem cells. In some embodiments, this encompasses enriching a population of ovarian cancer stem cells from a population of cells comprising ovarian cells. As used herein, the term "enriching" or "enrich for" are used interchangeably, and refers to increasing the population of cells of interest, for example ovarian cancer stem cells in a population of cells, for example increasing the percentage of ovarian cancer stem cells by about 10% or about 20% or about 30%, or about 40% or about 50% or about 60% or greater than 60% within the total population cells as compared to the starting population of cells.

Isolating and Enriching for Populations of Somatic Ovarian Stem Cells

As disclosed herein, the inventors have discovered a method to identify, isolate and enrich for populations of somatic ovarian stem cells, in particular coelomic ovarian stem cell populations, subcoelomic/stromal ovarian stem cell populations and periphilar medullary ovarian stem cell populations, in addition to methods to identify and isolate ovarian cancer stem cell populations.

The inventors have discovered somatic coelomic ovarian stem cells are positive for the expression of surface marker proteins cytokeratin-8, β-catenin and E-cadherin, but negative expression for the surface marker protein EpCam. In contrast, the inventors also discovered that ovarian cancer stem cells are positive for surface marker protein EpCam, as well as positive for surface marker proteins cytokeratin-8, β-catenin and E-cadherin. Accordingly, the present invention provides methods to identify and enrich for populations of ovarian stem cells that are positive for cytokeratin-8, β-catenin and E-cadherin, which can be further characterized based on their expression profile for EpCam, where negative expression for the Epcam surface marker expression identifies the ovarian stem cell population as somatic coelomic ovarian stem cells, whereas positive expression for the Epcam surface marker identifies the ovarian stem cell population as ovarian cancer stem cells. Thus, in one embodiment, the present invention provides a method to identify, distinguish and enrich for a population of ovarian cancer stem cells from a population of coelomic ovarian stem cells by determining the expression of EpCam in a population of ovarian stem cells that express the surface markers cytokeratin-8, β-catenin and E-cadherin, wherein negative expression for EpCam identifies and can be used to enrich for ovarian stem cell populations such as coelomic ovarian stem cells, whereas positive expression for EpCam identifies and can be used to enrich for populations of ovarian cancer stem cells.

Encompassed in the methods of the present invention are methods for identification, isolation and enrichment of populations of somatic ovarian stem cells, such as coelomic ovarian stem cells using agents that are reactive to cytokeratin-8, β-catenin and E-cadherin and EpCam, for example agents reactive to the nucleic acids encoding cytokeratin-8, β-catenin and E-cadherin and EpCam, for example mRNA cytokeratin-8, β-catenin and E-cadherin and EpCam and in another embodiment, agents are reactive to the expression products of the nucleic acid encoding cytokeratin-8, β-catenin and E-cadherin and EpCam, for example agent reactive to cytokeratin-8, β-catenin and E-cadherin and EpCam protein or fragments thereof are useful in the methods as disclosed herein.

In another embodiment encompasses methods for the identification, isolation and enrichment as well as distinguishing between ovarian cancer stem cell and coelomic ovarian stem cell populations, the methods comprising using conventional methods of using reporter genes operatively linked to the promoters of EpCam or homologues or variants thereof. In such embodiments, cells that express the surface markers cytokeratin-8, β-catenin and E-cadherin and also express the EpCam surface marker protein, the cells will also express the reporter gene operatively linked to the promoter of EpCam, and the expression of the reporter gene can be used to isolate, identity and enrich for ovarian cancer stem cells, whereas lack of expression of the reporter gene can be used to isolate, identity and enrich for somatic ovarian stem cells such as coelomic ovarian stem cells. In alternative embodiments, a different reporter gene can be expressed when the EpCam is not expressed, which can be used to identify and enrich for a population of somatic ovarian stem cells such as coelomic ovarian stem cells. In some embodiments, a reporter gene is expressed when EpCam is expressed, which can be used to isolate and identity and enrich for a population of ovarian cancer stem cells, and a different reporter gene, such as a different fluorescent reporter gene can be expressed when the EpCam is not expressed, which can be used to identify and enrich for a population of somatic ovarian stem cells such as coelomic ovarian stem cells.

Another aspect of the present invention relates to the discovery and identification of a subcoelomic or stromal ovarian stem cell population that are positive for the expression of surface marker cKIT, αSMA, PDGFRb, NG2, CD44, CD105, but negative for the expression of surface markers CD45 and CD31. In another embodiment encompasses methods for the identification, isolation and enrichment of a population of subcoelomic/stromal ovarian stem cells, the methods comprising using conventional methods of using reporter genes operatively linked to the promoters of cKIT and/or αSMA and/or PDGFRb and/or NG2 and/or CD44 and/or CD105 or homologues or variants thereof. In additional embodiments, a different reporter gene can be expressed when the CD45 and/or CD31 is not expressed, which can be used to identify and enrich for a population of somatic ovarian stem cells such as subcoelomic/stromal ovarian stem cells.

The inventors further discovered that a periphilar medullary ovarian stem cell population was characterized to have positive surface marker profiles for cKIT, SF-1, GATA-4, CD44, CD105, but negative for the expression CD45 and/or CD31 and/or αSMA. In another embodiment encompasses methods for the identification, isolation and enrichment of a population of periphilar medullary ovarian stem cells, the methods comprising using conventional methods of using reporter genes operatively linked to the promoters of cKIT and/or SF-1 and/or GATA-4 and/or CD44 and/or CD105 or homologues or variants thereof. In additional embodiments, a different reporter gene can be expressed when the CD45 and/or CD31 and/or αSMA are not expressed, which can be used to identify and enrich for a population of somatic ovarian stem cells such as periphilar medullary ovarian stem cells.

As used herein, the present invention provides methods to enrich a population of somatic ovarian stem cells, such as for example coelomic ovarian stem cells, subcoelomic/stromal ovarian stem cells and periphilar medullary ovarian stem cells. In some embodiments, this encompasses enriching a population of somatic ovarian stem cells from a population of cells comprising ovarian cells. As used herein, the term "enriching" or "enrich for" are used interchangeably, and refers to increasing the population of cells of interest, for example somatic ovarian stem cells in a population of cells, for example increasing the percentage of somatic ovarian stem cells by about 10% or about 20% or about 30%, or about 40% or about 50% or about 60% or greater than 60% within the total population cells as compared to the starting population of cells.

Method to determine the expression of surface marker proteins as disclosed herein, such as for example but not limited to, BCRP1 cytokeratin-8, β-catenin and E-cadherin, EpCam, cKIT, αSMA, PDGFRb, NG2, CD31, CD44, CD105, SF-1 or GATA-4 are well known by persons skilled in the art and are encompassed for use in the methods of the present invention. Such methods of measuring gene expression of BCRP1 are well known in the art, and are commonly performed on using DNA or RNA collected from a biological sample of the cells, and can be performed by a variety of techniques known in the art, including but not limited to, PCR, RT-PCR, quantitative RT-PCR (qRT-PCR), hybridization with probes, northern blot analysis, in situ hybridization, microarray analysis, RNA protection assay, SAGE or MPSS. In some embodiments, the probes used detect the nucleic acid expression of the marker genes can be nucleic acids (such as DNA or RNA) or nucleic acid analogues, for example peptide-nucleic acid (PNA), pseudocomplementary PNA (pcPNA), locked nucleic acid (LNA) or analogues or variants thereof.

In other embodiments, the expression of the markers can be detected at the level of protein expression. The detection of the presence of nucleotide gene expression of the markers, or detection of protein expression can be similarity analyzed using well known techniques in the art, for example but not limited to immunoblotting analysis, western blot analysis, immunohistochemical analysis, ELISA, and mass spectrometry. Determining the activity of the markers, and hence the presence of the markers can be also be done, typically by in vitro assays known by a person skilled in the art, for example Northern blot, RNA protection assay, microarray assay etc of downstream signaling pathways of BCRP1, cytokeratin-8, β-catenin and E-cadherin, EpCam, cKIT, αSMA, PDGFRb, NG2, CD31, CD44, CD105, SF-1 or GATA-4. In particular embodiments, qRT-PCR can be conducted as ordinary qRT-PCR or as multiplex qRT-PCR assay where the assay enables the detection of multiple markers simultaneously, for example BCRP1, MIS receptor Type II (MISRII), cytokeratin-8, β-catenin and E-cadherin, EpCam, cKIT, αSMA, PDGFRb, NG2, CD31, CD44, CD105, SF-1 or GATA-4, together or separately from the same reaction sample.

In some embodiments, conventional methods to isolate a particular stem cell of interest involve positive and negative selection using markers of interest. For example, agents can be used to recognize stem cell markers, for instance labeled antibodies that recognize and bind to BCRP1 protein on ovarian cancer stem cells can be used to separate and isolate the ovarian cancer stem cells from non-stem cell ovarian cancer cells using fluorescent activated cell sorting (FACS), panning methods, magnetic particle selection, particle sorter selection and other method known to persons skilled in the art, including density separation (Xu et al. (2002) Circ. Res. 91:501; U.S. patent application Ser. No. 20030022367); separation based on physical properties (Doevendans et al. (2000) J. Mol. Cell. Cardiol. 32:839-851). Alternatively, genetic selection methods can be used, where an ovarian cancer cell can be genetically modified to express a reporter protein operatively linked to a tissue-specific promoter and/or a specific gene promoter, therefore the expression of the reporter can be used for positive selection methods to isolate and enrich the desired cell, for example ovarian cancer stem cell. For example, a fluorescent reporter protein can be expressed in the desired stem cell by genetic modification to operatively link the marker protein to the promoter expressed in a desired stem cell (Klug et al. (1996) J. Clin. Invest. 98:216-224; U.S. Pat. No. 6,737,054). Other means of positive selection include drug selection, for instance such as described by Klug et al, supra, involving enrichment of desired cells by density gradient centrifugation. Negative selection can be performed and selecting and removing cells with undesired markers or characteristics, for example cells that do not express BCRP1 or non-stem cell markers for example fibroblast markers, epithelial cell markers etc.

One variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996). Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994. TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct). To minimize errors and the effect of sample-to-sample variation, RT-PCR is usually performed using an internal standard. The ideal internal standard is expressed at a relatively constant level among different tissues, and is unaffected by the experimental treatment. RNAs frequently used to normalize patterns of gene expression are mRNAs for the housekeeping genes glyceraldehyde-3-phosphate-dehydrogenase (GAPDH) and β-actin.

In some embodiments, the systems for real-time PCR uses, for example, Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes.

Other methods for detecting the expression of genes are well known in the art and disclosed in patent application WO2000/04194, incorporated herein by reference. In an exemplary method, the method comprises amplifying a segment of DNA or RNA (generally after converting the RNA to cDNA) spanning one or more known isoforms of BCRP1 gene sequences. This amplified segment is then subjected to a detection method, such as signal detection, for example fluorescence, enzymatic etc. and/or polyacrylamide gel electrophoresis. The analysis of the PCR products by quantitative mean of the test biological sample to a control sample indicates the presence or absence of the marker gene in the cardiovascular stem cell sample. This analysis may also be performed by established methods such as quantitative RT-PCR (qRT-PCR).

The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008. Other methods for detecting expression of the marker genes by analyzing RNA expression comprise methods, for example but not limited to, Northern blot, RNA protection assay, hybridization methodology and microarray assay etc. Such methods are well known in the art and are encompassed for use in this invention.

Primers specific for PCR application can be designed to recognize nucleic acid sequence encoding BCRP1, are well known in the art. For purposes of a non-limiting example, the nucleic acid sequence encoding human BCRP1 can be identified by accession number: NM_004827 and AF103796 (SEQ ID NO: 19). BCRP1 is also known as aliases; ATP-binding cassette, sub-family G member 2 (ABCG2), EST157481, MXR, BCRP, ABCP and CDw338.

Any suitable immunoassay format known in the art and as described herein can be used to detect the presence of and/or quantify the amount of BCRP1 expression by the ovarian cancer stem cell. In some embodiments, the invention provides methods of screening for the BCRP1 expression by immunohistochemical or immunocytochemical methods, typically termed immunohistochemistry ("IHC") and immunocytochemistry ("ICC") techniques. IHC is the application of immunochemistry on samples of tissue, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically recognize and bind to target molecules on the inside or on the surface of cells, for example BCRP1. In some embodiments, the antibody contains a reporter or marker that will catalyze a biochemical reaction, and thereby bring about a change color, upon encountering the targeted molecules. In some instances, signal amplification may be integrated into the particular protocol, wherein a secondary antibody, that includes the marker stain, follows the application of a primary specific antibody. In such embodiments, the marker is an enzyme, and a color change occurs in the presence and after catalysis of a substrate for that enzyme.

Immunohistochemical assays are known to those of skill in the art (e.g., see Jalkanen, et al., J. Cell. Biol. 101:976-985 (1985); Jalkanen, et al., J. Cell. Biol. 105:3087-3096 (1987). Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold. Spring Harbor Laboratory Press, Cold Spring Harbor, N.Y. (1988). In general, examples of antibodies useful in the present invention include anti-BCRP1. Such antibodies are commercially available and can be purchased, for example, from Sigma, US Biologicals, Novus Biologicals, MBL, Millipore, santa Cruz biotechnology and other commercially available sources. In some embodiments, any antibodies that recognize BCRP1 can be used by any persons skilled in the art, and from any commercial source. Alternatively, antibodies (monoclonal and polyclonal) can easily produced by methods known to person skilled in the art. In alternative embodiments, the antibody can be an antibody fragment, an analogue or variant of an antibody. Anti-BCRP1 antibodies are commercially available, for example but not limited to from Sigma, US Biologicals, Novus Biologicals, Santa Cruz Biotechnology, Molecular Biology Laboratories, Becton and Dickenson and Millipore.

In some embodiments, where BCRP1 is detected by immunohistochemistry, the ovarian cancer cells can be fixed by a suitable fixing agent such as alcohol, acetone, and paraformaldehyde prior to, during or after being reacted with (or probed) with an antibody. Conventional methods for immunohistochemistry are described in Harlow and Lane (Eds) (1988) In "Antibodies A Laboratory Manual", Cold Spring Harbor Press, Cold Spring Harbor, N.Y.; Ausbel et al (Eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, breast aspirates, pleural fluid, urine and the like. For direct labeling techniques, a labeled antibody is utilized. For indirect labeling techniques, the sample is further reacted with a labeled substance. Alternatively, immunocytochemistry may be utilized. In general, cells are obtained from a patient and fixed by a suitable fixing agent such as alcohol, acetone, and paraformaldehyde, prior to, during or after being reacted with (or probed) with an antibody. Methods of immunocytological staining of biological samples, including human samples, are known to those of skill in the art and described, for example, in Brauer et al., 2001 (FASEB J, 15, 2689-2701), Smith Swintosky et al., 1997. Immunological methods of the present invention are advantageous because they require only small quantities of biological material, such as a small quantity of cardiovascular stem cells. Such methods may be done at the cellular level and thereby necessitate a minimum of one cell.

In some embodiments, cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

In a different embodiment, antibodies and antibody derivatives or fragments thereof that are used to identify markers on ovarian cancer cells, for example antibodies that recognize BCRP1 protein can bind to at least one epitope or more epitopes and can be detected using analytical techniques, such as by protein dot blots, sodium dodecyl sulfate polyacrylamide gel electrophoresis (SDS-PAGE), or any other gel system that separates proteins, with subsequent visualization of the marker (such as Western blots), gel filtration, affinity column purification; morphologically, such as fluorescent-activated cell sorting (FACS), staining with dyes that have a specific reaction with a marker molecule (such as ruthenium red and extracellular matrix molecules), specific morphological characteristics; and biochemically, such as assaying for an enzymatic product or intermediate, or the overall composition of a cell, such as the ratio of protein to lipid, or lipid to sugar, or even the ratio of two specific lipids to each other, or polysaccharides. If such a marker is a morphological and/or functional trait or characteristic, suitable methods include visual inspection using, for example, the unaided eye, a stereomicroscope, a dissecting microscope, a confocal microscope, or an electron microscope are encompassed for use in the invention. The invention also contemplates methods of analyzing the progressive or terminal differentiation of a cell employing a single marker, as well as any combination of molecular and/or non-molecular markers.

Various methods can be utilized for quantifying the presence of the BCRP1 protein or nucleic acid expression. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12): 1305-12; and Chen et al. (1998) Genomics 51(3):313-24, for examples.

Also encompassed for use in this invention, is the isolation and enrichment of a population of ovarian cancer stem cells as disclosed herein by the use of introduced reporter genes that aids with the identification of ovarian cancer stem cells and/or somatic ovarian stem cells as disclosed herein, for example coelomic ovarian stem cell populations, subcoelomic/stromal ovarian stem cell populations and periphilar medullary ovarian stem cell populations. As an exemplary example only, ovarian cancer stem cells can be genetically engineered to express a construct comprising a reporter gene which can be used for selection and identification purposes. For example, the ovarian cell is genetically modified to comprise a reporter gene, for example but not limited to a fluorescent protein, enzyme or resistance gene, which is operatively linked to a BCRP1 promoter or fragment thereof. In such an embodiment, when the cell expresses the gene to which the reporter of interest is operatively linked, for example when the cell expresses BCRP1, it will expresses the reporter gene, for example the enzyme, fluorescent protein or resistance gene. Cells that express the reporter gene can be readily detected and in some embodiments positively selected for cells comprising the reporter gene or the gene product of the reporter gene. Other reporter genes that can be used include fluorescent proteins, luciferase, alkaline phosphatase, lacZ, or CAT.

In another embodiment encompasses methods for the identification, isolation and enrichment as well as distinguishing between ovarian cancer stem cells and coelomic ovarian stem cells, the methods comprising using conventional methods of using reporter genes operatively linked to the promoters of EpCam or homologues or variants thereof. In such embodiments, cells that express the surface markers cytokeratin-8, β-catenin and E-cadherin and also express the EpCam surface marker protein, the cells will also express the reporter gene operatively linked to the promoter of EpCam, and the expression of the reporter gene can be used to isolate, identity and enrich for a population of ovarian cancer stem cells, whereas lack of expression of the reporter gene can be used to isolate, identity and enrich for a population of somatic ovarian stem cells such as coelomic ovarian stem cells. In alternative embodiments, a different reporter gene can be expressed when the EpCam is not expressed, which can be used to identify and enrich for somatic ovarian stem cells such as coelomic ovarian stem cells. In some embodiments, a reporter gene is expressed when EpCam is expressed which can be used to isolate, identity and enrich a population of ovarian cancer stem cells, and a different reporter gene such as a different fluorescent reporter gene can be expressed when the EpCam is not expressed, which can be used to identify and enrich for somatic ovarian stem cells such as coelomic ovarian stem cells, thus enabling enrichment of populations of somatic ovarian stem cells and ovarian cancer stem cells within different or the same starting population of cells.

In some embodiments, the cells expressing these reporters could be easily purified by FACS, antibody affinity capture, magnetic separation, or a combination thereof. The purified or substantially pure reporter-expressing cells can be used for genomic analysis by techniques such as microarray hybridization, SAGE, MPSS, or proteomic analysis to identify more markers that characterize the ovarian cancer stem cells. These methods can be used to identify genes expressed by ovarian cancer stem cells and genes important in the self-renewal property of ovarian cancer stem cells. In other embodiments, the reporter gene can be a fluorescent protein, for examples but not limited to; green fluorescent protein (GFP); green fluorescent-like protein (GFP-like); yellow fluorescent protein (YFP); blue fluorescent protein (BFP); enhanced green fluorescent protein (EGFP); enhanced blue fluorescent protein (EBFP); cyan fluorescent protein (CFP); enhanced cyan fluorescent protein (ECFP); red fluorescent protein (dsRED); and modifications and fragments thereof.

In some embodiments, methods to remove unwanted cells are encompassed, by removing unwanted cells by negative selection. For example, unwanted antibody-labeled cells are removed by methods known in the art, such as labeling a cell population with an antibody or a cocktail of antibodies, to a cell surface protein and separation by FACS or magnetic colloids. In an alternative embodiment, the reporter gene may be used to negatively select non-desired cells, for example a reporter gene is expressed by cells not expressing BCRP1 and the reporter gene encodes a cytotoxic protein in cells that are not desired. In such an embodiment, the reporter gene is operatively linked to a regulatory sequence of a gene normally expressed in the cells with undesirable phenotype.

Methods of Treatment

The present invention relates generally to a method of preventing and/or treating ovarian cancer in a subject, where the ovarian cancer comprises ovarian cancer stem cells as identified by the methods as disclosed herein. In some embodiments, the methods of the present invention comprise administration of an effective amount of MIS or a derivative or fragment thereof to a subject with ovarian cancer, where cancer comprises ovarian cancer stem cells. For example, an effective amount of MIS or a homologue or variant or analogue thereof is administered to a subject with ovarian cancer, wherein the subject is identified to have ovarian cancer comprising ovarian cancer stem cells using the methods as disclosed herein. In some embodiments, administration of MIS to a subject is a MIS protein, for example as disclosed in U.S. Pat. Nos. 5,661,125 and 6,673,352 which are specifically incorporated herein in their entirety by reference. Accordingly, by using the methods of the present invention, one can treat and/or prevent the progression or occurrence of ovarian cancer in a subject wherein the ovarian cancer comprises ovarian cancer stem cells. In some embodiments, the cancer is recurrent ovarian cancer. In some embodiments, where the subject is identified as having ovarian cancer comprising ovarian cancer stem cells, the subject is administered a pharmaceutical composition comprising a BCRP1 inhibitor, for example a verapamil. In some embodiments, where the subject is identified as having ovarian cancer comprising ovarian cancer stem cells, the subject is administered a pharmaceutical composition comprising a BCRP1 inhibitor and/or MIS or a derivative or fragment or variant thereof.

Inhibitors of BCRP1 are commonly known by one of ordinary skill in the art, for example but not limited to verapamil, Reserpine, CI1033, GF120918, FTC, ko138, P-gp and analogues and derivatives thereof, as disclosed in Allen et al, Mol Cancer Therapeutics, 2002; 1:427-434, which is incorporated herein in its entirety by reference. The chemical structures of GF120918, FTC (Furmitremorgin) and ko138 are as follows:

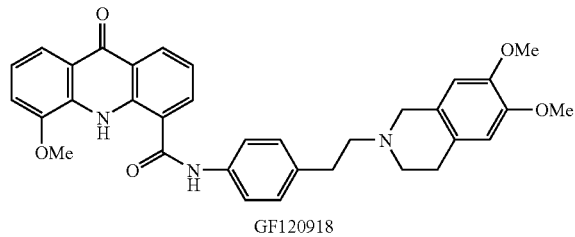

GF120918

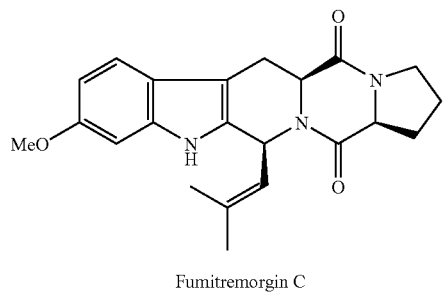

Fumitremorgin C

-continued

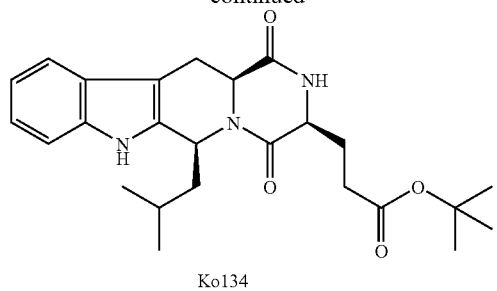

Ko134

In some embodiments, the MIS is a MIS protein, for example recombinant human MIS (rhMIS). In such embodiments, MIS or rhMIS can be prepared and administered, in any form, by any method known by persons of ordinary skill in the art, for example as disclosed in International Patent Application WO92/18152 and European Patent EP584287 and also disclosed in patent Applications WO94/00133 and EP221761, which are incorporated herein in their entity by reference.

In certain embodiments, the endogenous compounds are isolated and/or purified or substantially purified by one or more purification methods described herein or known by those skilled in the art. Generally, the purities are at least 90%, in particular 95% and often greater than 99%.

As used herein, the term ovarian cancer is use to refer to, for example cervical cancer and ovarian cancer. In some embodiments, the ovarian cancer is vulvar epidermal carcinoma, cervical carcinoma, endometrial edenocarinaoma or ovarian adenocarcinoma.

In another embodiment, the methods as disclosed herein also contemplates the administration of MIS to a subject identified with ovarian cancer comprising cancer stem cells in conjunction with other therapies such as conventional chemotherapy, radiotherapy, hormone therapy, immunotherapy, thermotherapy and surgery directed against solid tumors and for control of establishment of metastases. The administration of the compounds described herein is typically conducted prior to and/or at the same time and/or after such additional therapies, although it is also encompassed within the present invention to administer a pharmaceutical composition comprising, for example MIS or a variant or derivative thereof, and/or an inhibitor of BCRP1 at the same time or at times where the ovarian tumor tissue will be responding to a toxic assault by inducing angiogenesis to recover by the provision of a blood supply and nutrients to the tumor tissue. In addition, the pharmaceutical compositions of the invention for the treatment of ovarian cancer comprising ovarian cancer stem cells can be administrated prophylatically and/or before the development of a tumor, if the subject has been identified as to have a risk of developing cancer, for example to subjects that are positive for biomarkers of ovarian cancer cells or tumors. Insofar as the present methods apply to inhibition of ovarian cancer stem cells, the methods can also apply to inhibition of ovarian cancer tissue growth, to inhibition of ovarian cancer metastases formation, and to regression of established ovarian cancer tumors.

The effective amount may vary depending upon criteria such as the age, weight, physical condition, past medical history, and sensitivity of the recipient. The effective amount will also vary depending on whether administration is oral, intravenous, intramuscular, subcutaneous, local, or by direct application to the tumor. In the case of direct tumor application, it is preferable that a final serum concentration of at least 0.1 nM, preferably about 0.1-1.0 nM, of MIS be achieved. Effective individual dosage through the additionally named means of administration can be readily determined by methods well known to those of ordinary skill in the art. For example, using the size ratio calculation as detailed above, one of ordinary skill in the art can determine optimal dosage levels for any means of administration. In treating a patient, it is preferable to achieve a serum level of at least 10 ng/ml of MIS.

Compositions containing MIS or its functional derivatives may be administered orally, intravenously, intramuscularly, subcutaneously, or locally. Additional pharmaceutical methods may be employed to control the duration of action. Controlled release preparations may be achieved by the use of polymers to complex or adsorb MIS or its functional derivatives. The controlled delivery may be exercised by selecting appropriate macromolecules (for example polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate MIS into particles of a polymeric material such as polyesters, polyamino acids, hydrogels, poly(lactic acid) or ethylene vinyl acetate copolymers. Alternatively, instead of incorporating MIS into these polymeric particles, it is possible to entrap MIS in microcapsules prepared, for example, by coacervation techniques or by interfacial polymerization, for example, hydroxymethylcellulose or gelatin microcapsules and poly(methylmethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences, supra (1980).

Pharmaceutical compositions which include the proteolytically cleaved MIS protein fragments of this invention can also include chemotherapeutic agents which are known to inhibit tumor growth in a human or animal. The chemotherapeutic agent included in this composition can be directed to any specific neoplastic disease. Such agents are described in Goodman and Gilman's The Pharmacological Basis of Therapeutics, 8th Ed., Pergamon Press, New York, N.Y., 1985. It is preferred, however, that the chemotherapeutic agent inhibits the growth of the tumors of this invention.

In some embodiments the subject identified to have ovarian cancer comprising ovarian cancer stem cells can be administered other therapies, for example but not limited to chemotherapeutic agents. In some embodiments, the chemotherapeutic agent is a BCRP1 protein inhibitor, for example but not limited to verapamil.

In alternative embodiments, the subject is administered other chemotherapeutic agents, for example paxcitaxal, chemotherapeutic agents are paclitaxel, cisplatin, doxorubicin, rapamycin. Also included as chemotherapeutic agents in the pharmaceutical compositions of this invention are nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon; platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

It is to be understood that the use of the term "equivalent effective amount" does not necessarily mean an equivalent weight or volume quantity, but represents the quantity of MIS that offers an equal inhibition to tumor growth. This may have to be evaluated on a patient by patient case, but can be determined, for example, by comparing quantities that achieve equal size reduction ratios as defined above. Typically, chemotherapeutic agents which can be combined with MIS for treatment of the tumors of this invention will be effective between about 0.001 and 10.0 mg/kg body weight of the patient. Administration of the combination of MIS and chemotherapeutic agent can be accomplished in the same manner as administration of the MIS alone.

In some embodiments, the methods as disclosed herein provide for the parenteral and oral administration of the compounds of the present invention, in combination with other pharmaceutical compositions to subjects in need of such treatment. Parenteral administration includes, but is not limited to, intravenous (IV), intramuscular (IM), subcutaneous (SC), intraperitoneal (IP), intranasal, and inhalant routes. In the method of the present invention, the resolvins and/or protectins or analogs thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the subject. In general, a dose that is administered by subcutaneous injection will be greater than the therapeutically-equivalent dose given intravenously or intramuscularly.

The methods as disclose herein for treating ovarian cancer comprising ovarian cancer stem cells comprising contacting a tissue in which tumor is occurring, or is at risk for occurring, with the compositions of the present invention comprising a therapeutically effective amount of MIS or derivatives or analogues thereof.

In some embodiments, the subject treated by the methods of the present invention in its many embodiments is a human subject, although it is to be understood that the principles of the invention indicate that the invention is effective with respect to all mammals. In this context, a mammal is understood to include any mammalian species in which treatment of diseases associated with cancer or a proliferative-related disorder is desirable, particularly agricultural and domestic mammalian species, as well as transgenic animals.

Administration of Pharmaceutical Compositions

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

After formulation with an appropriate pharmaceutically acceptable carrier in a desired dosage, the pharmaceutical compositions of this invention can be administered to a subject. The pharmaceutical compositions of this invention can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

In general, a suitable daily dose of a compound of the invention will be that amount of the compound which is the lowest dose effective to produce a therapeutic effect. Such an effective dose will generally depend upon the factors described above. If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or derivatives thereof. A "therapeutically effective amount" refers to an amount effective, at dosages and for periods of time necessary, to achieve the desired therapeutic result, e.g., a diminishment or prevention of effects associated with ovarian cancer, wherein the cancer comprises ovarian cancer stem cells. A therapeutically effective amount of MIS of the present invention or derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylatically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound and the particular therapeutic or prophylactic effect to be achieved, and (b) the limitations inherent in the art of compounding such an active compound for the treatment of sensitivity in subjects.

The therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit cell proliferation in a subject suffering from a proliferative disorder, for example cancer. In some embodiments, the therapeutically effective amount is sufficient to eliminate the proliferative cells, for example eliminate the cancer cells and/or tumor in a subject suffering cancer and/or a proliferative disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Pharmaceutical Compositions

In another embodiment of the invention, pharmaceutical compositions containing one or more compounds of this invention are disclosed. For purpose of administration, in some embodiments MIS or derivatives, fragments or variants or analogues thereof and/or inhibitors of BCRP1 are formulated as a pharmaceutical composition. Pharmaceutical compositions of the present invention comprise a compound of this invention and a pharmaceutically acceptable carrier, wherein the compound is present in the composition in an amount which is effective to treat the condition of interest.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in *Remington's Pharmaceutical Sciences*, Gennaro, Ed., Mack Publishing Co., Easton, Pa. 1990.

While it is possible to administered MIS and derivatives and fragments alone and/or inhibitors of BCRP1 alone, it is preferable to administer MIS and/or inhibitors of BCRP1 as pharmaceutical compositions.

Formulations of the invention can be prepared by a number or means known to persons skilled in the art. In some embodiments the formulations can be prepared by combining (i) MIS and derivatives fragments, variants and analogues thereof, and/or inhibitors of BCRP1 in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a co-solvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more of the compounds of the present invention, and/or their derivatives thereof for oral or subcutaneous administration.

In certain embodiments, the compounds of the present invention, for MIS or derivatives or variants thereof are administered to a subject as a pharmaceutical composition with a pharmaceutically acceptable carrier. In certain embodiments, these pharmaceutical compositions optionally further comprise one or more additional therapeutic agents. In certain embodiments, the additional therapeutic agent or agents are anti-cancer agents. In some embodiments, the therapeutic agents are chemotherapeutic agents, for example but not limited to, cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective and encompassed for use in the methods of the present invention. Of course, other chemotherapeutic agents which are known to those of ordinary skill in the art can readily be substituted as this list should not be considered exhaustive or limiting.

In some embodiments the pharmaceutical composition comprises MIS and/or derivatives thereof, alone or in any plurality of combinations. In other embodiments, the pharmaceutical compositions optionally further comprise one or more additional therapeutic agents including but not limited to paxicital, paxicital derivatives, cisplatin and cisplatin derivative, and interferons.

In some embodiments, the methods of the present invention are directed to use of MIS and variants and derivatives thereof with other therapeutic agents, for example chemotherapy agents, wherein the chemotherapy agents, for example verapamil.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term pharmaceutically acceptable salts, esters, amides, and prodrugs as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, pharmaceutically acceptable salts or prodrugs are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use. These compounds include the zwitterionic forms, where possible, of compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds that are rapidly transformed in vivo to yield the compounds of the invention, for example MIS and/or BCRP inhibitor as disclosed herein, by hydrolysis in blood. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound or to alter other characteristics or properties of a compound. By virtue of knowledge of pharmacodynamic processes and drug metabolism in vivo, once a pharmaceutically active compound is identified, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In other embodiments of the present invention, MIS and derivatives thereof and/or BCRP inhibitors are conjugated or covalently attached to another targeting agent to increase the specificity of MIS and derivatives thereof and/or BCRP inhibitors targeting the cell, for example an ovarian cancer stem cell. Targeting agents can include, for example without limitation, antibodies, cytokines and receptor ligands. In some embodiments, the targeting agent is overexpressed on the cells to be targeted, for example the cancer cells as compared to normal cells. In alternative embodiments, the MIS and derivatives thereof and/or BCRP inhibitors can be conjugated or covalently attached to compounds that elicit an immune response, such as for example but without limitation, cytokines.

In some embodiments, MIS and derivatives thereof of the present invention can be conjugated to, by covalent linkage or any other means, to another agent, for example chemotherapy agents for example BCRP1 inhibitors. In some embodiments, MIS and derivatives thereof, and/or BCRP inhibitors of the present invention can be conjugated to a targeting moiety, for example an ovarian cancer cell targeting moiety to target the MIS and/or BCRP inhibitors to ovarian cancer stem cell. Such targeting moieties and methods are well known by persons of ordinary skill in the art and are encompassed for use in the methods of the present invention. In some embodiments, the targeting moiety is a moiety that interacts with BCRP1 present on the exterior of ovarian cancer stem cells. In some embodiments, the conjugation may be a permanent or reversible conjugation.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, pharmaceutical compositions comprising the resolvins and protectins of the invention for the administration of angiogenesis may be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Remington's Pharmaceutical sciences Ed. Germany, Merk Publishing, Easton, Pa., 1995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

Uses of the Ovarian Cancer Stem Cells

In some embodiments, ovarian cancer stem cells and somatic ovarian stem cells as disclosed herein can be isolated and enriched using the methods as disclosed herein, for example purified by FACS, antibody affinity capture, magnetic separation, or a combination thereof using the surface markers as disclosed herein, such as, but not limited to, BCRP1 expression, cytokeratin-8, β-catenin and E-cadherin, EpCam, cKIT, αSMA, PDGFRb, NG2, CD31, CD44, CD105, SF-1, GATA-4 and MISRII expression and/or lipophilic dye exclusion. The purified or substantially pure ovarian cancer stem cells and/or somatic ovarian stem cells can be used for genomic analysis by techniques such as microarray hybridization, SAGE, MPSS, or proteomic analysis to identify more markers that characterize the ovarian cancer stem cell populations and/or somatic ovarian stem cell populations.

One aspect of the present invention relates to an assay to identify agents that reduce the self-renewal capacity of an ovarian cancer stem cell as compared to somatic ovarian stem cells such as coelomic ovarian stem cell populations and/or subcoelomic/stromal ovarian stem cell populations and periphilar medullary ovarian stem cell populations. In some embodiments, the assay involves contacting an ovarian cancer stem cell with an agent, and measuring the proliferation of the ovarian cancer cell, whereby an agent that decreases the proliferation as compared to a reference agent or absence of an agent identifies an agent that inhibits the self-renewal capacity of the ovarian cancer stem cell. Such an agent can be used for development of therapies for the treatment of ovarian cancer. In some embodiments, the assay can encompass comparing the results of the rate of proliferation of a somatic ovarian stem population, for example a coelomic ovarian stem cell population in the presence of the same agent, where an agent useful for selection as a therapy for the treatment of ovarian cancer in a subject is an agent that inhibits the self-renewal capacity of a population of ovarian cancer stems to a greater extent, for example greater than 10%, or greater than about 20%, or greater than 30% as compared to the ability of the agent to inhibit the self-renewal capacity of a population of somatic ovarian stem cells, for example a coelomic ovarian stem cell population.

Also encompassed in the present invention is use of the ovarian cancer stem cells and somatic ovarian stem cells as disclosed herein in assays to identify agents which kill and/or decrease the rate of proliferation of ovarian cancer stem cells. In some embodiments, such an assay can comprising both a population of ovarian cancer stem cells and a population of somatic ovarian stem cells, for example coelomic ovarian stem cell and/or subcoelomic/stromal ovarian stem cells and/or periphilar medullary ovarian stem cells, but preferably coelomic ovarian stem cells and adding to the media of the population of ovarian cancer stem cells and to the population of somatic ovarian stem cells one or more of the same agents. Once can measure and compare the rate of proliferation of the population of ovarian cancer stem cells and the population of somatic ovarian stem cells using the methods as disclosed herein, for example the MTT assay or CFU assay, and an agent identified to decrease the rate of proliferation and/or attenuate proliferation by about 10%, or about 20% or about 30% or greater than 30% and/or kill about 10% or about 20% or about 30% or greater than 30% of the population of ovarian cancer stem cells as compared to a population of somatic ovarian stem cells identifies an agent that is useful for a therapy for the treatment of ovarian cancer. Effectively, the assay as disclosed herein can be used to identify agents that selectively inhibit the ovarian cancer stem cells as compared to coelomic ovarian stem cell population. Agents useful in such an embodiment can be any agent as disclosed herein under the term "agent" in the definitions section, and can be for example nucleic acid agents, such as RNAi agents (RNA interference agents), nucleic acid analogues, small molecules, proteins, peptiomimetics, antibodies, peptides, aptamers, ribozymes, and variants, analogues and fragments thereof.

In further embodiments, the ovarian cancer stem cells and somatic ovarian stem cells identified using the methods as disclosed herein can be used in assay to for the study and understanding of signalling pathways of cancer stem cells. The use of ovarian cancer stem cell and somatic ovarian stem cells of the present invention is useful to aid the development of therapeutic applications for ovarian cancers. The use of such ovarian cancer stem cells identified using the methods as disclosed herein enable the study of ovarian cancers. For example, the ovarian cancer stem cells can be used for generating animal models of ovarian cancer as described in the Examples herein, which can be used for an assay to test for therapeutic agents that inhibit the proliferation of ovarian cancer stem cells. Such a model us also useful in aiding the understanding of ovarian cancer stem cells in the development of ovarian cancer.

The ovarian cancer stem cells can be used to identify additional markers that characterize them as ovarian cancer stem cells as compared to non-stem ovarian cancer cells and/or somatic ovarian stem cells, such as coelomic ovarian stem cell populations and/or subcoelomic/stromal ovarian stem cell populations and periphilar medullary ovarian stem cell populations. Such markers can be cell-surface markers or surface markers or other markers, for example mRNA or protein markers intracellular within the cell. Such markers can be used as additional agents in the diagnosis of ovarian cancer stem cells in subjects with ovarian cancers.

In further embodiments, the ovarian cancer stem cells and somatic ovarian stem cells as disclosed herein can be used to prepare antibodies that are specific markers of ovarian cancer stem cells and somatic ovarian stem cells as disclosed herein. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

The antibodies in turn can be used as diagnostic applications to identify a subject with ovarian cancer comprising ovarian cancer stem cells, or alternatively, antibodies can be used as therapeutic agents to prevent the proliferation and/or kill the ovarian cancer stem cells.

In another embodiment, the ovarian cancer stem cells and somatic ovarian stem cells as disclosed herein can be used to prepare a cDNA library of relatively uncontaminated with cDNAs that are preferentially expressed in ovarian cancer stem cells as compared to somatic ovarian stem cells and/or non-stem cells ovarian cancer cells. For example, ovarian cancer stem cells and/or and somatic ovarian stem cells are collected and then mRNA is prepared from the pellet by standard techniques (Sambrook et al., supra). After reverse transcribing the cDNA, the preparation can be subtracted with cDNA from, for example non-stem cell ovarian cancer cells or non-cancer ovarian cells in a subtraction cDNA library procedure. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the molecular size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680. Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505. Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined. Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes. Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992. General methods in molecular and cellular biochemistry can also be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Having generally described this invention, the same will become more readily understood by reference to the following specific examples which are included herein for purposes of illustration only and are not intended to be limiting unless otherwise specified.

EXAMPLES

The examples presented herein relate to the methods of prevention and/or treatment of ovarian cancer, for example in subjects that have ovarian cancer comprising ovarian cancer stem cells. Methods as disclosed herein provide treatment of ovarian cancer by targeting ovarian cancer stem cells, in particular by targeting ovarian cancer stem cells with MIS or derivatives or variants thereof and/or inhibitors of BCRP1. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Flow Cytometry.

Flow cytometry was performed in the Department of Pathology and Center for Regenerative Medicine Flow Cytometry Laboratory according to their published protocols (36). Mouse and human ovarian cancer SP sorting and immunophenotyping were performed as described in *Supporting Methods*, which is published as supporting information on the PNAS web site. When testing SPs for multidrug resistance-like BCRP1 sensitivity, verapamil (25-50 µg/ml; Sigma) was also added.

For cell cycle analysis, MOVCAR 7 cells were harvested, sorted for Hoechst$^{High}$ NSP, Hoechst$^{Mid}$, and Hoechst$^{Low}$ SP cells, and fixed with 70% ethanol for 24 h. Cells were washed in PBS, stained with 20 µg/ml propidium iodide and 1 mg/ml RNase (Type 10A; Sigma), and collected on a Life Sciences Research flow cytometer configured with CELLQUEST PRO software (BD Biosciences, Franklin Lakes, N.J.).

Side Population Sorting.

Mouse and human ovarian cancer single cell suspensions were stained with 5 µg/ml of the DNA intercalating Hoechst 33342 dye for 90 min at 37° C., washed, and resuspended in PBS containing 2% FCS and 1 mM Hepes. Before cell sorting, 2 µg/ml propidium iodide (Sigma) was added to exclude nonviable cells demonstrating uptake. SP cells were identified and electronically gated on a Digital Vantage cell sorter (Becton Dickinson) after excitation of the Hoechst dye with 150 mW of 350 nm UV light. SP fluorescence emissions were directed toward a 610-nm dichroic filter and captured simultaneously through both a blue (450-nm) band-pass and a red (675-nm) long-pass filter on a linearly amplified fluorescence scale.

Surface Marker Antibodies.

Immunophenotyping of mouse and human cells was performed with titered fluorescein isothiocyanate (FITC), phycoerythrin (PE), or allophycocyanin mAb conjugates of CD24 (binds P-selectin), CD31 (PECAM-1, endothelial cells), CD34 [sialomucin; hematopoietic stem cells (HSCs), adhesion], CD45 (leukocyte common antigen), CD44 (HCAM; binds hyaluronic acid), CD90 (Thy1.1; HSC, neuron, myofibroblast differentiation), c-kit (CD117; HSCs, mast cells), Sca-1 (Ly-6A/E; hematopoietic progenitors, mast cells), and CD 105 (endoglin; endothelial, type III receptor for TGF-B) purchased from Becton Dickinson. Human cancer cells were also analyzed for the presence of epithelial-specific antigen (ESA/Ep-CAM, epithelial breast cancer progenitor cells), Lab Vision Corporation Clone 323/A3.

Cell Lines and Culture.

Mouse ovarian cancer cell lines, MOVCAR 7 and 8, were developed by D.C. by using the MISRII promoter to drive the SV40 T antigen (19). The OVCAR 3 and OVCAR 8 human ovarian cancer cell lines were developed by Thomas Hamilton (Fox Chase Cancer Center) (37). The 4306 cell line was developed by D.M.D. from conditional LSL-K-ras$^{G12D/+}$/Pten$^{loxP/loxP}$ mice after infection of ovarian surface epithelium with adenovirus expressing Cre recombinase. These mice developed invasive endometrioid ovarian cancers 7 weeks after infection, and the 4306 cell line was established from ascites cells (20). IGROV-1 and SK-OV-3 were obtained from American Type Culture Collection (ATCC). Cell lines were maintained in 4% female FBS (MIS-free) and DMEM with added L-glutamine, 1% penicillin/streptomycin, and 1% insulin-transferrin-selenium (ITS; GIBCO) at 37° C., 5% $CO_2$, in T175 flasks within a humidified chamber. All cells recovered from sorting were grown in the same media.

Human Primary Ascites Cell Isolation.

Primary ascites cells were analyzed from five stage III ovarian cancer patients and one (AC-01) patient with recurrent ascites, who ranged in age from 54 to 71 years (mean, 62.2 years). The study was approved by the Human Studies Committee of Massachusetts General Hospital (Protocol No. FWA0003136), and consent was obtained from each patient on the Gynecology Oncology Service at the time of outpatient paracentesis or before surgery. Ascites harvested at laparotomy or ultrasound-guided paracentesis were placed on ice, centrifuged to isolate the cellular component, and resuspended in media. Erythrocytes were lysed, and cells were cultured in RPMI with 10% female FBS, 1% penicillin/streptomycin, and 1% fungizome. Cells were analyzed by flow cytometry within 96 h for the presence of an SP and surface markers.

Immunostaining of Cultured Cells.

Anti-MISRII rabbit polyclonal antibodies (153p/MISRII) were developed for Western blot analysis in the Pediatric Surgical Research Laboratories (35). Immunofluorescence was performed on MOVCAR 7 and 4306 cells by using 153p as described (25). Images were obtained by using either epifluorescent (Nikon Eclipse E400 microscope, SPOT camera, and SPOT ADVANCE software) or confocal microscopy (Leica TCS NT confocal microscope, CONFOCAL software Version 2.5 Build 1227, and krypton 568-nm laser; Leica, Deerfield, Ill.).

For BCRP1 immunostaining, cells were double-labeled in suspension with Hoechst 33342 and BCRP1 antibody as described in ref 5. Briefly, for BCRP1 immunostaining, cells were double-labeled in suspension with Hoechst 33342 and BCRP antibody (Seigel, G. M., Campbell, L. M., Narayan, M. & Gonzalez-Fernandez, F. (2005) *Mol. Vis.* 11, 729-737). Cells ($2 \times 10^6$) were centrifuged for 5 min, resuspended in 4-ml DMEM with 2% FCS, stained with Hoechst 33342 dye (Molecular Probes) at 5 µg/ml, incubated at 37° C. for 90 min, washed twice in PBS, resuspended in 200 µPBS plus 1% FCS, then divided into two tubes. One tube received BCRP1 antibody (1:20, Clone BX-34; Abcam, Inc., Cambridge, Mass.), and the other received isotype control antibody. Samples were incubated for 1 h at room temperature, washed twice in PBS, resuspended in 100 µl of Alexa Fluor 555 conjugated anti-rat IgG (Molecular Probes) at a dilution of 1:800, incubated for 1 h at room temperature, washed twice, centrifuged, resuspended in 20 µl PBS plus 1% FCS, pipetted onto a slide, and coverslipped for microscopic viewing.

Reverse Transcriptase PCR.

Total RNA from MOVCAR 7 and 4306 SP and NSP cells was extracted by using the Qiagen (Valencia, Calif.) RNeasy Mini Kit (catalog no. 74104) according to the manufacturer's instructions, and 0.5 µg of RNA was reverse transcribed into cDNA by using Superscript II reverse transcriptase as directed by the manufacturer (Invitrogen). All RT-PCRs were run for 30 cycles with an annealing temperature of 57° C. and separated on 2% agarose gels. Mouse PCR primers are as in Table 5.

TABLE 5

Mouse PCR Primers

| Protein | Forward Primer | Reverse Primer |
|---|---|---|
| Bcrp1 | CCATAGCCACAGGCCAAAGT (SEQ ID NO: 1) | GGGCCACATGATTCTTCCAC (SEQ ID NO:2) |
| MisrII | GCTGGTTTTTGCTGGTTTATGC (SEQ ID NO: 3) | TTTGGGGATACTTGTGCTGCCG (SEQ ID NO: 4) |
| Smad1 | TGAACTGAAGCCTCTGGAATG (SEQ ID NO: 5) | TCGTAAGCAACTGCCTGAACAC (SEQ ID NO: TC6) |
| Smad5 | AACCTGAGCCACAATGAACCG (SEQ ID NO: 7) | TCTGAACAAAGATGCTGCTGTCAC (SEQ ID NO: 8) |
| Smad8 | CAGCACTGGTGTTCTGTTGCCTAC (SEQ ID NO: 9) | CCATCTGAGTGAGCACCTTATCC (SEQ ID NO: 10) |
| Alk 2 | TTATACAATGGTCGATGGAGC (SEQ ID NO: 11) | TTCAGGCGCTCTTGATTGC (SEQ ID NO: 12) |
| Alk 3 | ATGACTCAGCTATACACTTACATCAG (SEQ ID NO: 13) | CAGGTCTTTCAGTGATTCTCC (SEQ ID NO: 14) |

Growth Inhibition by MIS In Vitro.

MTT assay was used to assess proliferation inhibition. MOVCAR 7 and 4306 cells were harvested, sorted for SPs and NSPs, and plated in the inner wells of 96-well plates at 1,000 cells per well in 200 µl of medium per well. Twenty-four hours after plating, each set of 10 wells of SP or NSP cells was treated with 10 µg/ml recombinant human MIS (25), 4 nM paclitaxel (6 mg/ml; NovaPlus, Irving, Tex.), a 4-nM doxorubicin hydrochloride injection (2 mg/ml; NovaPlus), or media alone. At day 5 or 7 of incubation, cell viability was quantified by measuring mitochondrial activity (38) on an ELISA plate reader at an absorbance of 550 nm to generate an OD proportional to the relative abundance of live cells in a given well.

Growth of MOVCAR 7 SP Cells In Vivo.

MOVCAR 7 SP and NSP cells were sorted and injected into T and B cell-deficient 6-week-old female Swiss nude mice in equal numbers (first experiment, $5.0 \times 10^5$; second experiment, $7.5 \times 10^5$) into the dorsal fat pad between the scapulae. Mice were housed in the Edwin L. Steele Laboratory for Tumor Biology under American Association for Laboratory Animal Science guidelines with the approval of the MGH Animal Care and Use Committee (protocol no. 2005N000384).

Purification of Recombinant Human MIS.

The human MIS gene was transfected into CHO cells, amplified, purified, and maintained in a dedicated facility in the Pediatric Surgical Research Laboratories for use in this study as described in ref.39. MIS levels were measured by using human MIS-specific ELISA (40). MIS was purified by a combination of lectin affinity chromatography and FPLC anion-exchange chromatography (39). The MIS purified by this method causes regression in the organ culture bioassay for MIS (41, 42).

Transgenic mice and H2Bj-GFP label and chase. H2Bj-GFP (Tumbar et al., 2004) mice purchased from Jackson Laboratories (JAX® GEMM® Strains, Stock Tg(tetO-HIST1H2BJ/GFP)47Efu/J, Stock Number 005104) were crossed with M2-Rosa26-rtTA mice, generously provided by Konrad Hochedlinger, MGH (Beard et al., 2006) for nearly ubiquitous expression of H2Bj-GFP in the presence of doxycycline and managed as previously described (Brennand et al., 2007). To induce expression of H2Bj-GFP, embryonic mice were pulsed by doxycycline (2 mg/ml, 5% sucrose water, ad libitum through the dams or directly) from E0 to P42. Alternatively, adult animals were pulsed with doxycycline from 6 to 10 weeks of age. In some instances, both pre-pubertal and post-pubertal animals received BrdU (5-bromo-2'-deoxyuridine, Roche, 1 mg/ml) or IdU (5-iodo-2'-deoxyuridine, Sigma; 1 mg/ml) i.p. over the last six to ten consecutive days of the pulse period to co-localize H2Bj-GFP LRCs with BrdU/IdU LRCs. At the end of the pulse period, withdrawal of the doxycycline resulted in suppression of H2Bj-GFP transgene expression. Bone marrow analysis for co-localization of H2Bj-GFP with known hematopoietic stem cell surface markers was used as a positive control and detailed in flow cytometry methods. Transgenic mice not receiving doxycycline served as a negative control as detailed in the quantification methods. Pre-pubertal pulsed bone marrow and ovaries were harvested at pulse day 42 ("sexually mature", n=3), chase 1 week (n=2), 2 weeks (n=2), 1 month (n=3), 2 months (n=3), 3 months (n=4), and 6 months (n=1), and evaluated for GFP expression. Post-pubertal pulsed bone marrow and ovaries were harvested at pulse 1 month (n=3), chase 1 month (n=3), and chase 2 months (n=3). In some instances mice were injected with BrdU or CldU (2'-chloro-2'-deoxyuridine; Sigma; 1 mg/ml) 2 h prior to sacrifice to correlate mitotic cells with H2Bj-GFP LRCs.

BrdU/IdU Labeling and hCG Stimulation.

BrdU & IdU pulse-chase experiments were repeated at least three times with similar results using postpubertal (20-25 g) virgin female CD1 mice from Charles River Laboratories (Wilmington Mass.) or post-pubertal pulsed M2-Rosa26-rtTA; H2BJj-GFP mice. Animals were injected daily with 250 ul of 1 mg/ml BrdU or IdU i.p. for 7 or 10 days during the pulse period. On day seven or ten, 1-2 mice were sacrificed to visualize the initial BrdU labeling in the ovary as compared to intestinal controls. During the chase period, one to two mice were sacrificed at various time points for a chase period up to 14 weeks. During BrdU chase week 11 (pulse-chase experiment #1) and 12 (pulse-chase experiment #2), ten animals in proestrus by vaginal cytology were injected with 10 IU hCG i.p. and subsequently followed for 5 days to capture each stage of a complete estrous cycle.

Immunofluorescence.

Immunofluorescence and BrdU detection were performed as previously described in detail (Szotek et al., 2007). In brief, tissues were fixed, gelatin embedded, sectioned, blocked, and stained. Primary Antibodies were as follows: BrdU-Alexa 488 (1:20), BrdU-Alexa 555 (1:20), BrdU-Alexa 647 (1:20), GFP-Alexa 488 (1:200; Molecular Probes), Troma-1 (1:50), CD105 (1:10), Connexin 32 (1:10; Iowa Studies Hybridoma Bank, Iowa City, Iowa); c-Kit receptor (1:100, R & D Systems, Minneapolis Minn.); a-SMA (1:5000), β-Catenin (1:1500, Sigma, St. Louis Mo.), Gata-4 (1:100, Santa Cruz Biotechnology, Santa Cruz Calif.); EpCAM, CD31 (PE-CAM), CD45, GR-1-PE, Mac-1-PE, Ter119-PE, pan-NK-PE, CD90, CD34 (all 1:50, Becton Dickinson), VASA/MVH (1:1000, generous gift from T. Noche, Mitsubishi Kagaku Institute of Life Sciences, Tokyo, Japan), NG2 (1:350, Chemicon), PDGFRb (1:25, E-Bioscience), and CD44 (1:25, Caltag) diluted in 1% BSA/PBS and incubated in a humidified chamber for 1 h. Secondary antibodies were as follows: AlexaFluor 488 donkey-anti-(goat, rabbit, rat), AlexaFluor 555 donkey-anti-(goat, rabbit, rat), and AlexaFluor 647 donkey-anti-(goat, rabbit, rat) (1:1000, Molecular Probes) diluted in 1% BSA/PBS and incubated for 1 h at RT in a humidified chamber. Nuclei were counterstained with 4'6'-diamidino-2-phenylindole-(DAPI 1:20,000) impregnated Vectashield (Vector Labs, Burlingame Calif.) mounting media for microscopy, using a Nikon 80i microscope with epifluorescence attachments. Images were captured using the SPOT RT-KE Camera and Spot Advance Software (Diagnostic Instruments, Sterling Heights Mich.). Confocal images and in vitro live cell images were captured on the BD Pathway imaging system and analyzed using BD Attovision software.

Quantification of Labeling.

Quantification of BrdU and H2Bj labeled nuclei was performed either by flow cytometry (bone marrow) or by image acquisition as described above (all images with camera settings: Exp. 500 ms; Gamma=0.95; Gain=4) and analysis using ImageJ software (NIH) with the nucleus counting plugin. The quantification analysis was standardized using Adobe PhotoShop software to set a threshold level of 60 (determined by images of transgenic mice not receiving doxycycline as a baseline control for "leaky" GFP) on each greyscale image. The ImageJ nucleus counting plugin was set to count particle sizes from 4-500 pixels with K-means clustering to obtain the nuclei count data. Grayscale images were evaluated from at least three images per animal and three animals per time-point. Quantification of in vitro intensity was performed on the BD Pathway imager using BD Attovision software. Cell nuclei were electronically gated as regions of interest and individual nuclei intensity was determined. The nucleus of greatest intensity was designated as the point from which loss of signal was measured and sequential elliptical rings of equal numbers of cells were established to estimate the loss of signal intensity. All experiments were performed in triplicate.

Parabiosis. Parabiosis and ovarian germ cell/stromal chemoablation (cytoxan/busulafan) experiments were performed exactly as previously described (Eggan et al., 2006; Johnson et al., 2005; Wagers et al., 2002; Wright et al., 2001) in accordance with the guidelines established by the Joslin Diabetes Center IACUC for the humane care and use of animals. C57BL/6 wild type isogenic littermates were parabiosed at 4-8 weeks of age to either C57BL/Ka-β-actin/eGFP (n=6 pairs; JAX GEMM Strain: STOCK Tg(ACTB-EGFP) D4Nagy/J; stock #003116) or ubiquitin-GFP (n=4 pairs; JAX GEMM Strain: C57BL/6-Tg(UBC-GFP)30Scha/j; stock #004353) mice purchased from Jackson Laboratories. ACTB-EGFP animals were euthenized after 2 months and UBC-GFP animals after 5 weeks of parabiosis. Blood was analyzed for chimerism by flow cytometry. Ovaries were harvested and prepared for immunofluorescence as described herein.

Irradiation and Actin-GFP Bone Marrow Transplantation.

β-actin-GFP transgenic mice were purchased from Jackson Laboratories (JAX GEMM Strain: STOCK Tg(ACTB-EGFP)D4Nagy/J; stock #003116) and nucleated marrow cells were harvested by crushing murine long bones in PBS/2% FCS using a mortar and pestle. 1-4 million nucleated marrow cells were injected intravenously into C57BL/6 mice (n=4) conditioned with 9.5Gy within 24 hours of transplantation. 4 weeks post transplant peripheral blood was harvested and engraftment confirmed by CBC analysis (Hemavet 850, Drew Scientific) and flow cytometry to detect GFP, after RBC lysis. Mice were sacrificed 8 weeks after bone marrow transplant.

Flow Cytometry.

To validate the ability of doxycycline induced GFP expression in M2-Rosa26-rtTA; tetO-H2Bj-GFP mice to identify slow cycling label retaining stem cells, we analyzed the bone marrow for co-localization with the known hematopoietic stem cell (HSC) phenotype of $Lin^-/c\text{-}Kit^+/Sca\text{-}1^+$ (Morrison et al., 1995; Morrison and Weissman, 1994; Orlic et al., 1993) over the course of the chase. GFP expression in whole bone marrow and the $Lin^-/c\text{-}Kit^+/Sca\text{-}1^+$ fraction was assessed in the control mice receiving no doxycycline (GFP negative gate) and in embryonic (E0-P42) doxycycline pulsed mice, at the end of the pulse and following 1 week, 2 weeks, 1 month, 2 months and 6 months of chase (no doxycyline).

Bone marrow was harvested by crushing femoral bone shafts in PBS with heat inactivated 2% FBS. Cells were stained with lineage-specific biotinylated antibodies (CD3, CD8, CD4, GR-1, Mac-1, Ter119, and B220), Scat PE-conjugated, and cKit APC-conjugated (all BD Pharmingen, San Jose, Calif.) for 20 minutes at 4 C. Cells were washed twice and then stained with streptavidin PerCp-conjugated (BD Pharmingen) antibody for 20 minutes at 4 C. Cells were washed and re-suspended in PBS for immediate analysis or fixed with 2% paraformaldehyde for analysis within 24 hours. Flow cytometric analysis was performed using a FACScalibur (BD Biosciences) flow cytometer. Live cells were gated based on forward-scatter (FSC) and side-scatter (SSC) parameters. Wild type bone marrow was analyzed to set the GFPHigh/low/– threshold gates. At least $2.5 \times 10^5$ events were collected. Data was analyzed on FloJo version 8.1.1 analysis software.

To determine if H2Bj label retention co-localizes with and enriches for the SP phenotype (as determined by Hoechst 33342 exclusion), ovaries were dissected, cleared of their bursa, and enzymatically digested at 37 C in 0.2% (b/w) collagenase type II (Gibco/BRL type II in DMEM) for 30-45 min. followed by collagenase inactivation with F12+20% FBS and transfer of the ovaries to a 6 well plate for mild trituration to disperse the more superficial coelomic and sub-coelomic/stromal cells. The ovaries were removed and the remaining media collected, centrifuged, and the cells resuspended in PBS, filtered through a 70 μm mesh (BD Falcon), centrifuged again, and resuspended in 2 ml ammonium chloride (ACK) RBC lysis solution on ice for 3 min. After addition of 10 ml HBSS+2% FBS, the cells were centrifuged, then resuspended in DMEM+2% FCS, and counted.

Cell sorting and analysis of GFP and SP cells was performed in the Flow Cytometry Laboratory of the Department of Pathology and the Center for Regenerative Medicine according to their published protocols (Preffer et al., 2002) and as previously described (Szotek et al., 2006). Single cell suspensions were stained with 5 μg/ml of the A-T intercalating Hoechst 33342 dye for 90 min at 37 C, washed, and resuspended in PBS containing 2% fetal calf serum for analysis of GFP and SP co-localization using the LSRIII flow cytometer (Becton Dickinson). At least $2.5 \times 10^5$ events were collected for each analysis and analyzed using FloJo version 8.1.1 software.

Colony Forming Unit (CFU) Assay and BD Pathway Live Imaging.

After isolation of coelomic and subcoelomic/stromal cells as described above, cells were counted by hemocytometer and limiting dilutions of $2 \times 10^5$, $1 \times 10^5$, $5 \times 10^4$, $2.5 \times 10^4$, $1 \times 10^4$ and $5 \times 10^3$ cells were added to 2 mL of Murine MesenCult Media according to protocol (StemCell Technologies) and cultured at 37 C, 5% $CO_2$ for 14 days to obtain an optimal plating number of $1 \times 10^4$ for subsequent studies. During the course of incubation, the plated cells were routinely observed and imaged for GFP expression and colony formation. Colonies were considered GFP positive if a minimum of 2 contiguous nuclei had visually detectable GFP epifluorescence. At the end of the 14 day incubation period, the percentage of GFP positive colonies was estimated visually using an epifluorescent microscope and then macroscopic colony counts were obtained after Giemsa staining. For live imaging, an identical protocol was used except colonies were incubated and imaged under the BD Pathway live cell confocal imager (Becton Dickinson) using BD Attovision imaging software. Data analysis was performed using ImageJ software (NIH). All experiments were performed in triplicate.

Statistical Analysis. In MTT assays, MIS-, doxorubicin-, and paclitaxel-treated and untreated samples were analyzed by using the univariant two-tailed Student t test, with P ≤0.05conferring statistical significance. All experiments were performed in triplicate. In ovarian somatic stem cell studies, all p-values were calculated with the use of two-tailed student's t-test. Differences with p-values less than 0.05 were considered significant.

Example 1

Identification of SPs in Mouse Ovarian Cancer Cell Lines

Figure 1C:
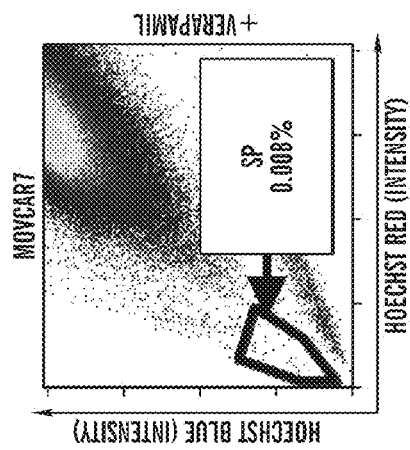
Figure 1B:
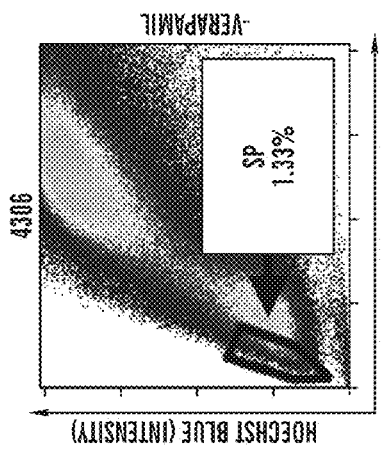
Figure 1D:
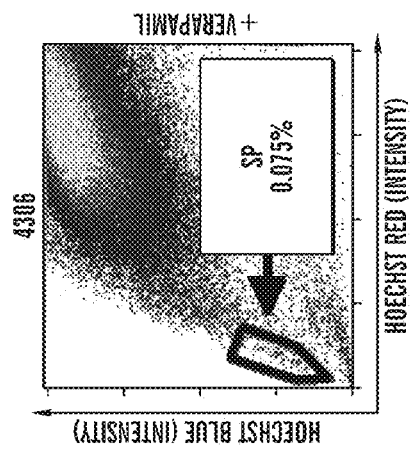
Figure 1F:
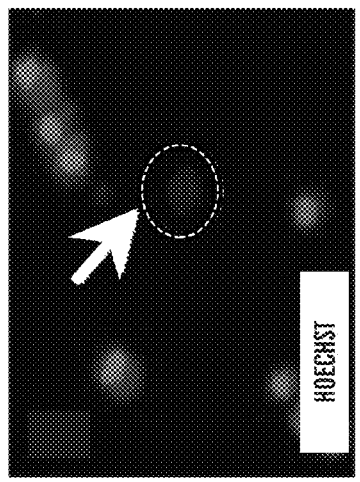
Figure 1H:
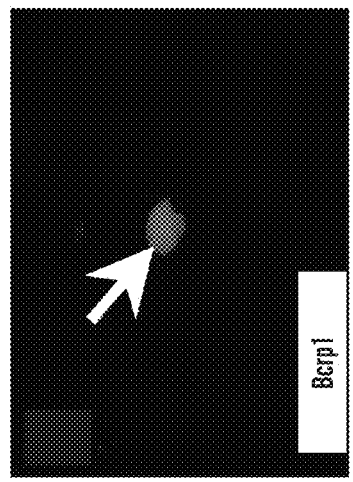
Figure 1E:
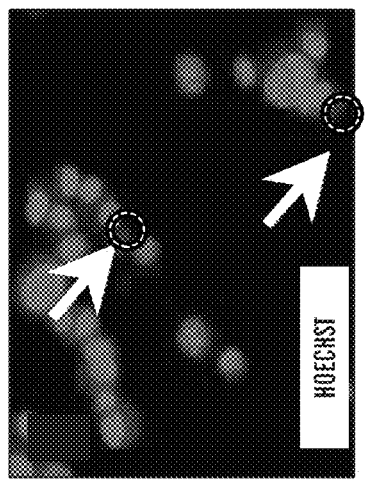
Figure 1G:
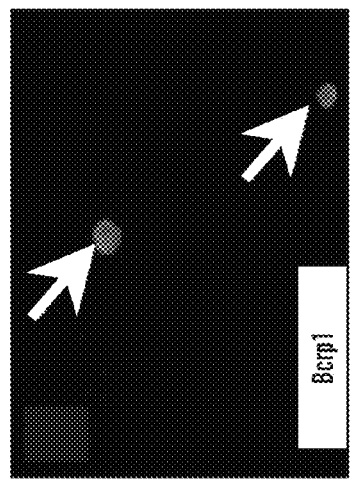
Figure 2A:
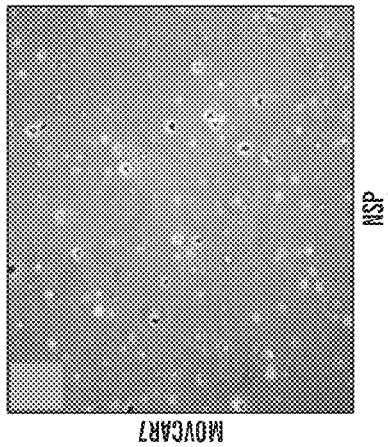
FIGS. 2A-2J shows growth characteristics of mouse SP cells. MOVCAR 7 SP (2A) and 4306 SP (2C) and MOVCAR NSP (2B) and 4306 NSP (2D) cells recovered in culture and photographed with an inverted ×10 phase-contrast microscope. SP cells from both cell lines (MOVCAR and 4306) form tight colonies after 4 days in culture, whereas NSP cells are scattered and do not proliferate. MOVCAR 7- and 4306-sorted SP cells (2E and 2H) were cultured for 7-10 days, resorted by flow cytometry (2F and 2I), recovered for an additional 7-10 days, and then reanalyzed by flow cytometry (2G and 2J). Each successive sort demonstrated the enrichment of SP cells and the presence of NSP cells.
Figure 2B:
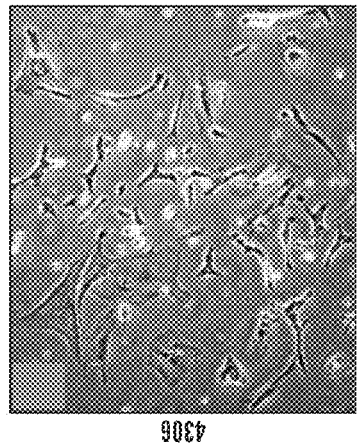
Figure 2C:
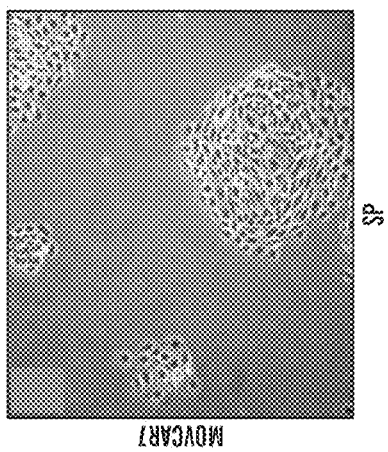
Figure 2D:
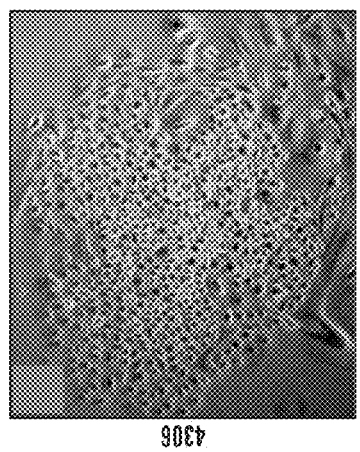
Figure 2E:
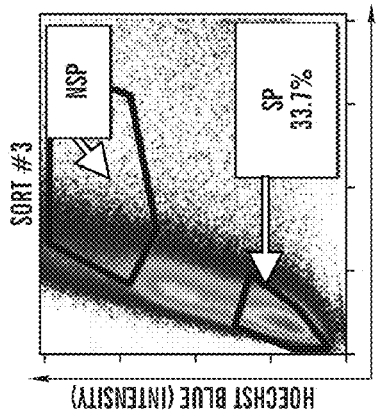
Figure 2H:
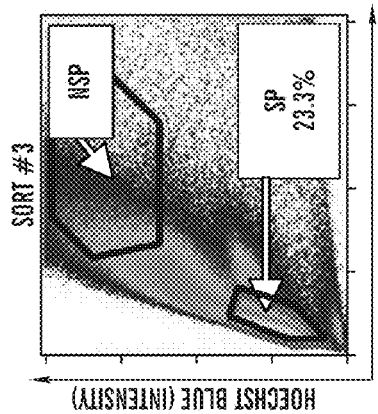
Figure 2F:
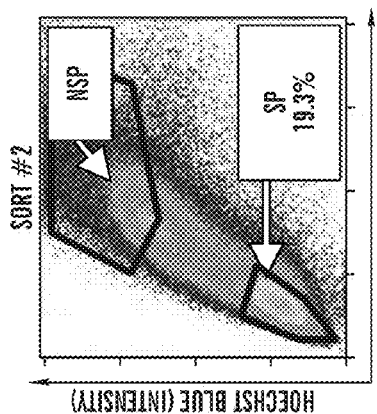
Figure 2I:
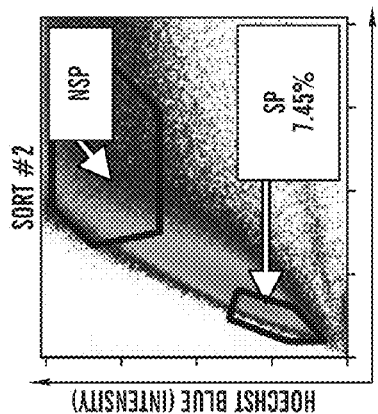
Figure 2G:
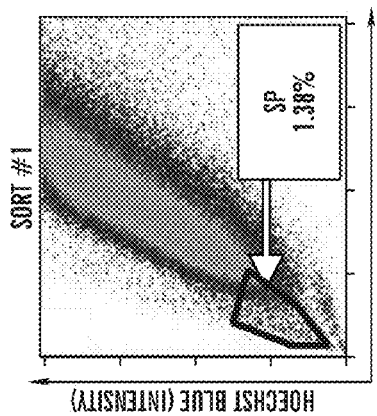
Figure 2J:
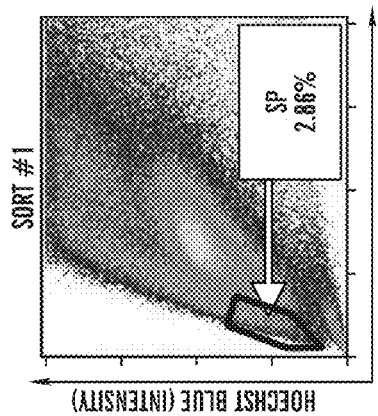

To determine whether mouse ovarian cancer cell lines contain candidate cancer stem cells, Hoechst 33342 was used to sort for the SP phenotype. The serous adenocarcinoma-recapitulating MOVCAR 7 and 8 cell lines were developed by using the MIS type II receptor (MISRII) promoter to drive the SV40 T antigen (19). The endometrioid carcinoma-recapitulating 4306 cell line was developed from conditional LSL-K-$ras^{G12D/+}/Pten^{loxP/loxP}$ mice in which the ovarian surface epithelium was infected with adenovirus expressing Cre recombinase (20). Flow cytometry demonstrated a very high percentage of $Hoechst^{Low}$ SP cells in the MOVCAR 7 and 4306 cell lines (FIGS. 1A and B), whereas SP was not detected in MOVCAR 8. Verapamil, a BCRP1 inhibitor (18), effectively eliminated the SP in both MOVCAR 7 and 4306 cells (FIGS. 1C and D). The average first sort percentage of SP cells was 6.28% (n=6) for MOVCAR 7 and 1.83% (n=4) for 4306 cells, which is elevated relative to the SP found in other somatic and malignant sources (3, 18, 21). Colocalization of $Hoechst^{Low}$ and Bcrp1 immunoreactive MOVCAR 7 and 4306 cells confirmed the presence of SP cells (FIG. 1E-H and data not shown). Bcrp1 mRNA was detected by qualitative RT-PCR in SP cells (data not shown). Thus, MOVCAR 7 and 4306 cells possess SPs with Hoechst efflux characteristics reminiscent of those defined in hematopoietic stem cells.

Example 2

Ex Vivo Growth of SP and NSP Cells

Growth characteristics of the SP and NSP cells were consistent with previous findings for cancer stem cells (21).

MOVCAR 7 and 4306 cells were sorted by flow cytometry and equal numbers of SP and NSP cells cultured. SP cells from both cell lines formed characteristic compact circular colonies with a cobblestone appearance and survived numerous passages (FIGS. 2 A and C; n=9). NSP cells from both cell lines were sparse and failed to proliferate beyond 1-2 weeks (FIGS. 2 B and D; n=9). These differences were not a consequence of prolonged Hoechst retention in the NSP cells because propidium iodide was used to gate out all nonviable cells. Serial sorting and reanalysis (total passages=3) of SP cells demonstrated enrichment of the SP and the presence of NSP cells (FIG. 2 E-J), suggesting asymmetric division occurred during culture (FIGS. 2 F, G, I, and J). Thus, SP cells are able to self-renew, be enriched, and produce NSP cells when recovered and serially sorted in culture.

Example 3

SP Cells are in $G_1$ Cell Cycle Arrest and Resistant to Doxorubicin In Vitro

Figures 3A, 3B:
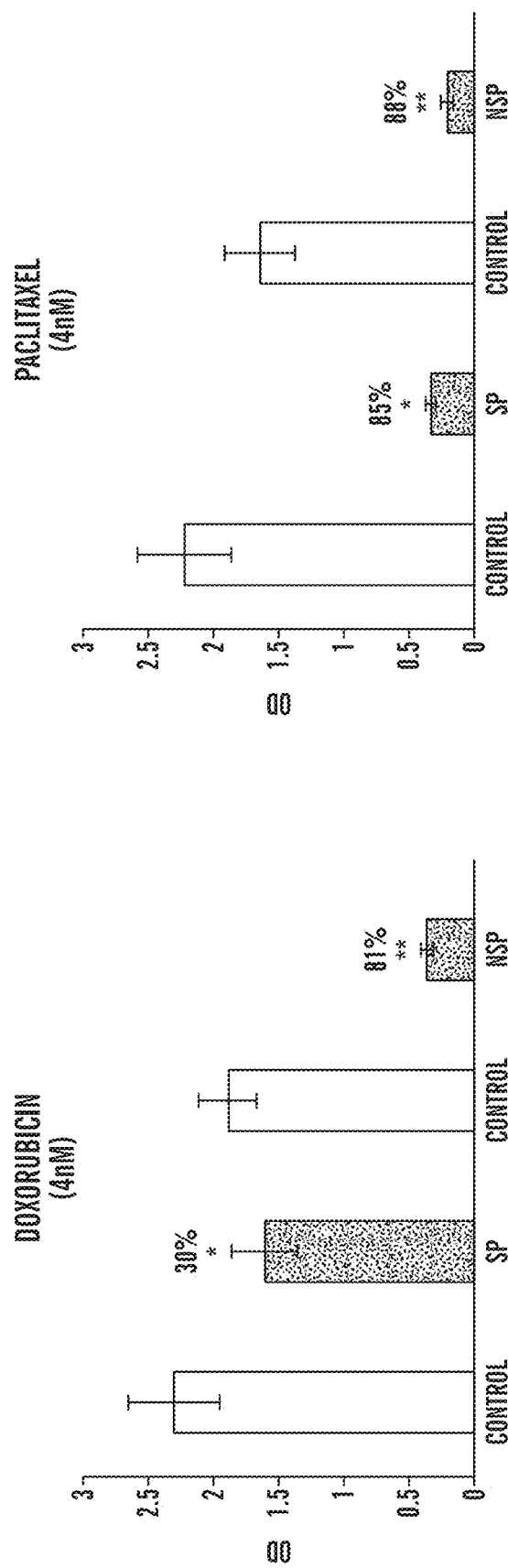
FIGS. 3A-3F show side population (SP) cells with decreased inhibition by doxorubicin and $G_1$ cell cycle arrest. MOVCAR 7 cells were sorted for MTT growth-inhibition analysis against doxorubicin and paclitaxel. SP cells showed 30% inhibition (3A) by doxorubicin (*, $P<4.2\times10^{-4}$) and 85% inhibition (3B) by paclitaxel (*, $P<6.7\times10-10$) compared with vehicle-treated controls. NSP cells were inhibited by doxorubicin and paclitaxel by 81% and 88% versus vehicle-treated controls [**, $P<3.2\times10^{-11}$ (3A); *, $P<5.1\times10^{-10}$ (3B)]. (3A) NSP cells were significantly more inhibited by doxorubicin than by SP cells (81% versus 30% growth inhibition; ***, $P<1.6\times10^{-9}$). Cell cycle analysis of three populations was performed as shown in 3C. Hoechst$^{High}$ NSP and Hoechst$^{Mid}$ cells (3D and 3E) demonstrate a predominance of S phase, 69.3% (average=45.3%) and 68.9% (average=51.5%), respectively, and decreased $G_1$-arrested cells, 23% (average=53%) and 15.9% (average=39%), compared with Hoechst$^{Low}$ SP cells [P<0.0407 (3F)]. Hoechst$^{Low}$ SPs demonstrate a predominance of $G_1$-arrested cells, 63% (average=65.8%), and decreased S phase replicating cells, 33.4% (30.57%). All experiments were performed in triplicate.
Figure 3C:
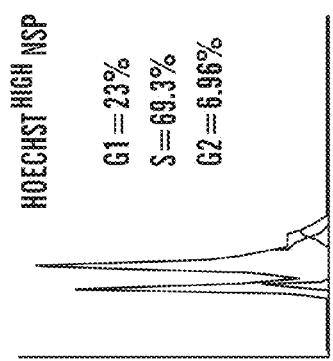
Figure 3D:
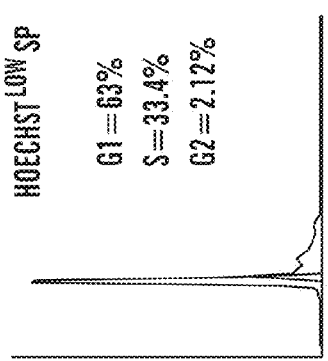
Figure 3E:
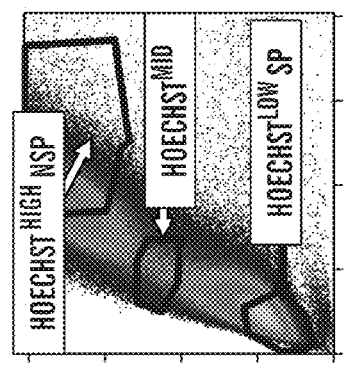
Figure 3F:
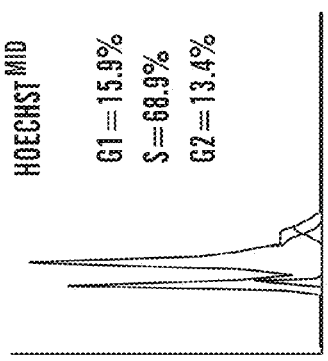

By definition, SP cells should express high levels of BCRP1 and thus be able to efflux the lipophilic dye Hoechst 33342 and some lipophilic anticancer drugs, including those used in the treatment of ovarian cancer (18, 22). The lipophilic anticancer drug doxorubicin is a substrate of the BCRP1 transporter, whereas the lipophilic microtubule inhibitor paclitaxel is not (23). To investigate the functional significance of the Bcrp1 transporter found in MOVCAR 7 SP cells, we tested their response to doxorubicin and paclitaxel, as compared with that observed in the NSP, by methylthiazoletetrazolium (MTT) proliferation assays (FIG. 3). MOVCAR 7 SP cells were only inhibited by 30% after treatment with doxorubicin, whereas the NSP cells showed 81% inhibition (FIG. 3A). In contrast to doxorubicin, MOVCAR 7 SP and NSP cells were almost equally inhibited by the Bcrp1-resistant paclitaxel (FIG. 3B; SP=85% inhibition; NSP=83% inhibition). Quiescence is one of the defining characteristics of somatic stem cells (24). Cell cycle analysis of three sorted populations, Hoechst$^{Low}$ SP, Hoechst$^{Mid}$ NSP, and Hoechst$^{High}$ NSP (FIG. 3C), revealed that the Hoechst$^{Mid}$ and Hoechst$^{High}$ NSP cells had a higher percentage of cells in S phase (FIGS. 3 D and E), compared with Hoechst$^{Low}$ SP (FIG. 3F). In contrast, Hoechst$^{Low}$ SP cells demonstrate a predominance of cells in the $G_1$ phase (FIG. 3F) compared with the Hoechst$^{Mid}$ and Hoechst$^{High}$ NSP cells (FIG. 3D).

Example 4

In Vivo Growth Characteristics of MOVCAR 7 SP and NSP Cells

Figure 4B:
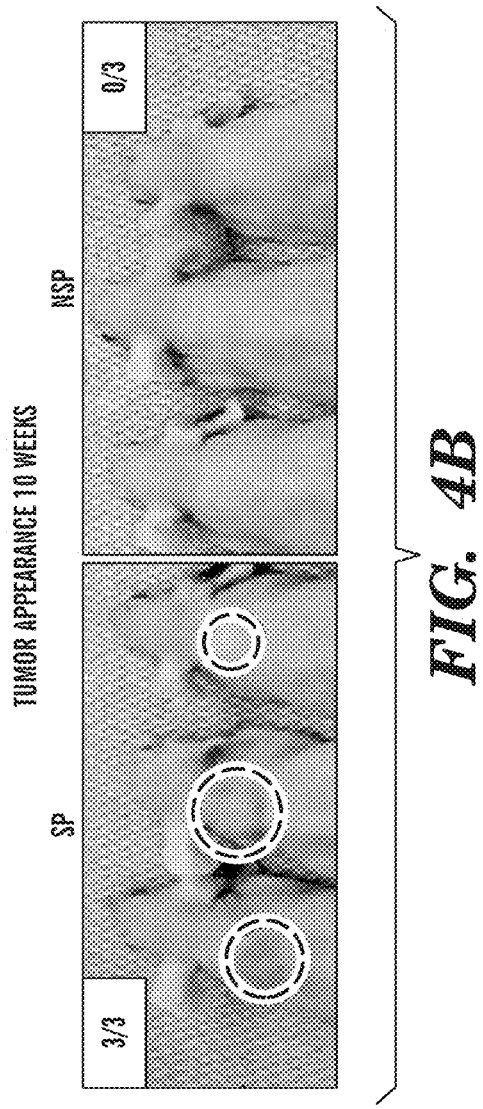
Figure 4A:
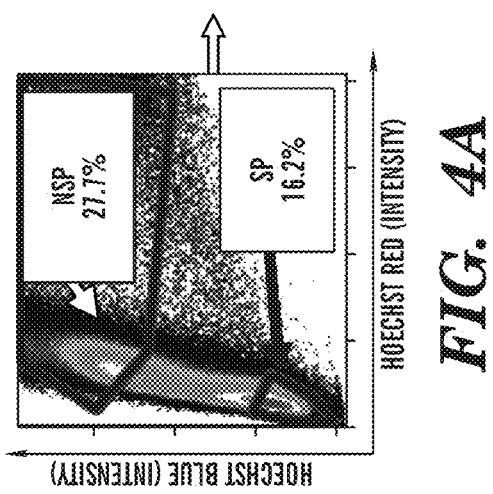

To assess in vivo tumorigenicity of MOVCAR 7 SPs and NSPs, viable propidium iodide-negative SP and NSP cells were sorted and injected into the dorsal fat pad of nude mice (FIG. 4A and Table 1, which is published as supporting information on the PNAS web site). Tumors appeared in three of three animals at 10 weeks after injection of $5.0 \times 10^5$ SP cells, whereas animals injected with an equal number of NSP cells had no detectable tumors (zero of three) at that time (FIG. 4B). Tumors appeared in two of three of the NSP animals only after 14 weeks. Tumors appeared at 7 weeks in animals injected with $7.5 \times 10^5$ SP cells, whereas NSP-injected animals had no detectable tumors (zero of three) at that time and only appeared after 10 weeks in two of three animals (Table 1). To investigate whether the appearance of tumors in the NSP could possibly be explained by incomplete sorting, we reanalyzed the sorted populations by using identical gating and found 82.6% SP cell purity (FIG. 4C; NSP contamination=2.63% or ~13,150 SP cells in a total of $5 \times 10^5$ cells per animal; 19,750 SP cells in a total of $7.5 \times 10^5$ cells per animal) and 92.3% NSP cell purity (FIG. 4D; SP contamination=1.72% or ~8,600 SP cells in $5 \times 10^5$ cells per animal; 12,900 SP cells in $7.5 \times 10^5$ cells per animal). In addition, the NSP tumors dissected from animals at euthanization showed verapamil-sensitive SP cells (FIGS. 4 E and F), suggesting that SP cells have the potential to initiate earlier tumor growth at lower numbers. In a parallel experiment, preinjection analysis demonstrated an SP fraction equal to 0.21% (~12,600 SP cells per animal) of the $6 \times 10^6$ unsorted cells per animal injected into 50 nude mice (data not shown). The average time to appearance of these tumors was ~9 weeks; in close agreement with our $7.5 \times 10^5$ NSPs (~12,900 SP cells) injected animals and corroborating our speculation that a very small population of SP cells has the potential to initiate tumor growth in vivo.

TABLE 1

MOVCAR 7 SP versus NSP tumorgenicity in vivo.

| | | Weeks after injection | | |
|---|---|---|---|---|
| | | 7 | 10 | 14 |
| Experiment no. 1 ($5 \times 10^5$ cells per animal) | SP | *0/3 | 3/3 | 3/3 |
| | NSP | 0/3 | 0/3 | 0/3 |
| Experiment no. 2 ($7.5 \times 10^5$ cells per animal) | SP | 3/3 | 3/3 | 3/3 |
| | NSP | 0/3 | 2/3 | 2/3 |

*Number of animals with tumors at time point/total number of animal injected.

Example 5

MOVCAR 7 and 4306 SP Cells Respond to MIS In Vitro

Figure 5B:
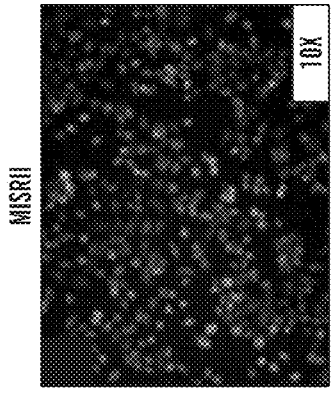
Figure 5D:
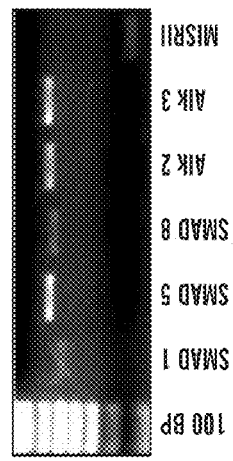
Figure 5A:
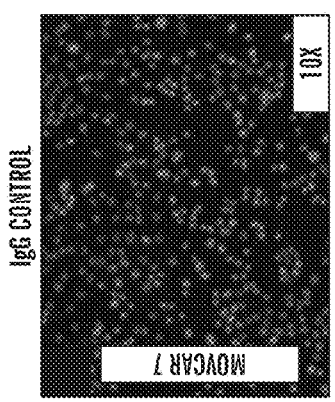
Figure 5C:
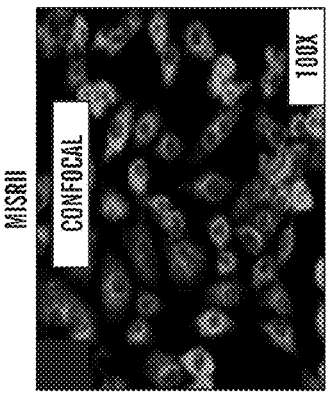

MIS has been shown to inhibit MOVCAR 7 both in vitro and in vivo (25). Thus, we investigated whether MIS inhibits MOVCAR 7 and 4306 SP and/or NSP cells in vitro. We first confirmed that SP and NSP cells possess an intact MIS signal transduction pathway, previously shown to be required for MIS responsiveness in the embryonic urogenital ridge (26). By using anti-MISRII antibody the inventors observed that MOVCAR 7 and 4306 cells express the MISRII receptor by epifluorescent and confocal microscopy (FIGS. 5B and 5C; 4306 cells not shown). The inventors then confirmed the presence of MISRII, MISRI (Alk 2 and 3), and Smad 1/5/8 mRNA by RT-PCR in sorted SP and NSP cells (SP in FIG. 5D; NSP and 4306 cells are the same but not shown), demonstrating that these cells would likely respond to MIS.

Figure 7B:
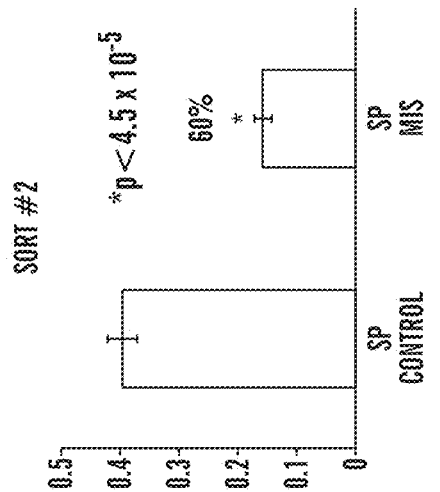
FIGS. 7A-7B show 4306 SP cells respond to MIS in vitro. The proliferation of 4306 SP and NSP cells was analyzed after the first sort by MTT assay (7A) and demonstrated significant inhibition of SP (37%; *, $P<5.2\times10^{-3}$), but not NSP, cells by MIS vs. vehicle control. Serially sorted 4306 SP cells were assayed (7B) and demonstrated that enriched SP cells remain responsive to MIS after the second sort (60% inhibition; *, $P<4.5\times10^{-5}$), but no significant inhibition was demonstrated after the third sort (17% inhibition, P=0.056, data not shown). All experiments were performed in triplicate.
Figure 7A:
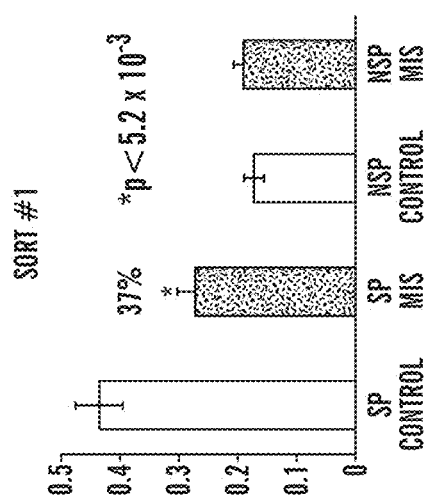

MOVCAR 7 and 4306 SP and NSP cells were sorted, incubated for 24 h, and treated with 10 μg/ml MIS for MTT proliferation assays. MOVCAR 7 SP and NSP cells responded to MIS after initial sorting of the neat population. MOVCAR 7 SP cells were inhibited by 86%, whereas NSP cells were inhibited by 93% compared with vehicle controls (FIG. 5 E). In contrast, only 4306 SP cells showed a significant inhibition of 37% by MIS (FIG. 7), However, because NSP cells could not reliably be maintained in culture for serial sorting, we evaluated the ability of MIS to inhibit the SP alone after enrichment in both cell lines. MOVCAR 7 serial sorting followed by MTT showed 93% inhibition after sort 2 and 94% inhibition after sort 3 (FIGS. 5 F and G). Serial sorting of 4306 cells followed by MTT showed 60% inhibition after sort 2 (FIG. 7), and no inhibition after sort 3 was observed (17% inhibition; P=0.054). Thus, MIS inhibits MOVCAR 7 and 4306 SP cells in vitro.

Example 6

Human Ovarian Cancer Cell Lines and Primary Patient Ascites Cells have SPs

Figure 8A:
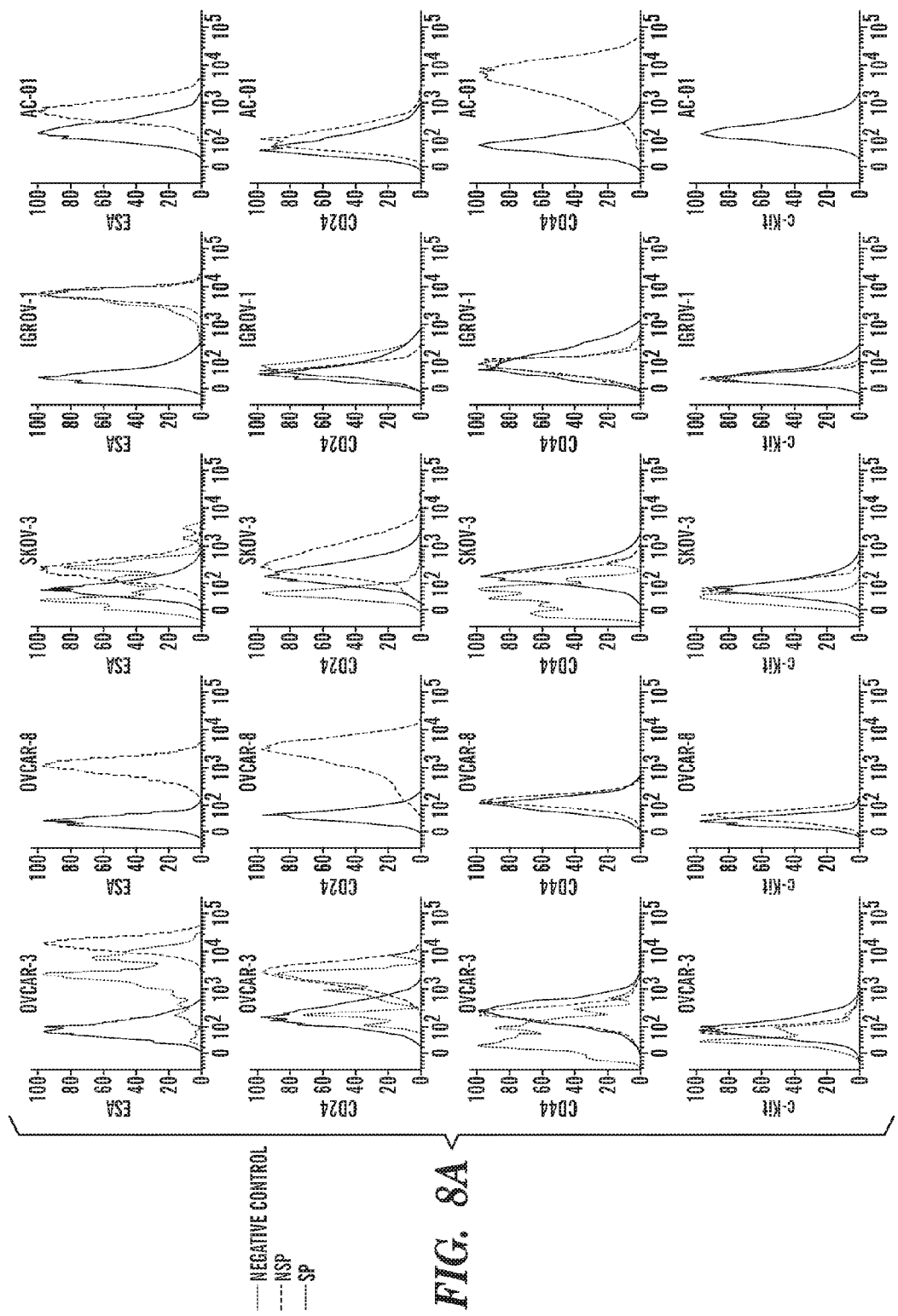
FIGS. 8A-8B shows the surface marker profile of human ovarian cancer cell lines(8A) and primary ascites cells (8B). No differential staining between SP and NSP cells was observed, and both populations were positive for these markers when staining was observed.
Figure 8B:
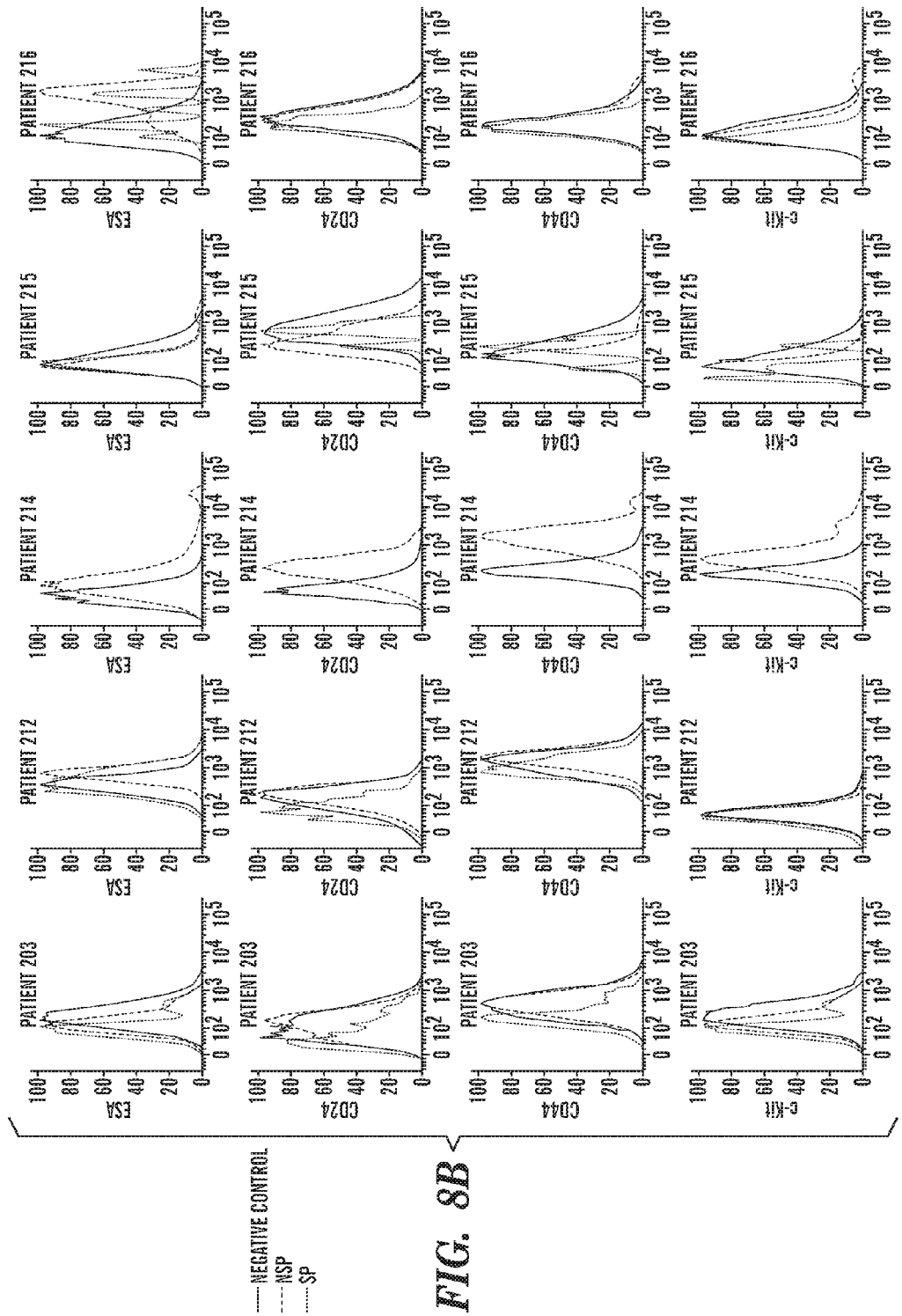

To determine the prevalence of SP cells in human ovarian cancer, we evaluated the cell lines OVCAR 3, OVCAR 8, SK-OV-3, and IGROV-1, as well as ascites from six ovarian cancer patients (see cell line and patient demographics in Table 2. Patient ascites cells were obtained directly from the operating theatre and analyzed within 96 h. The inventors detected verapamil-sensitive SP cells in IGROV-1 (FIG. 6A), OVCAR 3 (data not shown), and SK-OV-3 (21), but not in OVCAR 8 (FIG. 6B). Viable human ascites cells, selected as CD45−/CD31−, were found to exhibit verapamil-sensitive SP cells in four of six patients (FIGS. 6 C and D). Thus, an appreciable number of human ovarian cancer cell lines and primary ovarian cancer ascites cells possess SP cells. The inventors also performed immunofluorescent analysis of IGROV-1 and the ascites cells of patients 215 and 216, and discovered colocalization of BCRP1 with Hoechst$^{Low}$ cells in IGROV-1 and the ascites cells, (data not shown), whereas OVCAR-8 did not express Hoechst$^{Low}$ or BCRP1-positive cells (data not shown).

identify differential expression between SP and NSP cells, we analyzed mouse and human ovarian cancer cells by flow cytometry. All mouse and human SP cells were gated as negative for CD45 (common leukocyte antigen) and CD31 (platelet endothelial cell adhesion molecule 1/endothelial cells). Compared with NSP cells, the MOVCAR 7 SP cells were enriched in number of cells and intensity of expression of c-kit/CD117 (stem cell factor receptor), whereas 4306 and human SP and NSP cells did not express c-kit. MOVCAR 7 SP and NSP cells strongly express the tumor metastasis marker CD 44 (hyaluronic acid receptor), whereas 4306 cells and most human ovarian cancer cells do not. MOVCAR 7 and 4306 SP and NSP cells did not express CD24, CD34, CD105, CD133, or Sca-1 (Table 3). Human cell lines and ascites cells showed variable expression of the epithelial cell marker epithelial-specific antigen/Ep-CAM (epithelial specific antigen) and CD24 (Table 2 and FIG. 8). These markers, aside from c-kit in MOVCAR 7, did not add to the consistent SP phenotype and Bcrp1 immunostaining we have observed in identifying putative ovarian cancer stem cells in both mouse and human.

TABLE 2

Demographics and surface markers of human ovarian cancer cell lines and primary ascites.

| | Sample #/ cell line | Pathology | Age, yr | SP, % | ESA | CD24 | CD44 | c-Kit |
|---|---|---|---|---|---|---|---|---|
| Human cell lines | OVCAR-3 | Serous adenocarcinoma | 60 | Pos (0.085) | ++++ | ++++ | − | − |
| | OVCAR-8 | Serous adenocarcinoma | 60 | Neg | − | − | − | − |
| | SK-OV-3 | Serous adenocarcinoma | 64 | Pos (0.16) | + | − | +/− | − |
| | IGROV-1 | Serous adenocarcinoma | 47 | Pos (0.12%) | ++++ | − | − | − |
| Patient ascites cells | AC-01 | Serous adenocarcinoma | 56 | Neg | − | − | − | − |
| | TC 203 | Clear cell CA | 55 | Pos (0.047%) | +/− | − | − | − |
| | TC 212 | Clear cell CA | 54 | Pos (0.6%) | +/− | − | − | − |
| | TC 214 | Serous adenocarcinoma | 71 | Neg | +/− | − | − | − |
| | TC 215 | Serous adenocarcinoma | 71 | Pos (0.047%) | − | − | − | − |
| | TC 216 | Serous adenocarcinoma | 66 | Pos (0.69%) | +++ | − | − | − |

All samples were gated on SP/CD45−/CD31− population, and all patient cells were from ascites. SP positivity was assessed by flow cytometry and based on >90% elimination of SP with the addition of verapamil. Surface marker positivity was assessed by flow cytometry. Markers were ranked based on percent positive cells: −, <5%; +/−, 6-10%; +, 10-20%; ++, 21-40%; +++, 41-70%; ++++, >70%. Positivity was assessed by FACS. Markers were ranked based on percent positive cells: −, <5%; +/−, 6-10%; +, 10-20%; ++, 21-40%; +++, 41-70%; ++++, >70%.

Example 7

Mouse and Human Ovarian Cancer Cell Surface Phenotype

To investigate whether ovarian cancer cells express somatic and cancer stem cell surface markers, as well as to

TABLE 3

Cell surface markers on MOVCAR 7 and 4306 SP and NSP cells.

| Cell surface markers | Reactivity | MOVCAR 7 | | 4306 | |
|---|---|---|---|---|---|
| | | SP | NSP | SP | NSP |
| c-Kit (CD117) | Hematopoetic stem cells, mast cells | ++ | − | − | − |
| CD24 (BA-1) | Breast cancer progenitor cells, binds P-selectin | − | − | − | − |
| CD34 (mucosialin) | Hematopoetic stem cells epidermal stem cells | − | − | − | − |
| CD44 (HCAM) | Tumor metastasis, WBC adhesion, hyalurinidase | ++++ | ++++ | − | − |
| CD45 (leukocyte common antigen) | Pan-leukocyte marker | − | − | − | − |
| CD90 (Thy-1) | Thymocytes, myofibroblasts | − | ++++ | − | − |

TABLE 3-continued

Cell surface markers on MOVCAR 7 and 4306 SP and NSP cells.

| Cell surface markers | Reactivity | MOVCAR 7 SP | NSP | 4306 SP | NSP |
|---|---|---|---|---|---|
| CD105 (endoglin) | Endothelial, macrophage activation, TGF-β type III receptor, adhesion | – | ++++ | – | – |
| CD133 (prominin-1) | Hematopoetic progenitors, neural and endothelial stem cells, retinoblastoma | – | – | – | – |
| SCA-1 (Ly6-A/E) | Hematopoeitic stem cells, mast cells | – | – | – | – |

Positivity was assessed by flow cytometry. Markers were ranked based on percent positive cells: –, <5%; +/–, 6-10%; +, 10-20%; ++, 21-40%; +++, 41-70%; ++++, >70%.

Example 8

Mouse OSE Estrous Cycle Stage Dependent Proliferation

Figures 9A, 9B:
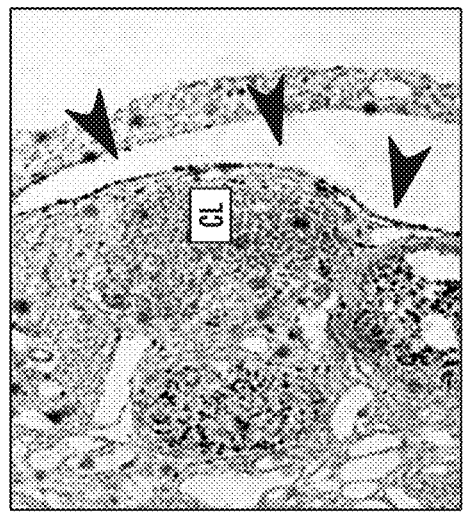
FIGS. 9A-D show coelomic epithelial cells proliferate in a cycle dependent manner. Mice in proestrus were injected with hCG followed by BrdU 2 hours before sacrifice in sequentially timed stages of estrus. Minimal coelomic epithelial BrdU incorporation was observed in the pre-ovulatory period (diestrus+proestrus; panel 9A; n=4) but showed substantial incorporation in the post-ovulatory period (estrus+metestrus; panel 9B; n=4). Quantification over the whole coelomic epithelium demonstrated 5.2±3.2% of pre-ovulatory and 18.9±1.3% of post-ovulatory cells incorporated BrdU, resulting in a greater than 3 fold increase in incorporation during the post-ovulatory phase (panel 9C, p<0.0011). Assessment of BrdU labeling within the post-ovulatory period at different anatomical sites (panel 9D) showed increased coelomic epithelial proliferation in association with antral follicles and corpora lutea (29.5±8%) when compared to the coelomic epithelium overlying primary and secondary follicles (2.3±0.95%, p<0.0014).
Figure 9D:
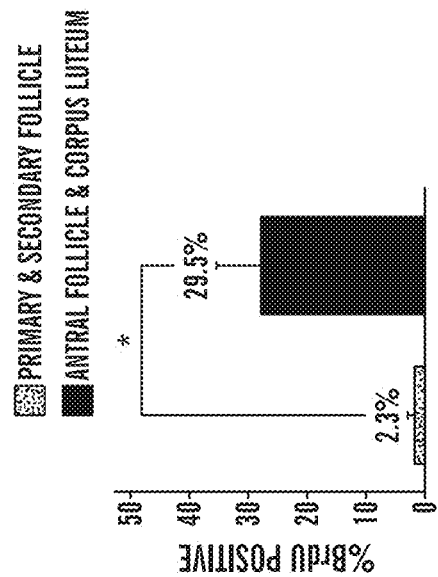
Figure 9C:
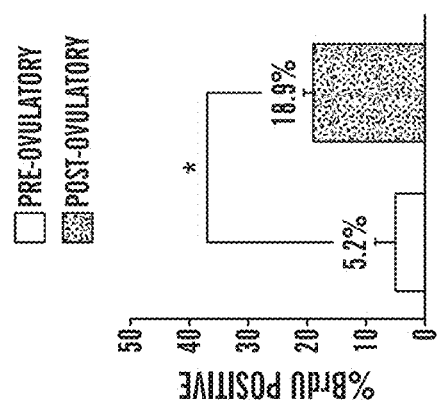

To identify the presence of stem cells in normal ovary, herein termed "ovarian somatic stem cells" the inventors performed a series of pulse-chase experiments in different transgenic mice strains. Short-term (2 hr) pulse BrdU labeling was used to investigate estrous cycle stage dependent proliferation in the mouse ovarian coelomic epithelium. Animals were grouped as preovulatory (diestrus, proestrus, and early estrus) and postovulatory (late estrus and metestrus) based on vaginal cytology, and analyzed for BrdU incorporation. Preovulatory ovaries demonstrated BrdU incorporation in proliferating granulosa cells, while little coelomic or stromal incorporation was observed (FIG. 9A). Postovulatory ovaries demonstrated that the ovarian surface epithelium proliferates in association with antral follicle formation (FIG. 9B red arrow) and in early metestrus in association with corpora luteum formation (FIG. 9B black arrows). Ovarian coelomic epithelial proliferation terminated in late metestrus and diestrus over newly formed corpora albicans. Quantification of ovarian coelomic epithelial proliferative activity by incorporation of BrdU over the entire coelomic epithelium demonstrated that an average of 5.2±3.2% of cells were dividing in the preovulatory group and 18.9±1.3% of cells were dividing in the postovulatory group (FIG. 9C). Within the postovulatory group, the majority of the increased ovarian surface epithelial proliferation was overlying antral follicles and corpora luteum (FIG. 9D), confirming the temporal-spacial relationship of postovulatory proliferation to coelomic epithelial repair.

Characterization of BrdU & Rosa-rtTA; tetO-H2Bj-GFP Labeling.

Figure 10B:
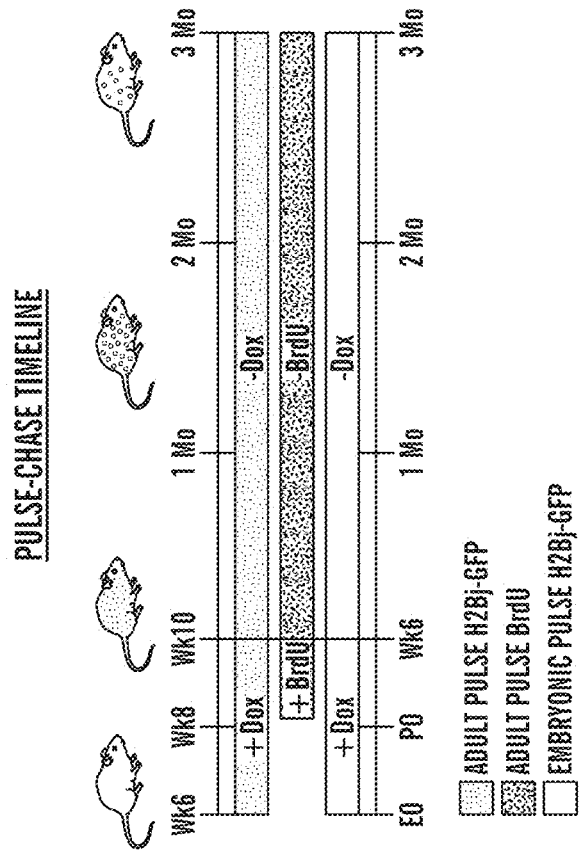
FIG. 10A-10D show characterization of BrdU and Rosa26-rtTA; tetO-H2Bj-GFP in the ovary. Rosa26-rtTA; tet0-H2Bj-GFP doxycycline responsive mice were engineered as depicted in panel 10A. Panel 10B outlines the pulse-chase schemes used in this study. Animals were pulsed with doxycycline either beginning embryonically (E0-6 wk) or beginning as adults and from 8.5 wk-10 wk with BrdU/IdU. Pulse-chase labeling efficiency of whole bone marrow, $Lin^-$ $Kit^+$ $Sca-1^+$ hematopoietic stem cells, whole ovary, and coelomic/subcolomic ovary were analyzed and compared (FIGS. 16 & 16C). Significant variability in initial whole ovary labeling was observed between the labeling techniques (panel 10C, p<0.05, *). After three months chase there was a significant difference in whole ovary label retention when comparing BrdU to the adult and embryonic pulse H2Bj-GFP labeling methods (panel 10C, p=0.016, * & p=0.010, *). There was no significant difference noted at 3 months chase between the two H2Bj-GFP pulse labeling methods (panel 10C, p=0.12). Quantification of coelomic/subcoelomic labeling efficiency demonstrated no significant difference between the two H2Bj pulse times (91% & 88%, p=0.43), while there was a significant difference between both adult and embryonic pulsed H2Bj-GFP techniques and BrdU (panel 10D, p=0.0016 & p=0.00011,*) Likewise, no significant difference was noted in label retention after three months chase in the H2Bj-GFP animals (panel 10D, p=0.794) while there remained a significant difference in label retention between the H2Bj animals and the BrdU animals (panel 10D, p=0.021 & p=0.041, **).
Figure 10A:
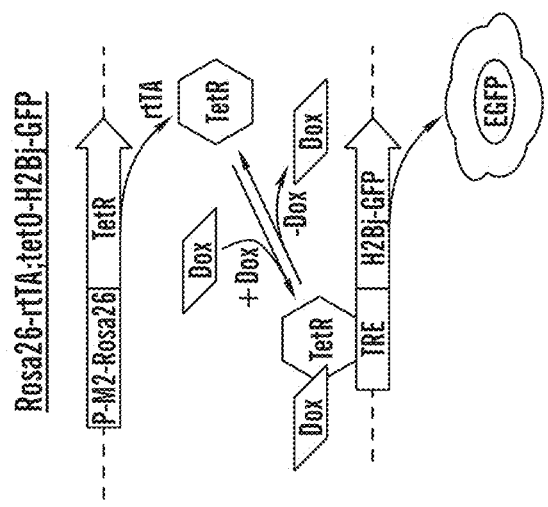

To determine if a population of slow cycling LRCs exists in the mouse ovary, the inventors used pulse-chase labeling with BrdU/IdU or tetracycline regulated H2Bj-GFP fusion protein in pre- and postpubertal female mice. Rosa26-rtTA; tetO-H2Bj-GFP mice were engineered as depicted in FIG. 10A and as previously described (Brennand et al., 2007). The timeline for embryonic (E0-P42) Rosa26-rtTA; tetO-H2Bj-GFP, adult (6 w-10 w) Rosa26-rtTA; tetO-H2Bj-GFP, and adult (6 w-7 w) BrdU pulse-chase experiments is shown in FIG. 10B. To validate the ability of Rosa26-rtT; tetO-H2Bj-GFP mice to identify somatic stem cells in a known model system, flow cytometry was used to compare bone marrow GFP label retaining cells to the hematopoietic stem cell phenotype Lin$^-$cKit$^+$Sca-1$^+$. Analysis of whole bone marrow from wild type and Rosa26-rtTA; tetO-H2Bj-GFP animals not receiving a doxycycline pulse were used to set the flow cytometry gates. Animals administered doxycycline during the embryonic period demonstrated that 37.6±12% (SE, standard error) of whole bone marrow and 81.36±7.6% of Lin$^-$cKit$^+$Sca-1$^+$ cells labeled during the pulse period (FIG. 16A). After 2 and 6 month chase periods respectively, 0.47±0.22% and 0.2±0.10% of WBM and 9.64±2.1% and 2.93±1.1% of Lin$^-$cKit$^+$Sca-1$^+$ cells retained GFP label above the gated threshold (FIG. 16B). These findings confirm that Rosa26-rtTA; tetO-H2Bj-GFP is an excellent model that can identify somatic label retaining stem cells.

Figure 10C:
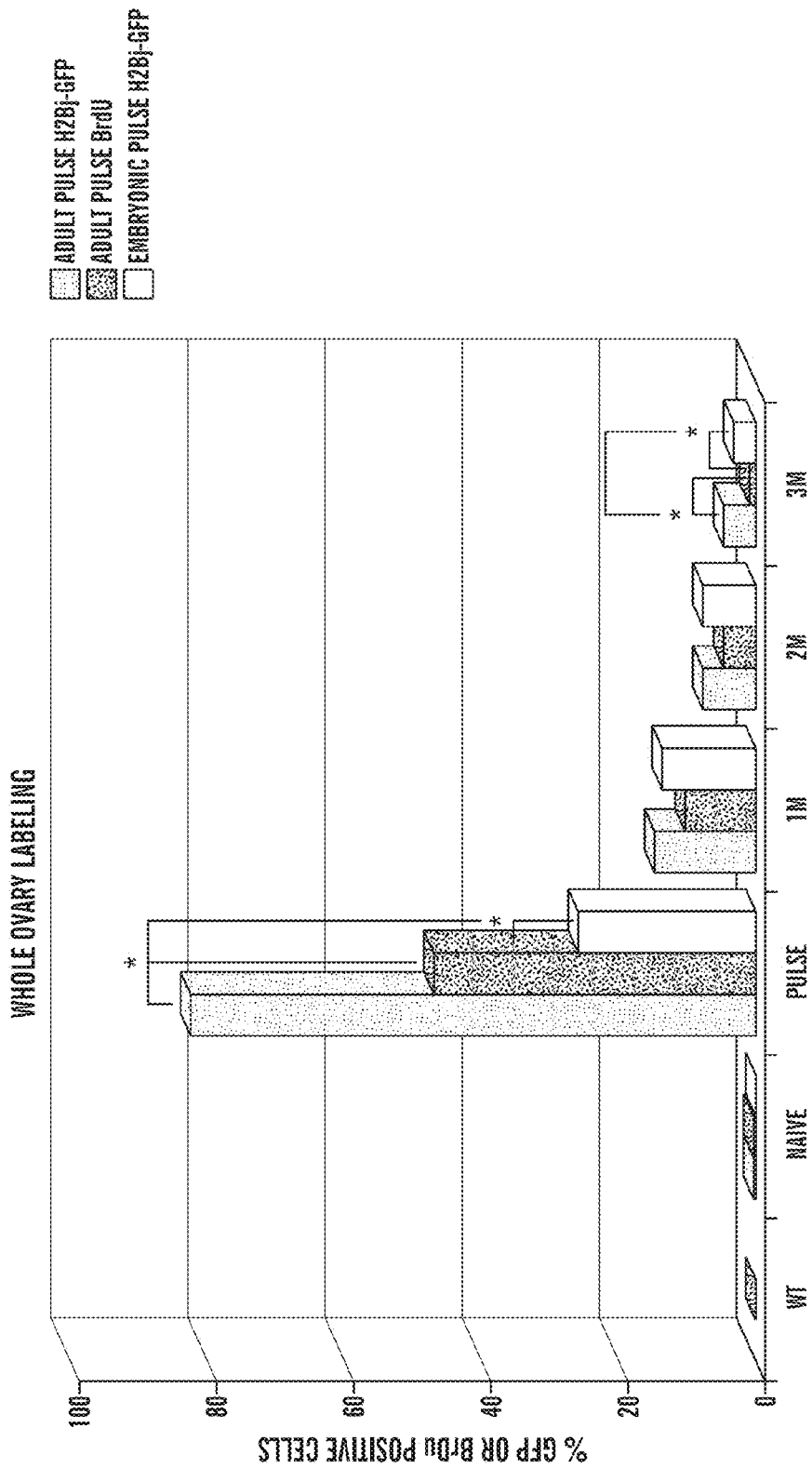
Figure 10D:
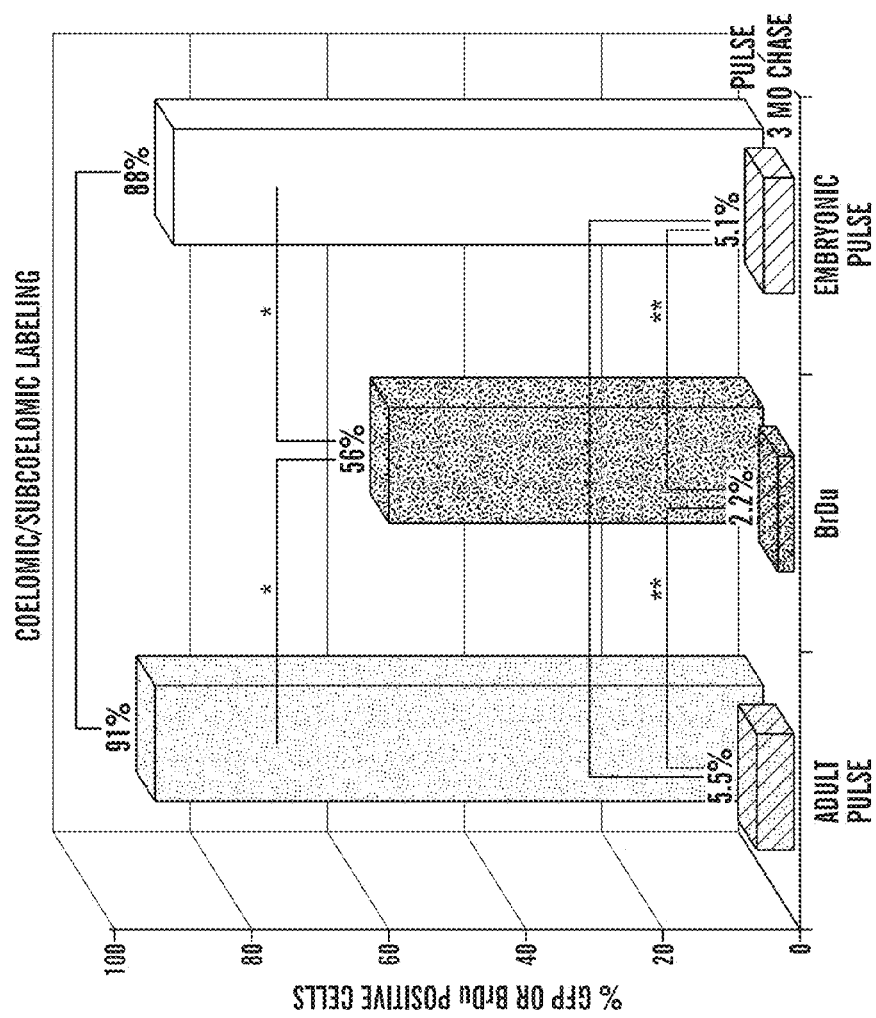

Ovarian GFP and BrdU labeling was evaluated by immunofluorescence and compared with intestine, skin, and brain as positive control tissues (FIG. 17, Brennand et al, 2007). PBS injected (no BrdU) and naive (no doxycycline) Rosa26-rtTA; tetO-H2Bj-GFP mice were used as negative controls (not shown). BrdU and H2Bj-GFP demonstrated labeling in the coelomic, subcoelomic/stromal (FIG. 17 insets), and hilar areas of the ovary during the pulse. Significant variability in initial pulse whole ovary labeling was observed within the H2Bj-GFP labeling method and between the H2Bj-GFP and BrdU methods used in this study (FIG. 10C; adult pulse H2Bj-GFP=82.5±7.9%, adult pulse BrdU=46.9±8.9%, embryonic pulse H2Bj-GFP=26.0±2.5%; p<0.05). Such variability within the H2Bj-GFP labeling technique is likely the result of the visually evident lack of granulosa cell labeling in the embryonic pulse (FIG. 17) and is not observed when the coelomic/subcoelomic labeling is evaluated by segmenting the granulosa and medullary cells out of the analysis (FIG. 10D, detailed below). The difference observed between the BrdU and H2B-GFP pulse labeling methods is likely explained by a shorter labeling period with the BrdU method and potentially the efficiency of delivery/incorporation of the BrdU into dividing progenitor cells. After three months chase there was a significant difference in whole ovary label retention when comparing BrdU to the adult and embryonic pulse H2Bj-GFP labeling methods (FIG. 10C, p=0.016 & p=0.010), but there was no significant difference between the two H2Bj-GFP pulse labeling methods (FIG. 10C, p=0.12). Likewise, quantification of coelomic/subcoelomic (defined as the single layer coelomic epithelium plus the 2-4 cell layer thick region immediately below the coelomic epithelium based on visual segmentation) labeling efficiency demonstrated no significant difference between the two H2Bj pulse periods (FIG. 10D, 91% & 88%, p=0.43), but a significant difference between the two H2Bj-GFP techniques and BrdU was observed (FIG. 10D, p=0.0016 & p=0.00011). Similarly, no significant difference was noted in label retention after three months chase in the H2Bj-GFP animals (FIG. 10D, adult pulse H2Bj-GFP=5±1.1% LRCs, embryonic pulse H2Bj-GFP=3.2±0.2% LRCs, p=0.794) while there remained a significant difference in label retention between the H2Bj animals and the BrdU animals (FIG. 10D, BrdU=2.2±0.4% LRCs, vs adult pulse h2Bj-gfp p=0.021 & vs embryonic pulse H2Bj-GFP p=0.041). The inventors have discovered that both techniques and both pulse periods were able to identify similar sub-populations of LRCs in the adult ovary at the end of the chase period. Furthermore, these cells share label retaining properties similar to those observed in the bone marrow Lin⁻cKit⁺Sca-1⁺ hematopoietic stem cells which serve as a positive control.

Example 9

Identification of Ovarian LRCs

Figure 11A:
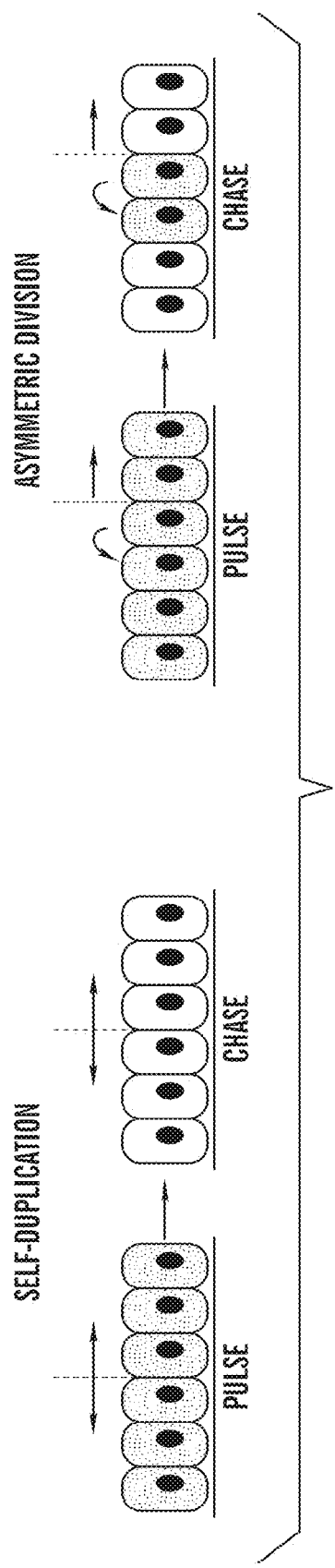
FIGS. 11A-11I show identification of LRC populations in the ovary.
Figure 19:
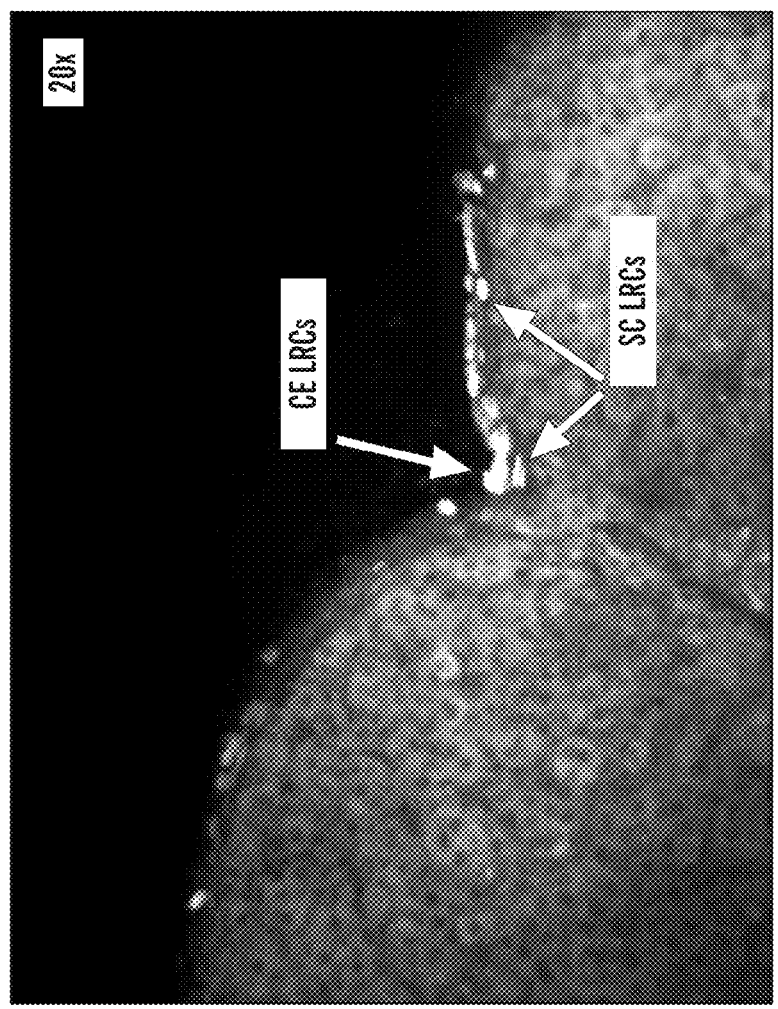
FIG. 19 shows a 3D confocal identification of coelomic and subcoelomic LRCs. Three-dimensional reconstruction of 3 month chase Rosa26-rtTA; tetO-H2B-GFP coelomic and subcoelomic LRCs. This movie demonstrated the relationship of these two populations of cells as well as their location within the interfollicular clefts.

The inventors next evaluated ovaries at various time points in the chase interval of the experiment to determine whether re-epithelialization occurs via progenitor cell proliferation or simple self-duplication. The self-duplication model predicts uniform loss of signal during the chase period while the stem cell asymmetric division model predicts a preferential retention of label in stem/progenitor cells (FIG. 11A). After 3 months chase, gross observation of H2Bj-GFP ovaries demonstrated visually bright LRCs congregating near inter-follicular clefts formed by the ovarian vasculature (FIGS. 11B & 11C; FIG. 19: confocal 3D reconstruction, cross section). BrdU/IdU and H2Bj-GFP (embryonic and adult pulse) labeling techniques both identified label-retaining cells (FIG. 11D, 11E, 11F, 11G, 11H, 11I) in the coelomic epithelium (CE), subcoelomic/stromal (SC; defined as the CD45−/CD31⁻ 1-4 cell layer thick region immediately below the coelomic epithelium plus the stromal tissue of the ovary), and perihilar medullary cells (PHM). BrdU/IdU and H2Bj-GFP combination pulse-chase studies demonstrated colocalization of BrdU/IdU and H2Bj-GFP LRCs in most instances throughout the chase period. These results identify a candidate LRC population representative of a putative stem cell population in perivascular coelomic epithelial clefts capable of functioning in repair after ovulation induced coelomic epithelium damage. In addition, the inventors demonstrate at least two other LRC populations within the ovarian stroma that may represent stem/progenitor cell precursors of other somatic cell types in the ovary.

Example 10

Phenotypic Characterization of Ovarian LRCs in their Microenvironment

To understand better the niche microenvironment responsible for preserving the undifferentiated state and to characterize the surface marker expression of the identified LRC populations, the inventors evaluated a series of known stem, epithelial, mesenchymal, cell-cell adhesion, germ, and ovarian cancer cell markers. These markers and findings are summarized in Table 4 and detailed below.

TABLE 4

Summary of LRC surface marker expression.

| Antigen | CE | SC | PHM | Hu Ov* | Ov CA* |
|---|---|---|---|---|---|
| CD3 (T3) | − | − | − | NR | NR |
| CD4 (T4) | − | − | − | − | − |
| CD11b (Mac-1) | − | − | − | − | − |
| CD19 (B4) | − | − | − | NR | NR |
| CD23 (Ly-42, B6) | − | − | − | − | − |
| CD25 (IL-2Rα) | − | − | − | − | − |
| CD31 (PECAM-1) | − | − | − | + | − |
| CD34 (gp105-120) | − | +/− | − | + | − |
| CD44 (Hermes, Pgp-1) | − | +/− | + | − | + |

TABLE 4-continued

Summary of LRC surface marker expression.

| Antigen | CE | SC | PHM | Hu Ov* | Ov CA* |
|---|---|---|---|---|---|
| CD45 (CLA) | − | − | − | − | − |
| CD49b(Pan-NK) | − | − | − | − | NR |
| CD61 (integrin β3) | − | − | − | + | + |
| CD62 (E-Selectin) | − | − | − | − | − |
| CD90 (Thy-1) | − | +/− | − | + | + |
| CD105 (Endoglin) | − | + | + | + | + |
| CD117 (c-Kit) | − | − | + | − | − |
| CD133 (AC133) | − | − | − | NR | NR |
| CD140b (PDGFRb) | − | + | − | + | + |
| CD309 (Flk-1, VEGFR2) | − | − | − | − | − |
| CD324 (E-Cadherin) | + | − | − | + | + |
| CD326 (EpCam) | − | − | − | − | + |
| Cytokeratin 8 (Troma-1) | + | − | − | + | + |
| Beta-Catenin | + | − | − | + | + |
| α-SMA | − | +/− | − | + | + |
| Lineage | − | − | − | + | NR |
| NG2 | − | +/− | − | + | + |
| Gata-4 | + | − | + | + | NR |
| Met | − | + | + | + | + |
| Vimentin | + | + | + | + | + |
| SF-1 | − | − | + | + | − |
| p16 INK4A | + | − | + | − | + |
| Connexin 43 | − | − | − | + | Dec/− |
| VASA | − | − | − | + | − |
| Oct-4 | − | − | − | − | NR |
| Era | + | + | + | + | +/− |
| Collagen IV | + | − | − | + | + |
| PTEN | + | − | + | + | + |
| PI3K | + | − | − | + | + |
| Notch-1 | − | − | − | − | Dec/− |

CE = Coelomic epithelial label retaining cells; SC = Subcoelomic label retaining cells, PHM = Peri-hilar medullary label retaining cells;
"*"= Hu Ov (human normal ovary) and OvCa (ovarian cancer) expression patterns were obtained from the Human Protein Atlas tissue arrays (www.proteinatlas.org).
"−" = no expression; "+" = positive expression in the ovary; "+/−" variable expression; "Dec/−" = decreased or negative expression; NR = not reported in literature.

Coelomic LRCs.

Immunofluorescence demonstrated that coelomic LRCs express cytokeratin 8, β-catenin, dim and E-cadherin (data not shown) (Table 4), and are negative for EpCam (data not shown). In addition, coelomic LRCs were negative for the pan-hematopoietic marker CD45 and the endothelial marker CD31 (Table 4 and data not shown). These cells also labeled for Collagen IV, PTEN, Vimentin, Gata-4, and PI3K (Table 4). Characterization of the coelomic LRC niche microenvironment demonstrated a close association with the immediately adjacent perivascular subcoelomic/stromal LRCs and non-LRCs. The inventors did not observe a surface marker in this study that was unique to coelomic LRCs. Thus, coelomic LRCs express known markers of epithelial cells and their perivascular microenvironment is made up of subcoelomic/stromal LRCs and non-LRCs that express classical stromal markers as detailed below.

Subcoelomic/Stromal LRCs. Subcoelomic/stromal LRCs were discovered predominantly immediately below the coelomic epithelium and adjacent to CD31⁺ endothelial cells (data not shown) where they expressed varying degrees of the stromal markers NG2$^{+/-}$, PDGFRb⁺, Thy-1$^{+/-}$, CD44$^{+/-}$, and αSMA$^{+/-}$ (data not shown and Table 4). In addition, these LRCs were negative for cKit receptor, cytokeratin 8, β-Catenin, and E-cadherin (data not shown and Table 4). The inventors observed that the visual epifluorescent intensity of Thy-1 and NG2 increased as the subcoelomic/stromal LRCs and their progeny incorporated into the growing follicle in association with the developing follicular capillary network. Since cells derived from the bone marrow are known to express these stromal/pericyte/fibroblastic markers, the inventors performed parabiosis and bone marrow transplantation experiments as detailed below in an effort to identify their derivation.

Perihilar Medullary LRCs

Immunofluorescence of PHM GFP+ LRCs revealed that these cells also reside immediately adjacent to CD31+ endothelial cells in a perivascular niche (FIG. 19I), which is bounded by α-SMA (Table 4). However, in direct contrast to subcoelomic/stromal LRCs, PHM LRCs express the theca cell markers c-Kit, SF-1, and Gata-4 (data not shown). These LRCs with the marker expression profile of these cells were observed to incorporate into the developing theca layer at all chase intervals examined. A detailed surface marker profile is provided in Table 4 and the origin of these cells was determined by parabiosis and irradiation experiments as detailed below. Coelomic LRCs express the epithelial markers Cytokeratin-8, β-Catenin and are E-Cadherin$^{Dim}$/EpCam$^-$ expression profiles are shown in Table 4. Subcoelomic/stromal LRCs lie immediately adjacent to CD31+ endothelial cells (data not shown), are variably positive for NG2, PDGFRb, Thy-1, CD44 (C-G), α-SMA (Table 4), and are negative for cKit (data not shown). The peri-vascular niche microenvironment of coelomic and subcoelomic/stromal LRCs was also studies (data not shown). Perihilar Medullary LRCs also reside in a perivascular niche immediately adjacent to CD31+ endothelial cells (data not shown) but, in contrast to subcoelomic LRCs, they express the theca cell markers c-Kit, Gata-4, and SF-1 (data not shown) demonstrating a potential population of theca progenitor cells. These findings demonstrate that PHM LRCs may serve as a progenitor cell population for this cell production during follicle maturation.

To complete the niche description, the inventors investigated the relationship of germ cells to the identified LRCs. The inventors observed that VASA (Table 4) positive germ cells and primordial follicles reside within the perivascular coelomic/subcoelomic LRC niche described in detail above, but did not co-localize with H2Bj-GFP or BrdU at any time during the pulse or the chase. GFP stained germ cells were not found in actin-GFP bone marrow recipient animals or after parabiosis using either an actin-GFP or an ubiquitin-GFP donor (as described herein in Example 11).

Example 11

Parabiosis and Irradiation with β-Actin GFP Bone Marrow Transplantation

Figures 12A, 12B:
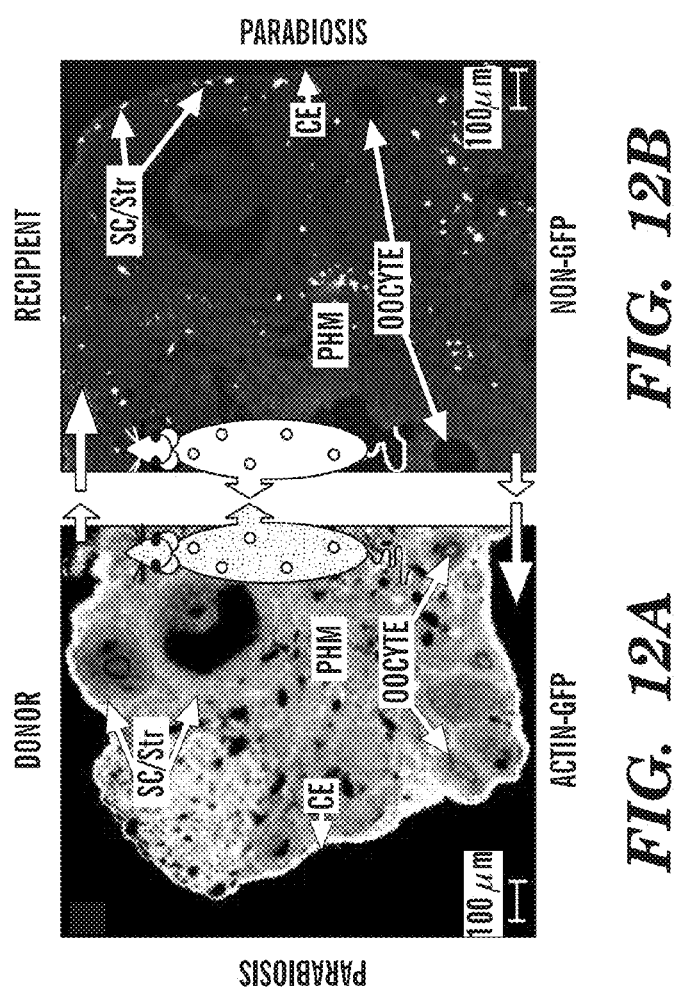
FIGS. 12A-12H show phenotypic characterization of ovarian LRCs and their niche. Parabiosis studies between actin-GFP positive and negative isogenic littermates (panel 12A & 12B) demonstrated no incorporation of GFP into the coelomic epithelium (panel 12C). Variable co-localization of sub-coelomic/stromal LRC markers such as PDGFRb, NG2, CD44, and CD105 with actin-GFP positive cells suggests an extrinsic source of these cells such as the circulation/bone marrow (panels 12C-12H). No co-localization of actin-GFP with c-KIT was observed demonstrating that PHM are not circulatory/bone marrow derived.
Figure 12C:
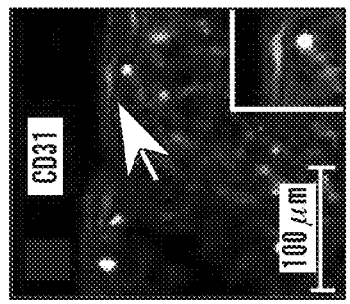
Figure 12D:
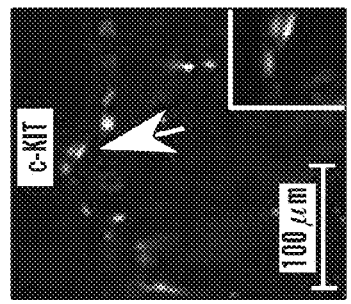
Figure 12E:
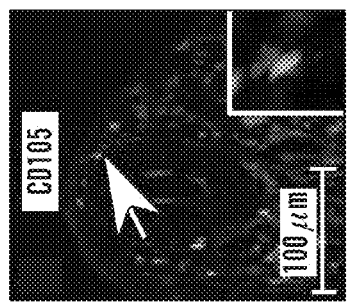
Figure 12F:
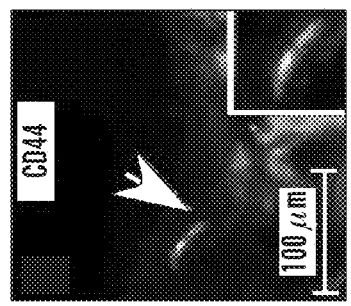
Figure 12G:
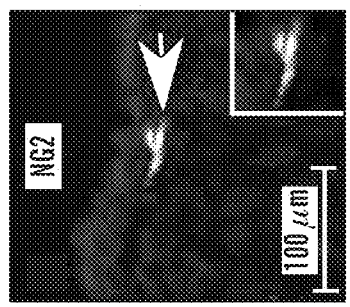
Figure 12H:
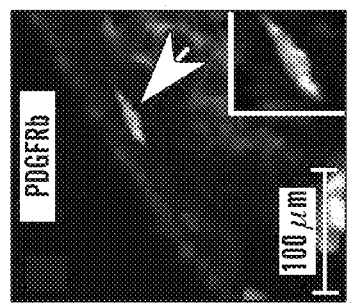

Immunofluorescent characterization of the identified LRC populations, as detailed above, led the inventors to investigate whether these populations are exclusively intrinsic within the mouse ovary or are derived from an extrinsic source such as the circulation or bone marrow. The inventors performed 1) parabiosis between isogenic actin-GFP or ubiquitin-GFP mice and wild type littermates (actin-GFP n=6 pairs, ubiquitin GFP n=4 pairs), 2) parabiosis from actin-GFP mice into wild type isogenic recipients treated with cytoxan/busulfan to produce ovarian injury by chemoablation (n=6), and 3) irradiation plus isogenic β-actin GFP bone marrow transplantation (n=4), to investigate whether GFP positive circulation/bone marrow derived cells expressing any of the three LRC marker profiles as defined above, appeared in the non-GFP ovaries. Hematoxylin and eosin staining of ovary sections from all three conditions demonstrated a loss of stromal tissue architecture (data not shown). After irradiation, near complete replacement of the remaining scared ovarian tissue with GFP+/CD45+ circulation/bone marrow derived cells was observed (data not shown). The inventors did not observe incorporation of GFP into the coelomic epithelium or co-localization of actin-GFP with c-Kit positive perihilar medullary cells in any of these models (FIG. 12H and data not shown). The inventors also did observe a loss of peri-hilar SF-1$^+$/Gata-4$^+$/c-Kit$^+$ cells in both the Cytoxan/Busulan treated parabiotes and in the irradiated transplant animals without rescue by circulating/bone marrow derived actin-GFP cells. The results demonstrate that these cells are intrinsically replenished/maintained and not constitutively rejuvenated from a bone marrow/circulating source in response to various modalities of injury or the ovarian cycle. Conversely, GFP$^+$ cells were observed to co-localize in all three models with the markers that the inventors discovered were characterized as the subcoelomic/stromal LRCs, namely, CD44, PDGFRb, NG2, CD105, and Thy-1 to varying degrees suggesting that these cells may be derived from a circulating/bone marrow reservoir (depicted in FIG. 12C, 12D, 12F, 12G and data not shown). Thus, the inventors findings demonstrate by phenotypic marker profile that coelomic and PHM LRCs are likely of intrinsic origin while subcoelomic/stromal LRCs are potentially of extrinsic circulatory/bone marrow origin.

Example 12

LRCs Replicate in Response to Estrus Cycling In Vivo

Figure 13B:
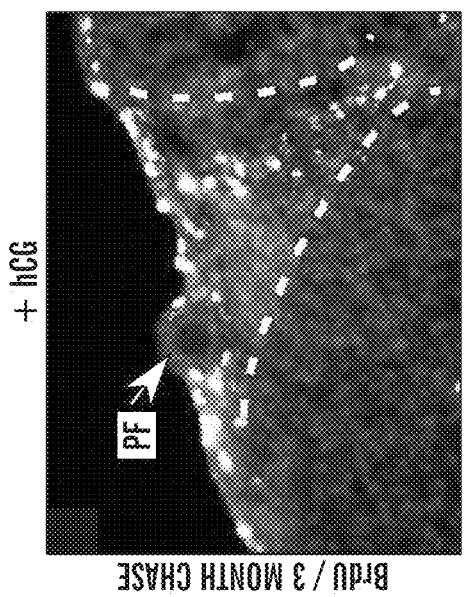
FIG. 13A-13B show LRCs replicate in response to the estrus cycle in vivo. Superphysiologic hCG stimulation of BrdU labeled 3 month chase mice demonstrated increased BrdU signal in the coelomic and subcoelomic/stromal LRCs as compared to unstimulated 3 month chase mice (panel 13A & 13B). PF=Primordial Follicle, CL=Corpora Lutea, GFP=H2Bj-GFP, IdU=iodo-deoxy-uridine, A & B=20×, C & D=10×, E & F=40×. Images representative of n=4.
Figure 13A:
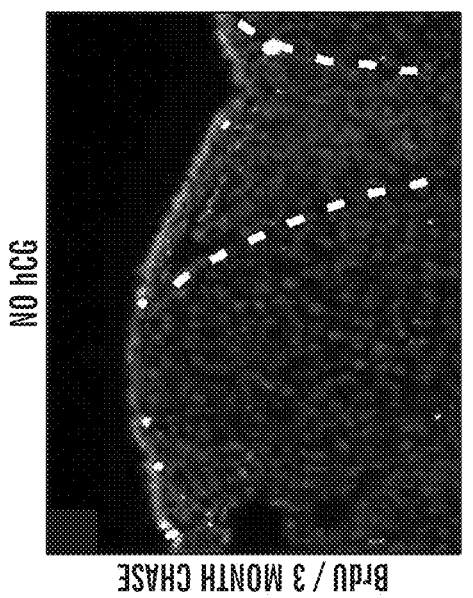

In vivo coelomic label retaining cell response to estrus cycling is necessary to confirm their identity as functional candidate stem/progenitor cells. To assess this response, the inventors used both superphysiologic hCG stimulation and simple estrous cycle staging, in combination with short 2-4 h pulses of i.p. injected IdU. Prior to hCG stimulation, two proestrous chase week 12 BrdU mice were sacrificed to determine the level of prestimulation BrdU (FIG. 13A). Proestrous chase week 12 BrdU mice were then hyperstimulated (n=10) by injection of 10 Units hCG and sacrificed in late estrous/early metestrous, revealing increased BrdU labeling in the coelomic and subcoelomic niches (FIG. 13B). These findings demonstrate that there is increased proliferation within the coelomic and subcolomic niches in response to the estrus cycle.

To confirm these findings and determine if LRCs replicate in vivo without artificial superphysiologic hyperstimulation, the inventors performed short 2-4 h pulse injections of IdU/BrdU in three-month chase H2Bj-GFP mice to asses for colocalization of BrdU/IduU and H2Bj-GFP LRCs. Pre-ovulatory or post-ovulatory (as defined in short-term BrdU experiments above) Rosa26-rtTA; tetO-H2Bj-GFP week 12 chase mice were timed by vaginal cytology and injected with IdU 2-4 h prior to sacrifice in order to identify actively mitotic cells. Response of H2Bj-GFP LRCs to the estrus cycle was evaluated with a short 2-4 h pulse injection of IdU in 3 month chase H2Bj-GFP animals (data not shown). In pre-ovulatory ovaries, IdU was observed only in proliferating granulosa cells (GC) while non-proliferating subcoelomic/stromal LRCs were observed in association with primordial follicles (data not shown). In post-ovulatory animals, IdU was observed to co-localize with coelomic and subcoelomic LRCs (data not shown) demonstrating that these LRCs are functionally responsive to the estrus cycle. Subcoelomic LRCs were observed to co-localize with IdU immediately adjacent to additional proliferating IdU cells that appear to be associating with the developing follicle (data not shown). Coelomic LRCs were observed to co-localize with IdU on either side of the re-epithelializing ovulation wound (data not shown). Preovulatory ovaries demonstrated GFP cuboidal coelomic LRCs and subcoelomic LRCs in their characteristic intrafollicular perivascular niche, but BrdU was only incorporated in granulosa cells during this phase (data not shown). In addition, the inventors observed the close association of subcoelomic LRCs with a developing primordial follicle (data not shown). Postovulatory ovaries demonstrated flattened coelomic and subcoelmic LRCs of varying GFP intensity that appeared in close proximity to both newly formed corpora lutea and in close association with a developing primary follicle (data not shown). Closer inspection revealed that both coelomic and subcolomic LRCs are mitoticaly active in response to the estrus cycle as demonstrated by colocalization of IdU and H2Bj-GFP LRCs (data not shown). In addition, the inventors discovered IdU incorporation and co-localization with GFP on either side of the repairing epithelium demonstrating that there is a combination of stem/progenitor replication followed by daughter cell symmetric replication and migration (data not shown). These findings demonstrate that both coelomic and subcoelomic LRCs are responsive to the estrus cycle and appear to supply daughter cells for reepithelialization and possibly folliculogenesis, respectively.

Example 13

In Vitro Isolation and Characterization of Coelomic LRCs

Figure 14A:
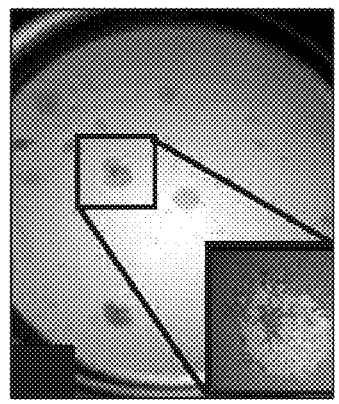
FIGS. 14A-14D show in vitro isolation and characterization of coelomic LRCs by colony forming unit (CFU) assay. Rosa26-rtTA; tetO-H2Bj-GFP coelomic epithelium was harvested and plated in proprietary colony forming unit assay media for 14 days. Giemsa staining identified macroscopic and microscopic colony formation (panel 14A & inset). H2Bj-GFP LRCs were observed to form a three-dimensional sphere-like structure near the center of GFP positive colonies at each pulse-chase interval (panel 14B, 14D, and FIG. 20 (see below)). Panel 14C demonstrates that an average of 10±5 CFUs (n=9) are generated per $1\times10^4$ cells plated and that a visually estimated 30% of the colonies are GFP positive. The percentage of GFP+CFUs (panel 14C) formed at each pulse-chase interval was independent of the percentage of GFP labeled cells per $1\times10^4$ cells plated demonstrating a constant initial labeling efficiency of candidate stem cells and that these cells retain label with prolonged chase. Quantification of signal loss with replication demonstrated an exponential loss of signal as a function of distance from the brightest LRCs (panel 14D, inset) demonstrating asymmetric replication.
Figure 14B:
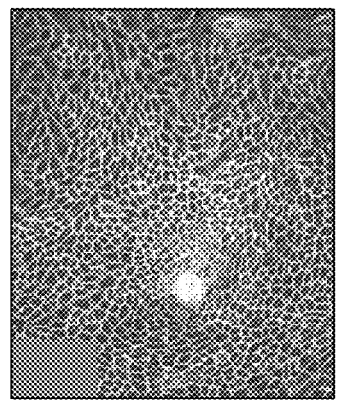
Figure 14C:
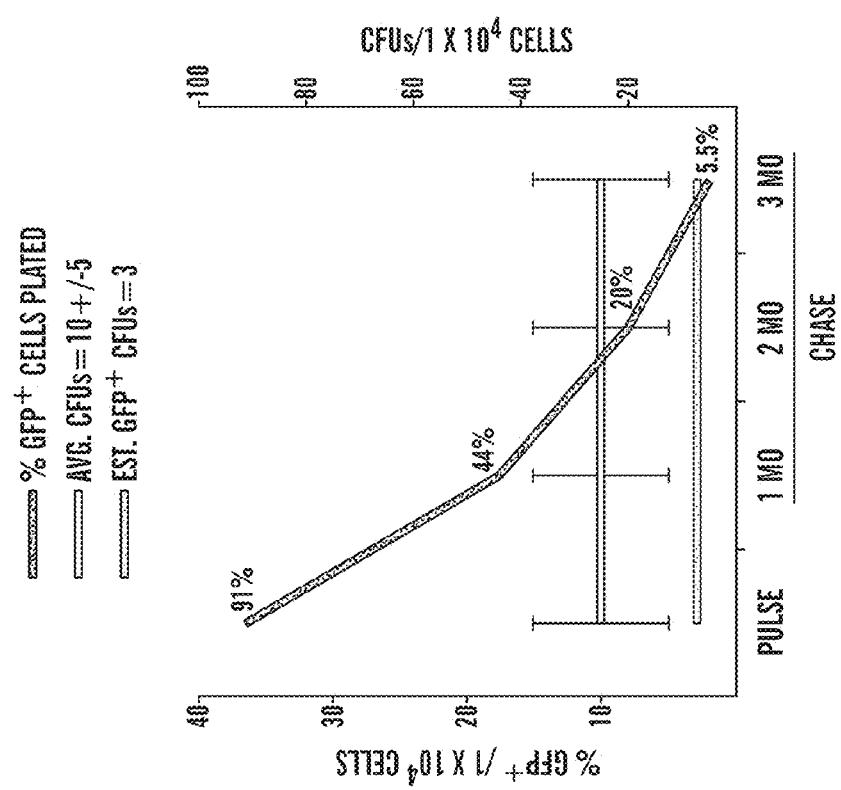
Figure 14D:
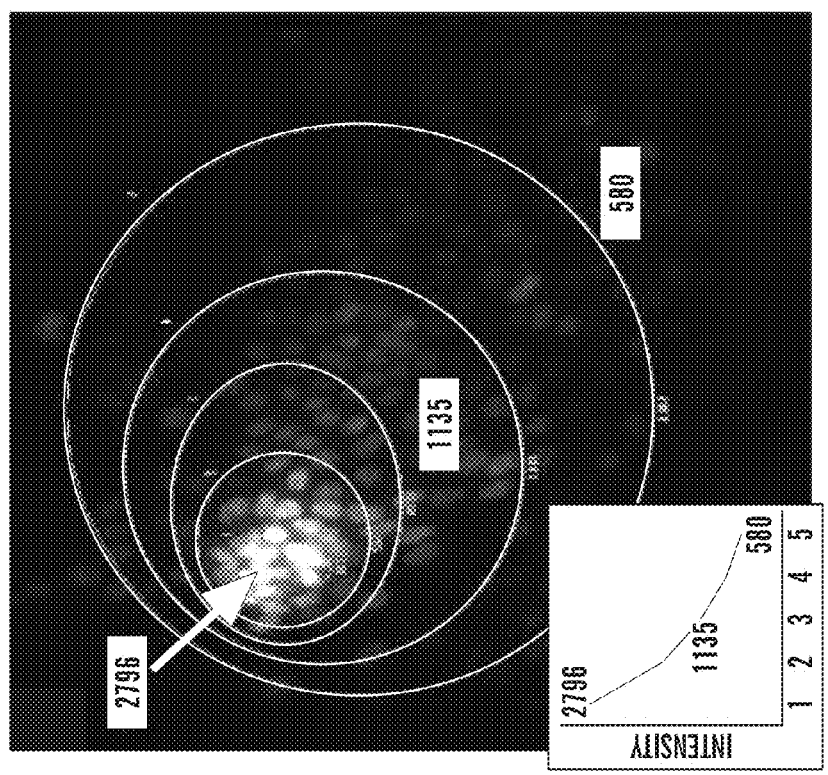
Figure 20:
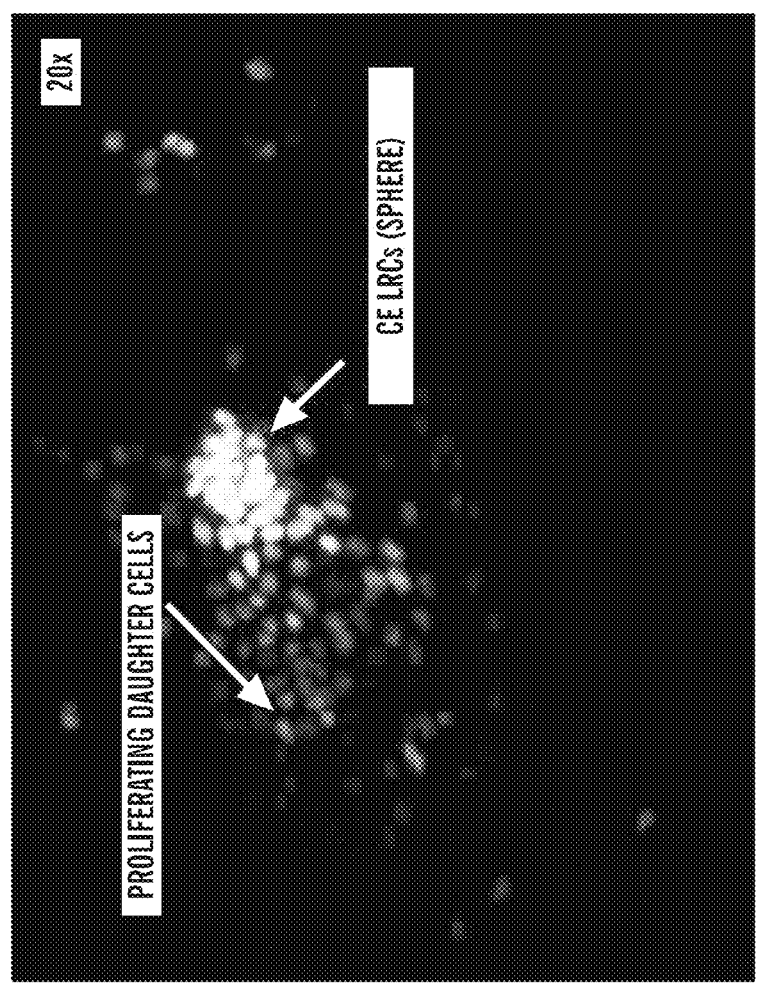
FIG. 20 shows a 3D confocal reconstruction of in vitro CFU isolated coelomic LRC sphere. Three-dimensional reconstruction of 3 month chase Rosa26-rtTA; tetO-H2B-GFP coelomic LRCs isolated by colony forming unit demonstrate a three-dimensional spheroid LRC (bright) population surrounded by proliferating daughter cells that lose the H2B-GFP label.

A mesenchymal stem cell colony forming unit (CFU) assay was used to select ovarian coelomic epithelial stem cells capable of generating characteristic colonies. Rosa26-rtTA; tetO-H2Bj-GFP coelomic epithelial cells released by collagenase treatment were plated and, after 14 days incubation, the average number of Giemsa stained colonies (FIG. 14A) was determined to be $10\pm5$ CFU's per $1\times10^4$ plated cells (n=9) independent of pulse-chase status. These findings indicate there are a constant number of stem/progenitor cells yielding a constant number of colonies after inoculation of $1\times10^4$ coelomic epithelial cells. The percentage of GFP positive colonies (FIG. 14B) was visually estimated at about 30% of the colonies independent of pulse-chase status indicating there is a constant number stem/progenitor cells labeled during the pulse and that these cells retain their label and colony forming ability throughout the chase period (FIG. 14C). Using the BD Pathway live confocal microscope, the inventors discovered that the H2B-GFP LRCs form spheres that settle and maintain a three-dimensional sphere structure as their symmetrically dividing daughter cells replicate away from the LRC nidus and dilute out the GFP signal, (FIG. 14B, 14D and FIG. 20). Quantification of GFP signal intensity loss with replication was determined to be exponential and a function of distance from the brightest LRC at all pulse-chase time points (FIG. 14D).

To confirm the identity of CFU isolated LRCs as coelomic epithelial cells, the inventors analyzed them for expression of the surface markers identified in tissue sections. Phenotypic analysis of LRC colonies demonstrated that they are positive for the same markers as were observed in tissue sections, such as cytokeratin 8, E-cadherin, vimentin and β-catenin (data not shown). In addition, the inventors did not observe expression of αSMA or c-Kit (data not shown) in these cells, confirming that they were not contaminated by subcoelomic or perihilar medullary LRCs, but that the collagenase treatment of the ovary selected predominantly for the coelomic epithelial cells. These findings demonstrate that CFU assay can be used to isolate candidate normal ovarian coelomic stem cells in vitro and that the Rosa26-rtTA; tetO-H2Bj-GFP model appears to mark putative progenitor cells in vivo and in vitro.

Example 14

Enrichment of Coelomic Epithelial SP Cells by H2B-GFP LRCs

Figure 15B:
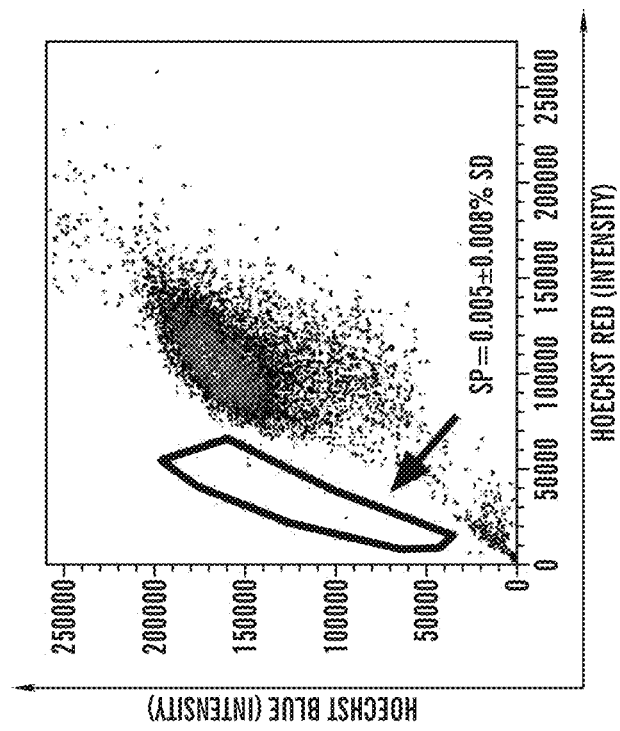
FIGS. 15A-15D shows enrichment of coelomic epithelial SP cells by H2B-GFP LRCs. Rosa26-rtTa; tetO-H2Bj-GFP coelomic epithelial cells were harvested as described and analyzed for the presence of side population. Normal mouse coelomic epithelial cells demonstrate a verapamil-sensitive SP (panel 15A & 15B; 2.46±0.27% SD; n=6). Wild type coelomic epithelial cells were used to establish a $GFP^+$ gate of intensity $\geq 10^2$ and a $GFP^{Bright}$ LRC gate of intensity $\geq 10^3$ (panel 15C). 56.5±4.1% SD (panel 15C; n=3) of SP cells were $H2Bj-GFP^+$ and 67.7±8.1% SD of $H2Bj-GFP^+/SP^+$ cells were $H2Bj-GFP^{Bright}$/LRCs (panel 15D).
Figure 15A:
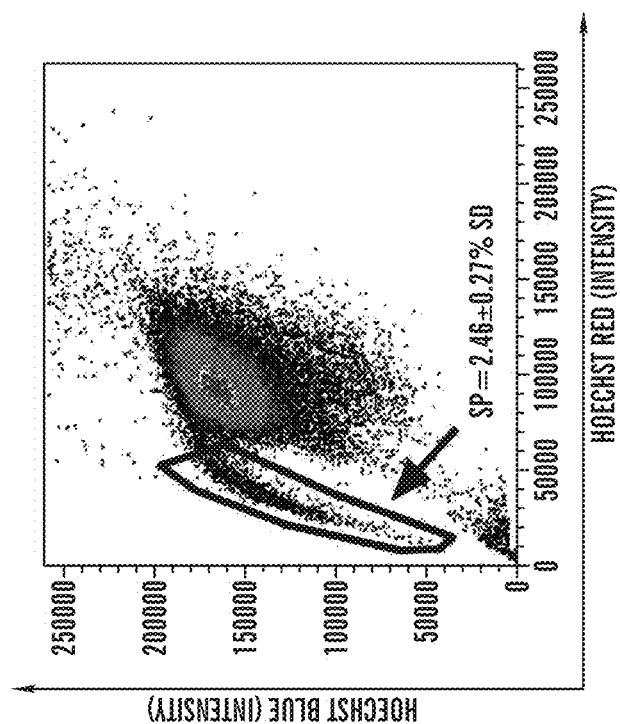
Figure 15C:
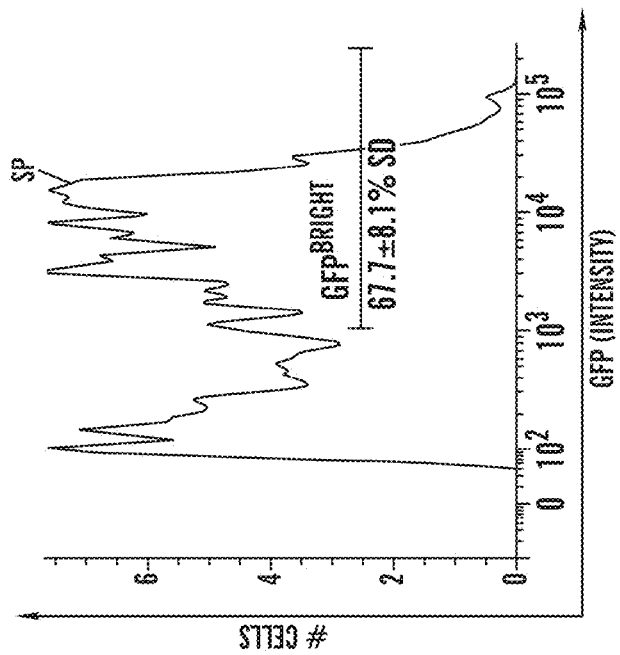
Figure 15D:
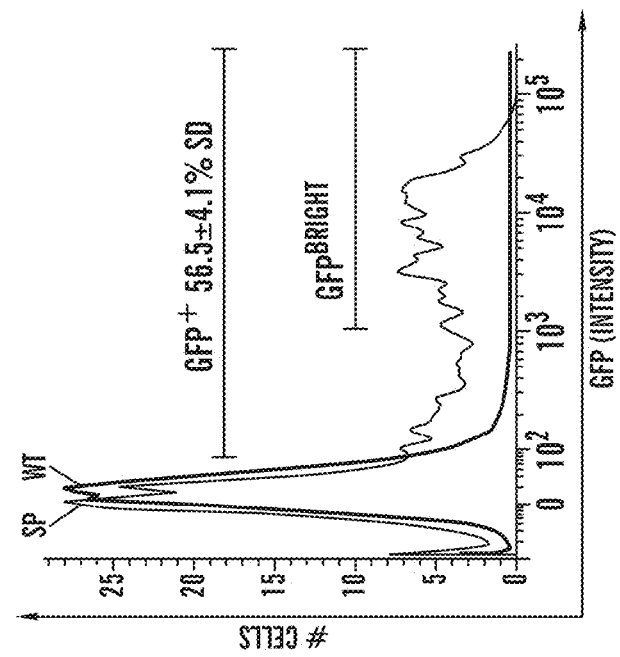
Figure 17C:
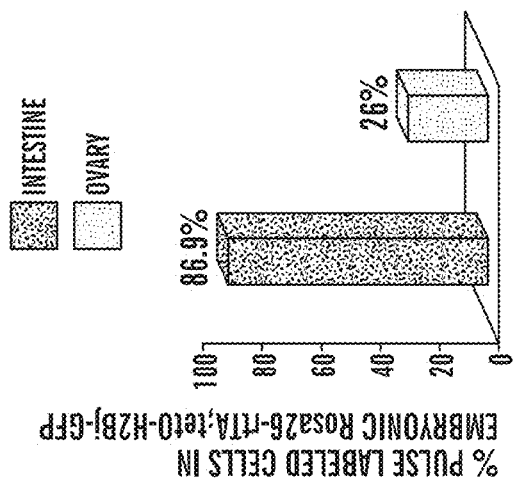
FIGS. 17A-17I shows ovarian Pulse Labeling Efficiency. To evaluate the ability of the two labeling methods used in this study, the inventors compared the labeling efficiency in the ovary to that of the positive control intestine. By visual inspection (panels 17A-17B, 17D-17E, 17G-17H) and quantification (panels 17C, 17F and 17I) the inventors demonstrated that the pulse labeling efficiency of the ovary (panel 17G-17H & 17I) appears similar and adequate as compared to the known positive control intestine (panels 17A-17B & 17F) for both H2Bj-GFP labeling methods. The BrdU labeling in the ovary appeared to be low in comparison to the intestinal pulse labeling (FIGS. 17C, 17I). Thus, the inventors chose to move forward with the two H2B-GFP models.
Figure 17B:
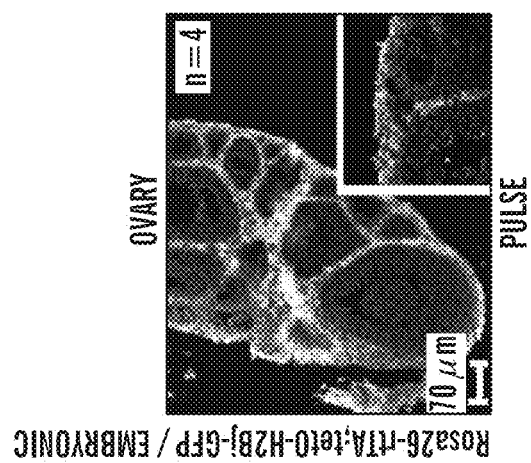
Figure 17A:
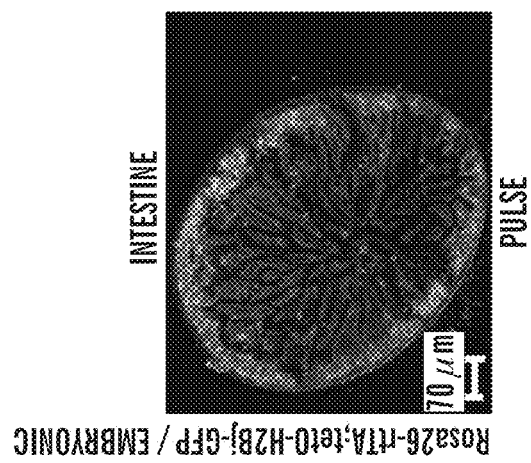
Figure 17D:
Figure 17E:
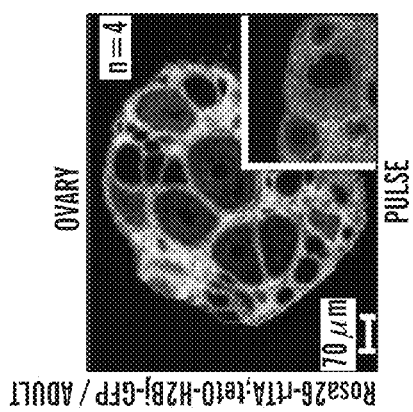
Figure 17F:
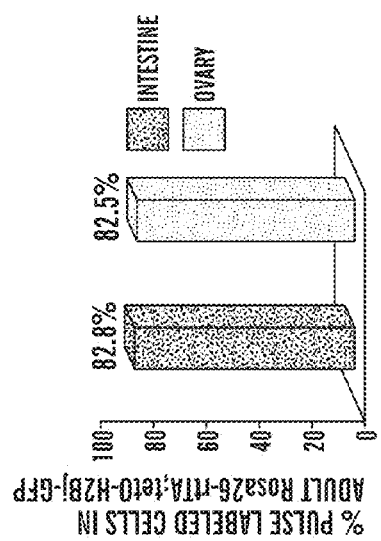
Figure 17G:
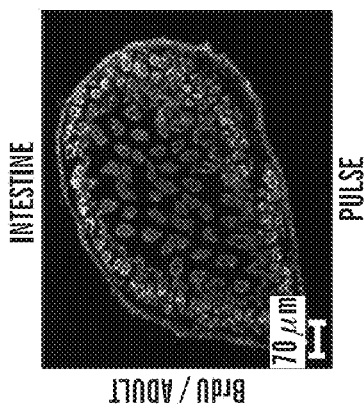
Figure 17H:
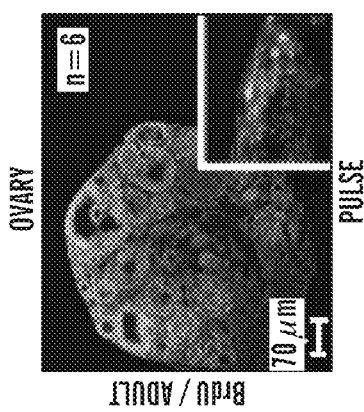
Figure 17I:
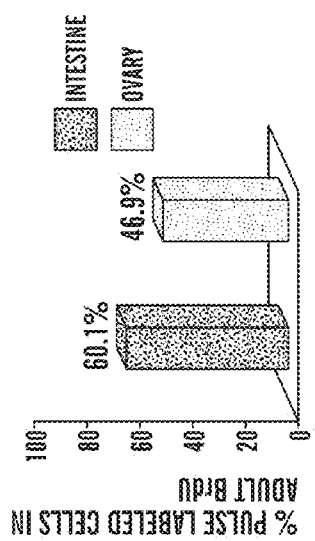

Based on our previous findings that ovarian cancer stem cells can be detected in a verapamil-sensitive Hoechst effluxing SP (Szotek, et al. 2006), the inventors assessed if the normal coelomic epithelium possessed a similar SP and that these SP cells might co-localize with coelomic LRCs. Chase 1 month and 2 month H2Bj-GFP coelomic epithelial cells were isolated, harvested, and subjected to SP analysis (Szotek et al., 2006) as previously described (1 month n=3 animals, 2 month n=3, 3 month n=1). SP analysis clearly identified a verapamil-sensitive side population (FIG. 15A, SP=2.46±0.27%-SD, n=6 compared to FIG. 15B, +Verapamil % SP=0.005±0.008%-SD, n=6) within the normal coelomic epithelium in adult H2Bj-GFP mice. GFP intensity gates were set using wild type $GFP^-$ epithelial cells to define the $GFP^+$ gate as intensity $\geq 10^2$ and the $GFP^{bright}$ LRC gate as an intensity $\geq 10^3$ (FIG. 15C). Evaluation of 2 month chase SP cells for GFP expression demonstrated that 56.5±4.1% SD of $SP^+$ cells are $H2Bj\text{-}GFP^+$ (FIG. 15C; n=3) and 67.7±8.1% SD (FIG. 15D, n=3) of those $SP^+/H2B\text{-}GFP^+$ are classified as $GFP^{bright}/LRCs$. Thus, the inventors demonstrate in these studies validate that SP can be used as a workable surrogate to identify LRCs with stem cell-like characteristics within the coelomic epithelium of normal mouse ovary and, by extension, in tumor populations.

The inventors also discovered coelomic epithelial LRCs do not express EpCam. The inventors used immunofluorescence to determine if the reported ovarian cancer cell marker EpCam is expressed on LRCs. The inventors did not observe expression of EpCam on the mouse ovarian surface epithelium but it was clearly expressed on the fallopian tube epithelium (not shown) and the uterine epithelium (data not shown). To confirm the discovery that the subcoelomic/stromal LRCs are likely bone marrow derived and that the coelomic and perihilar-medullary cells are likely not circulatory/bone marrow derived, the inventors tested whether chemo-ablation of the germ cells using Cytoxan/Busulfan or irradiation followed by actin-GFP bone marrow transplantation would stimulate an otherwise extremely rare event to occur. H&E sections demonstrated that the ovarian stroma of the Cy/Bu treated parabiosis mice and the irradiated GFP-bone marrow transplanted mice is significantly altered over that of wild type or non-treated parabiosis mice (data not shown). Surface marker profiling of Cy/Bu treated parabiosis ovaries and irradiated bone marrow transplant ovaries demonstrated co-localization of actin-GFP with the markers used to identify subcoelomic/stromal LRCs confirming that these cells are likely bone marrow derived (data not shown). At no time did we see incorporation of GFP into the coelomic epithelium or co-localization with cytokeratin 8 in the coelomic epithelium; however, the inventors did note loss of cytokeratin 8 expression and gain of αSMA expression in the irradiated mice (data not shown). The inventors did not observe the presence of $cKit^+/Gata\text{-}4^+/SF\text{-}1^+$ perihilar medullary cells in either model suggesting that these cells are not bone marrow derived and are likely dependent on the presence of germ cells for maintenance of their progenitor pool. The inventors also discovered that the ovarian stroma is almost completely replaced by $CD45^+/Lineage^+$ cells and that the vasculature appears atrophic in the irradiated mice.

The inventors also performed 3D confocal reconstruction of LRC perivascular niche. Three-dimensional reconstruction of 3 month chase Rosa26-rtTA; tetO-H2B-GFP coelomic and subcoelomic LRCs within their perivascular niche. Coelomic H2B-GFP LRCs (Green) appear to reside just superficial to the subcoelomic LRCs and the subcoelomic LRCs appear to lie directly in contact with the ovarian vasculature stained with CD31 (data not shown).

The hypothesis that rare "embryonic rests" are responsible for malignancy was suggested >100 years ago (24), but recent advances in somatic stem cell identification has rejuvenated research in this area (28-29). The unique asymmetric self-renewal capacities of somatic stem cells make it plausible and probable that mutations in these cells are perpetuated and over time lead to malignancy. Like somatic stem cells, cancer stem cell populations have the properties of self-renewal, heterologous descendent cells, slow cell-cycle times, and, unlike somatic stem cells, enriched tumor formation (8, 24). Herein, the inventors have discovered these properties within a subpopulation of mouse ovarian cancer cells that were isolated by SP sorting. The inventors have discovered MOVCAR7 and 4306 SP cells are able to self-renew and produce heterologous descendent NSP cells in culture, MOVCAR 7 SP cells are predominantly $G_1$ cell cycle arrested, and the in vivo time to appearance of tumors in animals injected with equal numbers of MOVCAR 7 cells may be shorter in those receiving SP cells. The inventors discovered that appearance of tumors in NSP-injected animals occurred at the same time as animals injected with unsorted cells possessing approximately the same number of SP cells. Thus, the inventors have discovered that isolated mouse SP cells posses the properties ascribed to cancer stem cells, and only a low number of these SP cells is required to initiate tumor formation in vivo, thus the inventors have discovered a new model for human ovarian cancer.

Ovarian cancer patients initially respond well to surgical cytoreduction and chemotherapy. Chemotherapy alone can yield several logs of tumor cytoreduction but seldom a cure. The majority of patients who respond to primary chemotherapy ultimately develop recurrent, usually drug-resistant, disease that is conceivably due to the ability of ovarian cancer stem cells to escape these drugs. BCRP1, otherwise known as the ABCG2 transporter, confers the ability to not only define a stem cell-like Hoechst 33342-excluding SP but, perhaps more importantly, the drug resistance-associated efflux of many lipophilic chemotherapeutic agents such as mitoxantrone, daunorubicin, doxorubicin, indolcarbazole, and others (22). Herein, the inventors demonstrate that candidate mouse ovarian cancer stem cells, defined as Hoechst-effluxing, verapamil-sensitive, and BCRP1$^+$ SP cells, are more resistant to doxorubicin, confirming these stem cell-like characteristics as a potential mechanism for drug resistance. In addition, the inventors have identified a similar subpopulation of cells in both human ovarian cancer cell lines and primary human ascites cells that could be defined as Hoechst-effluxing, verapamil-sensitive, BCRP1$^+$ SP cells. The inventors have discovered that BCRP1 and ability to exclude lipophilic molecules can be used as "markers" to detect and isolate patient primary ovarian cancer stem cells for further characterization.

The inventors have discovered that a subpopulation of cells found in the mouse SPs demonstrate some of the properties of cancer stem cells. The inventors have also discovered the expression of the drug-resistance transporter BCRP1 or other multidrug-resistance proteins (30-33) in these cells, which can have a profound impact on selection of individual treatment strategies, clinical outcome, and the design or selection of the next generation of chemotherapeutic agents. For example, MIS inhibits human anchorage-independent Mullerian tumors in soft agarose (34). The inventors have discovered herein that MIS also acts on cancer stem cell-like populations. The inventors demonstrate that MIS inhibits MOVCAR 7 SP cells in vitro. The inventors have discovered therefore that suggests that MIS can function as an effective adjuvant to current ovarian cancer chemotherapeutic regimens because of its ability to attack this elusive subpopulation of cancer cells. MIS also inhibits MOVCAR 8 and OVCAR 8 cells (25, 35), indicating that response to MIS is not only dependent on the presence of an SP.

Accumulating evidence suggests that somatic stem cells residing in local niche microenvironments may ultimately undergo mutagenic transformation into cancer stem cells (Calabrese et al., 2007) and that alternatively, aberrant regulatory signals from the niche microenvironment might also lead to tumorgenesis (Clarke and Fuller, 2006). The inventors herein demonstrate the presence of somatic stem cells in the adult mouse ovary and characterize their niche microenvironment. Using several lines of evidence and experimental approaches, the inventors demonstrate that coelomic LRCs residing in a perivascular niche microenvironment exist in the adult mouse ovary, are functionally responsive to the estrus cycle in vivo, and possess many of the functional properties ascribed to somatic stem cells from other tissues, as well as ovarian cancer stem cells (Szotek et al., 2006).

The inventors demonstrate, using both BrdU and Rosa26-rtTA; tetO-H2B-GFP pulse-chase experiments in combination with parabiosis and bone marrow transplant experiments, intrinsically derived coelomic LRCs located in a perivascular niche microenvironment (FIG. 11), characterize their surface marker phenotype (FIG. 12), and demonstrate that postovulatory coelomic reepithelialization is a stem cell-mediated process (FIG. 13 and FIG. 18—a model of coelomic epithelial repair). Surface marker characterization performed by the inventors demonstrated that the coelomic LRCs have an epithelial lineage in vivo and in vitro (cytokeratin-8$^+$, β-Catenin$^+$, and E-Cadherin$^+$), they are also vimentin$^+$ demonstrating a dual epithelial/mesenchymal potential ascribed to the embryonic and adult coelomic epithelium (Auersperg et al., 1999; Orvis and Behringer, 2007).

Herein, the inventors demonstrate that the ovarian surface epithelium contains a subset of cells that are able to form characteristic colonies in a mesenchymal stem cell CFU assay and that LRCs isolated by this method proliferate in a manner consistent with stem cell asymmetric division (FIG. 14 & FIG. 20). Finally, the inventors demonstrate that somatic LRCs from the normal ovarian coelomic epithelium enrich for the ovarian cancer stem cell-ascribed functional property of verapamil-sensitive Hoechst 33342 exclusion (SP). However, unlike ovarian cancer cells, which express the surface marker EpCam (Drapkin et al., 2004; Heinzelmann-Schwarz et al., 2004; Kim et al., 2003; Szotek et al., 2006), coelomic LRCs are negative for EpCam (FIG. 18). Parabiosis experiments performed by the inventors also demonstrates that the coelomic epithelial LRCs are not derived from the circulation/bone marrow but are intrinsic to the ovary. Collectively, the inventors have discovered and identified somatic stem cell population within the mouse ovarian coelomic epithelium that, like cancer stem cells, has the characteristics of slow-cycling (label retention) and multi-drug resistance (Hoechst 33342 dye exclusion/SP).

Figure 11D:
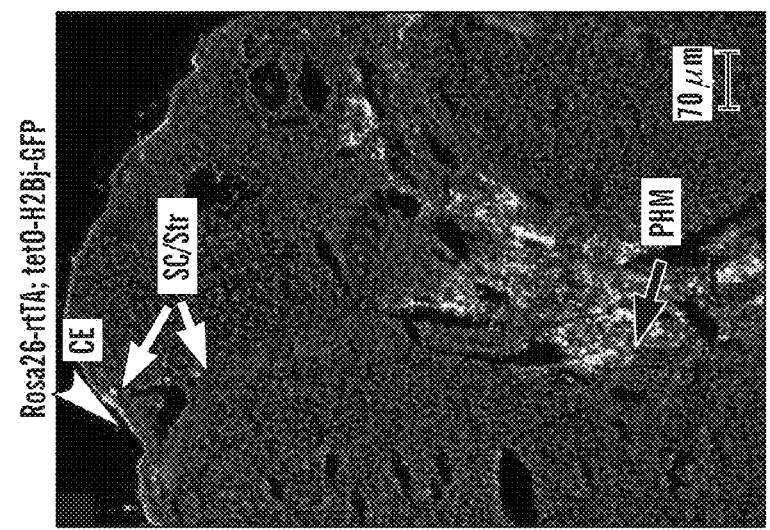
Figure 11B:
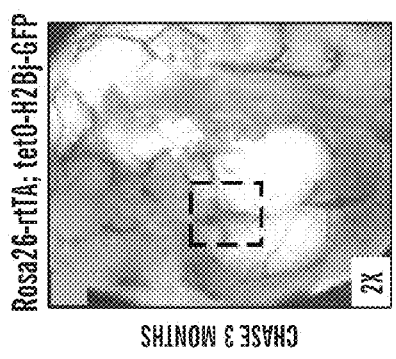
Figure 11C:
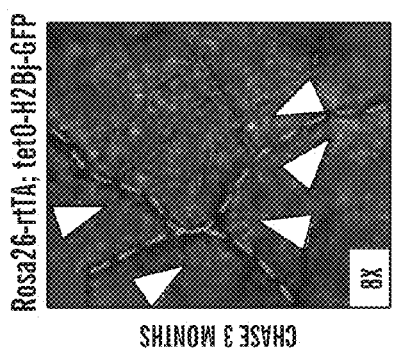
Figure 11E:
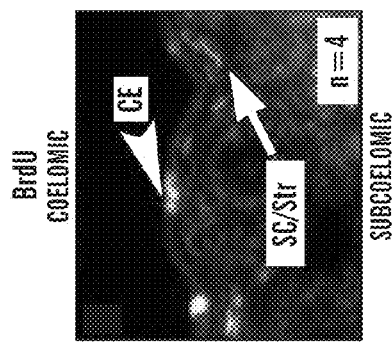
Figure 11G:
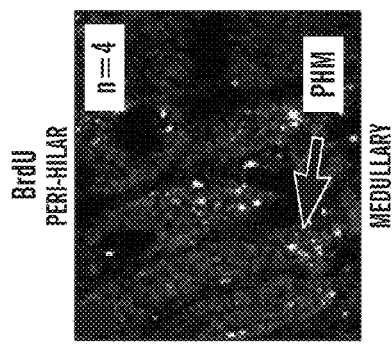
Figure 11F:
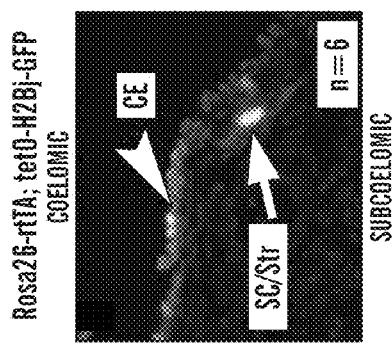
Figure 11H:
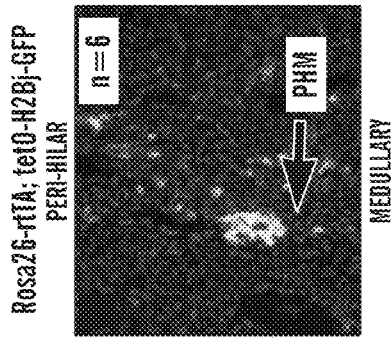
Figure 11I:
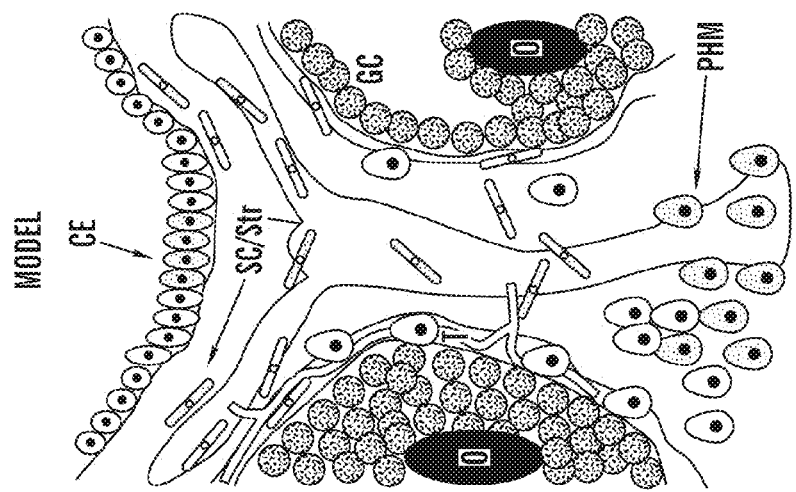

In addition to the characterization of the coelomic epithelial somatic stem cell, its niche microenvironment, and its potential relationship to ovarian cancer progression, the inventors demonstrate at least two other somatic LRCs exist within the ovarian stroma (subcoelomic/stromal LRCs and perihilar medullary LRCs; FIGS. 11C & 11D) and reside in perivascular niche microenvironments (data not shown).

Figure 18D:
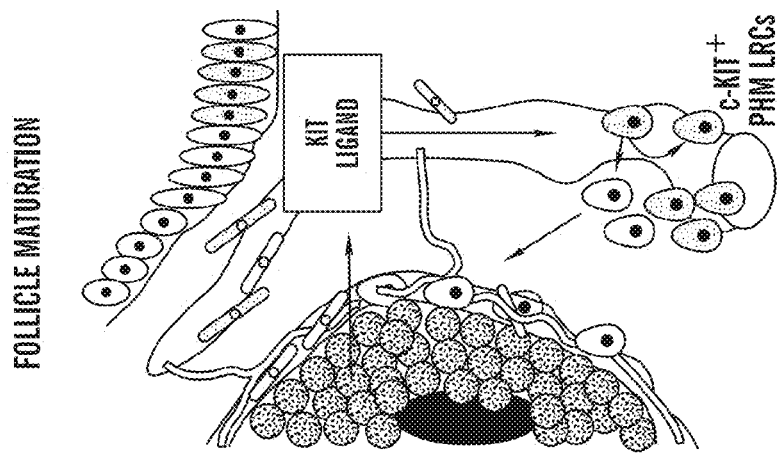
Figure 18C:
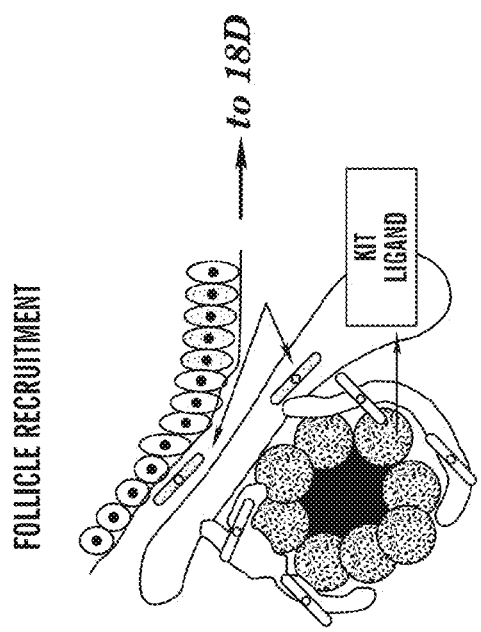

The inventors demonstrate, based on phenotypic lineage analysis of subcoelomic/stromal (cKIT$^-$/αSMA$^\pm$/PDGFRb$^+$/NG2$^\pm$/CD44$^+$/CD105$^+$/CD45$^-$/CD31$^-$) and perihilar medullary (cKIT$^+$/SF-1$^+$/GATA-4$^+$/CD44$^+$/CD105$^+$/CD45$^-$/CD31$^-$/αSMA$^-$) LRCs that these two non-coelomic LRC populations are involved in folliculogenesis as described in FIGS. 18C & 18D. Furthermore, using parabiosis experiments the inventors demonstrate that subcoelomic/stromal LRCs are circulation/bone marrow derived cells that appear to incorporate into the early developing follicular capillary network, while perihilar medullary LRCs are intrinsically derived and appear to incorporate into the maturing follicle as developing theca cells (FIG. 12).

The notion that cancer is derived from tissue stem cells is over one-hundred years old, but only recently has this hypothesis been validated (Reya et al., 2001; Sell, 2004) and insight provided into the mechanisms by which mutations may be accumulated, passed on to differentiating daughter cells, and ultimately lead to tumor progression. Herein, the inventors, using mouse models of label retaining cells, demonstrate that there is a sub-population of ovarian coelomic epithelial cells with somatic and cancer stem cell-like characteristics, including the ovarian cancer property of Hoechst dye efflux (SP). Since many of the same functional properties that define somatic stem cells also define the properties of cancer cells, the inventors have discovered a method to compare somatic ovarian stem cells with cancer ovarian stem cells to elucidate factors that cause a change from the normal somatic ovarian stem cells to ovarian cancer stem cell phenotype. In addition to demonstrating the existence coelomic LRCs, the inventors have also demonstrated a methods to isolate the somatic ovarian stem cells and ovarian cancer stem cells in vitro using a CFU assay, which can be used as a method to identify agents which inhibit the proliferation of the ovarian cancer stem cells as compared to the somatic ovarian stem cells.

Furthermore, having equated H2B and BrdU LRCs in pulse chase experiments and subsequently correlated enriched H2B-GFP in the SP population, the inventors have demonstrated that use of the side population (SP) in unmarked cells, such as those from primary human patient biological samples, as a marker to identify a biological sample enriched in an ovarian cancer stem cell population.

As demonstrated herein, the inventors have discovered methods to identify and enrich for somatic ovarian stem cells and ovarian cancer stem cells, which can be used for further study as well as use in assays to identify agents which inhibit the proliferation of ovarian cancer stem cells as compared to somatic ovarian cancer cells, as well as identify agents which prevent the transformation of somatic ovarian cancer cells to become ovarian cancer stem cells. Ultimately, the inventors have discovered the ovarian stem cell populations underlying ovarian cancer and a method for comparison of these two populations (ovarian cancer stem cells as compared to somatic ovarian cancer cells) that can be used to direct the development of therapies and treatments targeted at the chemotherapeutic elusive stem cell properties that define these populations.

REFERENCES

The references cited herein and throughout the application are incorporated herein by reference.

1. Al-Hajj, M., Wicha, M. S., Benito-Hernandez, A., Morrison, S. J. & Clarke, M. F. (2003) Proc. Natl. Acad. Sci. USA 100, 3983-3988.
2. Haraguchi, N., Utsunomiya, T., Inoue, H., Tanaka, F., Mimori, K., Barnard, G. F. & Mori, M. (2006) Stem Cells (Dayton, Ohio) 24, 506-513.
3. Kondo, T., Setoguchi, T. & Taga, T. (2004) Proc. Natl. Acad. Sci. USA 101, 781-786.
4. Wulf, G. G., Wang, R. Y., Kuehnle, I., Weidner, D., Marini, F., Brenner, M. K., Andreeff, M. & Goodell, M. A. (2001) Blood 98, 1166-1173.
5. Seigel, G. M., Campbell, L. M., Narayan, M. & Gonzalez-Fernandez, F. (2005) Mol. Vis. 11, 729-737.
6. Poste, G. & Greig, R. (1982) Invasion Metastasis 2, 137-176.
7. Poste, G., Tzeng, J., Doll, J., Greig, R., Rieman, D. & Zeidman, I. (1982) Proc. Natl. Acad. Sci. USA 79, 6574-6578.
8. Reya, T., Morrison, S. J., Clarke, M. F. & Weissman, I. L. (2001) Nature 414, 105-111.
9. Tu, S. M., Lin, S. H. & Logothetis, C. J. (2002) Lancet Oncol. 3, 508-513.
10. Li, L. & Xie, T. (2005) Annu. Rev. Cell Dev. Biol. 21, 605-631.
11. Bukovsky, A., Caudle, M. R., Svetlikova, M. & Upadhyaya, N. B. (2004) Reprod. Biol. Endocrinol. 2, 20.
12. Scully, R. E. (1970) Hum. Pathol. 1, 73-98.
13. Young, R. H. (2005) Mod. Pathol. 18 2, S3-S17.
14. Jemal, A., Murray, T., Ward, E., Samuels, A., Tiwari, R. C., Ghafoor, A., Feuer, E. J. & Thun, M. J. (2005) CA Cancer J. Clin. 55, 10-30.
15. Cannistra, S. A. (1993) N. Engl. J. Med. 329, 1550-1559.
16. Parker, S. L., Tong, T., Bolden, S. & Wingo, P. A. (1997) CA Cancer J. Clin. 47, 5-27.
17. Gottesman, M. M., Fojo, T. & Bates, S. E. (2002) Nat. Rev. Cancer 2, 48-58.
18. Goodell, M. A., Brose, K., Paradis, G., Conner, A. S. & Mulligan, R. C. (1996) J. Exp. Med. 183, 1797-1806.
19. Connolly, D. C., Bao, R., Nikitin, A. Y., Stephens, K. C., Poole, T. W., Hua, X., Harris, S. S., Vanderhyden, B. C. & Hamilton, T. C. (2003) Cancer Res. 63, 1389-1397.
20. Dinulescu, D. M., Ince, T. A., Quade, B. J., Shafer, S. A., Crowley, D. & Jacks, T. (2005) Nat. Med. 11, 63-70.
21. Hirschmann-Jax, C., Foster, A. E., Wulf, G. G., Nuchtern, J. G., Jax, T. W., Gobel, U., Goodell, M. A. & Brenner, M. K. (2004) Proc. Natl. Acad. Sci. USA 101, 14228-14233.
22. Doyle, L. A. & Ross, D. D. (2003) Oncogene 22, 7340-7358.
23. Gottesman, M. M. & Pastan, I. (1993) Annu. Rev. Biochem. 62, 385-427.
24. Sell, S. (2004) Crit. Rev. Oncol. Hematol. 51, 1-28.
25. Pieretti-Vanmarcke, R., Donahoe, P. K., Szotek, P., Manganaro, T., Lorenzen, M. K., Lorenzen, J., Connolly, D. C., Halpern, E. F. & MacLaughlin, D. T. (2006) Clin. Cancer Res. 12, 1593-1598.
26. Zhan, Y., Fujino, A., MacLaughlin, D., Manganaro, T., Szotek, P., Arango, N., Teixeira, J. & Donahoe, P. (2006) Development (Cambridge, U.K.) 133, 2359-2369.
27. Behbod, F. & Rosen, J. M. (2005) Carcinogenesis 26, 703-711.
28. Gale, R. P. & Butturini, A. (1992) Leukemia 6, Suppl. 1, 80-85.
29. Makino, S. (1956) Ann. N.Y. Acad. Sci. 63, 818-830.
30. Duan, Z., Brakora, K. A. & Seiden, M. V. (2004) Mol. Cancer. Ther. 3, 833-838.

31. Duan, Z., Lamendola, D. E., Yusuf, R. Z., Penson, R. T., Preffer, F. I. & Seiden, M. V. (2002) Anticancer Res. 22, 1933-1941.
32. Penson, R. T., Oliva, E., Skates, S. J., Glyptis, T., Fuller, A. F. Jr., Goodman, A. & Seiden, M. V. (2004) Gynecol. Oncol. 93, 98-106.
33. Seiden, M. V., Swenerton, K. D., Matulonis, U., Campos, S., Rose, P., Batist, G., Ette, E., Garg, V., Fuller, A., Harding, M. W. & Charpentier, D. (2002) Gynecol. Oncol. 86, 302-310.
34. Fuller, A. F. Jr., Krane, I. M., Budzik, G. P. & Donahoe, P. K. (1985) Gynecol. Oncol. 22, 135-148.
35. Ha, T. U., Segev, D. L., Barbie, D., Masiakos, P. T., Tran, T. T., Dombkowski, D., Glander, M., Clarke, T. R., Lorenzo, H. K., Donahoe, P. K. & Maheswaran, S. (2000) J. Biol. Chem. 275, 37101-37109.
36. Preffer, F. I., Dombkowski, D., Sykes, M., Scadden, D. & Yang, Y. G. (2002) Stem Cells (Dayton, Ohio) 20, 417-427.
37. Schilder, R. J., Hall, L., Monks, A., Handel, L. M., Formace, A. J. Jr., Ozols, R. F., Fojo, A. T. & Hamilton, T. C. (1990) Int. J. Cancer 45, 416-422.
38. Denizot, F. & Lang, R. (1986) J. Immunol. Methods 89, 271-277.
39. Lorenzo, H. K., Teixeira, J., Pahlavan, N., Laurich, V. M., Donahoe, P. K. & MacLaughlin, D. T. (2002) J. Chromatogr. B Biomed. Sci. Appl. 766, 89-98.
40. Hudson, P. L., Dougas, I., Donahoe, P. K., Cate, R. L., Epstein, J., Pepinsky, R. B. & MacLaughlin, D. T. (1990) J. Clin. Endocrinol. Metab. 70, 16-22.
41. Donahoe, P. K., Ito, Y., Marfatia, S. & Hendren, W. H. (1976) Biol. Reprod. 15, 329-334.
42. Donahoe, P. K., Ito, Y. & Hendren, W. H. (1977) J. Surg. Res. 23, 141-148.
Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988.
Albert, M. R., Foster, R. A., and Vogel, J. C. (2001). Murine epidermal label-retaining cells isolated by flow cytometry do not express the stem cell markers CD34, Sca-1, or Flk-1. J Invest Dermatol 117, 943-948.
Alvarez-Buylla, A., and Lim, D. A. (2004). For the long run: maintaining germinal niches in the adult brain. Neuron 41, 683-686.
Arango, N. A., Szotek, P. P., Manganaro, T. F., Oliva, E., Donahoe, P. K., and Teixeira, J. (2005). Conditional deletion of beta-catenin in the mesenchyme of the developing mouse uterus results in a switch to adipogenesis in the myometrium. Dev Biol 288, 276-283.
Auersperg, N., Pan, J., Grove, B. D., Peterson, T., Fisher, J., Maines-Bandiera, S., Somasiri, A., and Roskelley, C. D. (1999). E-cadherin induces mesenchymal-to-epithelial transition in human ovarian surface epithelium. Proc Natl Acad Sci USA 96, 6249-6254.
Beard, C., Hochedlinger, K., Plath, K., Wutz, A., and Jaenisch, R. (2006). Efficient method to generate single-copy transgenic mice by site-specific integration in embryonic stem cells. Genesis 44, 23-28.
Behbod, F., and Rosen, J. M. (2005). Will cancer stem cells provide new therapeutic targets? Carcinogenesis 26, 703-711.
Berns, A. (2005). Stem cells for lung cancer? Cell 121, 811-813.
Bhatt, R. I., Brown, M. D., Hart, C. A., Gilmore, P., Ramani, V. A., George, N. J., and Clarke, N. W. (2003). Novel method for the isolation and characterisation of the putative prostatic stem cell. Cytometry A 54, 89-99.
Bjersing, L., and Cajander, S. (1974). Ovulation and the mechanism of follicle rupture. V. Ultrastructure of tunica albuginea and theca externa of rabbit graafian follicles prior to induced ovulation. Cell Tissue Res 153, 15-30.
Bjersing, L., and Cajander, S. (1975). Ovulation and the role of the ovarian surface epithelium. Experientia 31, 605-608.
Blanpain, C., Lowry, W. E., Geoghegan, A., Polak, L., and Fuchs, E. (2004). Self-renewal, multipotency, and the existence of two cell populations within an epithelial stem cell niche. Cell 118, 635-648.
Braun, K. M., and Watt, F. M. (2004). Epidermal label-retaining cells: background and recent applications. J Investig Dermatol Symp Proc 9, 196-201.
Brennand, K., Huangfu, D., and Melton, D. (2007). All beta Cells Contribute Equally to Islet Growth and Maintenance. PLoS Biol 5, e163.
Bukovsky, A., Caudle, M. R., Svetlikova, M., and Upadhyaya, N. B. (2004). Origin of germ cells and formation of new primary follicles in adult human ovaries. Reprod Biol Endocrinol 2, 20.
Calabrese, C., Poppleton, H., Kocak, M., Hogg, T. L., Fuller, C., Hamner, B., Oh, E. Y., Gaber, M. W., Finklestein, D., Allen, M., et al. (2007). A perivascular niche for brain tumor stem cells. Cancer cell 11, 69-82.
Cheng, W., Liu, J., Yoshida, H., Rosen, D., and Naora, H. (2005). Lineage infidelity of epithelial ovarian cancers is controlled by HOX genes that specify regional identity in the reproductive tract. Nat Med 11, 531-537.
Clarke, M. F., and Fuller, M. (2006). Stem cells and cancer: two faces of eve. Cell 124, 1111-1115.
Clow, O. L., Hurst, P. R., and Fleming, J. S. (2002). Changes in the mouse ovarian surface epithelium with age and ovulation number. Mol Cell Endocrinol 191, 105-111.
Drapkin, R., Crum, C. P., and Hecht, J. L. (2004). Expression of candidate tumor markers in ovarian carcinoma and benign ovary: evidence for a link between epithelial phenotype and neoplasia. Human pathology 35, 1014-1021.
Eggan, K., Jurga, S., Gosden, R., Min, I. M., and Wagers, A. J. (2006). Ovulated oocytes in adult mice derive from non-circulating germ cells. Nature 441, 1109-1114.
Fuchs, E., Tumbar, T., and Guasch, G. (2004). Socializing with the neighbors: stem cells and their niche. Cell 116, 769-778.
Goodell, M. A., Brose, K., Paradis, G., Conner, A. S., and Mulligan, R. C. (1996). Isolation and functional properties of murine hematopoietic stem cells that are replicating in vivo. J Exp Med 183, 1797-1806.
Haraguchi, N., Utsunomiya, T., Inoue, H., Tanaka, F., Mimori, K., Barnard, G. F., and Mori, M. (2005). Characterization of a Side Population of Cancer Cells from Human Gastrointestinal System. Stem Cells, 2005-0282.
Heinzelmann-Schwarz, V. A., Gardiner-Garden, M., Henshall, S. M., Scurry, J., Scolyer, R. A., Davies, M. J., Heinzelmann, M., Kalish, L. H., Bali, A., Kench, J. G., et al. (2004). Overexpression of the cell adhesion molecules DDR1, Claudin 3, and Ep-CAM in metaplastic ovarian epithelium and ovarian cancer. Clin Cancer Res 10, 4427-4436.
Imitola, J., Comabella, M., Chandraker, A. K., Dangond, F., Sayegh, M. H., Snyder, E. Y., and Khoury, S. J. (2004). Neural stem/progenitor cells express costimulatory molecules that are differentially regulated by inflammatory and apoptotic stimuli. Am J Pathol 164, 1615-1625.
Johnson, J., Bagley, J., Skaznik-Wikiel, M., Lee, H. J., Adams, G. B., Niikura, Y., Tschudy, K. S., Tilly, J. C., Cortes, M. L., Forkert, R., et al. (2005). Oocyte generation in adult mammalian ovaries by putative germ cells in bone marrow and peripheral blood. Cell 122, 303-315.

Jonker, J. W., Freeman, J., Bolscher, E., Musters, S., Alvi, A. J., Titley, I., Schinkel, A. H., and Dale, T. C. (2005). Contribution of the ABC transporters Bcrp1 and Mdr1a/1b to the side population phenotype in mammary gland and bone marrow of mice. Stem Cells 23, 1059-1065.

Kenney, N. J., Smith, G. H., Lawrence, E., Barrett, J. C., and Salomon, D. S. (2001). Identification of Stem Cell Units in the Terminal End Bud and Duct of the Mouse Mammary Gland. J Biomed Biotechnol 1, 133-143.

Kim, J. H., Herlyn, D., Wong, K. K., Park, D. C., Schorge, J. O., Lu, K. H., Skates, S. J., Cramer, D. W., Berkowitz, R. S., and Mok, S. C. (2003). Identification of epithelial cell adhesion molecule autoantibody in patients with ovarian cancer. Clin Cancer Res 9, 4782-4791.

Kondo, M., Wagers, A. J., Manz, M. G., Prohaska, S. S., Scherer, D. C., Beilhack, G. F., Shizuru, J. A., and Weissman, I. L. (2003). Biology of hematopoietic stem cells and progenitors: implications for clinical application. Annu Rev Immunol 21, 759-806.

Leedham, S. J., Brittan, M., McDonald, S. A., and Wright, N. A. (2005). Intestinal stem cells. Cell Mol Med 9, 11-24.

Li, L., and Xie, T. (2005). Stem Cell Niche: Structure and Function. Annu Rev Cell Dev Biol.

Liu, X., Driskell, R. R., and Engelhardt, J. F. (2004). Airway glandular development and stem cells. Curr Top Dev Biol 64, 33-56.

Lowry, W. E., Blanpain, C., Nowak, J. A., Guasch, G., Lewis, L., and Fuchs, E. (2005). Defining the impact of beta-catenin/Tcf transactivation on epithelial stem cells. Genes Dev 19, 1596-1611.

Mills, J. C., and Gordon, J. I. (2001). The intestinal stem cell niche: there grows the neighborhood. Proc Natl Acad Sci USA 98, 12334-12336.

Morris, R. J., Fischer, S. M., and Slaga, T. J. (1986). Evidence that a slowly cycling subpopulation of adult murine epidermal cells retains carcinogen. Cancer Res 46, 3061-3066.

Morris, R. J., and Potten, C. S. (1994). Slowly cycling (label-retaining) epidermal cells behave like clonogenic stem cells in vitro. Cell Prolif 27, 279-289.

Morris, R. J., and Potten, C. S. (1999). Highly persistent label-retaining cells in the hair follicles of mice and their fate following induction of anagen. J Invest Dermatol 112, 470-475.

Morrison, S. J., Uchida, N., and Weissman, I. L. (1995). The biology of hematopoietic stem cells. Annu Rev Cell Dev Biol 11, 35-71.

Morrison, S. J., and Weissman, I. L. (1994). The long-term repopulating subset of hematopoietic stem cells is deterministic and isolatable by phenotype. Immunity 1, 661-673.

Murdoch, W. J., Townsend, R. S., and McDonnel, A. C. (2001). Ovulation-induced DNA damage in ovarian surface epithelial cells of ewes: prospective regulatory mechanisms of repair/survival and apoptosis. Biol Reprod 65, 1417-1424.

Oliver, J. A., Maarouf, O., Cheema, F. H., Martens, T. P., and Al-Awqati, Q. (2004). The renal papilla is a niche for adult kidney stem cells. J Clin Invest 114, 795-804.

Orlic, D., Fischer, R., Nishikawa, S., Nienhuis, A. W., and Bodine, D. M. (1993). Purification and characterization of heterogeneous pluripotent hematopoietic stem cell populations expressing high levels of c-kit receptor. Blood 82, 762-770.

Orvis, G. D., and Behringer, R. R. (2007). Cellular mechanisms of Mullerian duct formation in the mouse. Dev Biol 306, 493-504.

Patrawala, L., Calhoun, T., Schneider-Broussard, R., Zhou, J., Claypool, K., and Tang, D. G. (2005). Side Population Is Enriched in Tumorigenic, Stem-Like Cancer Cells, whereas ABCG2+ and ABCG2− Cancer Cells Are Similarly Tumorigenic. Cancer Res 65, 6207-6219.

Preffer, F. I., Dombkowski, D., Sykes, M., Scadden, D., and Yang, Y. G. (2002). Lineage-negative side-population (SP) cells with restricted hematopoietic capacity circulate in normal human adult blood: immunophenotypic and functional characterization. Stem Cells 20, 417-427.

Reya, T., Morrison, S. J., Clarke, M. F., and Weissman, I. L. (2001). Stem cells, cancer, and cancer stem cells. Nature 414, 105-111.

Sell, S. (2004). Stem cell origin of cancer and differentiation therapy. Crit Rev Oncol Hematol 51, 1-28.

Smalley, M. J., and Clarke, R. B. (2005). The mammary gland "side population": a putative stem/progenitor cell marker? J Mammary Gland Biol Neoplasia 10, 37-47.

Smalley, M. J., Titley, I., and Ashworth, A. (2005). An improved definition of mouse mammary epithelial side population cells. Cytotherapy 7, 497-508.

Spradling, A., Drummond-Barbosa, D., and Kai, T. (2001). Stem cells find their niche. Nature 414, 98-104.

Szotek, P. P., Chang, H. L., Zhang, L., Preffer, F., Dombkowski, D., Donahoe, P. K., and Teixeira, J. (2007). Adult Mouse Myometrial Label-Retaining Cells Divide in Response to Gonadotropin Stimulation. Stem Cells.

Szotek, P. P., Pieretti-Vanmarcke, R., Masiakos, P. T., Dinulescu, D. M., Connolly, D., Foster, R., Dombkowski, D., Preffer, F., Maclaughlin, D. T., and Donahoe, P. K. (2006). Ovarian cancer side population defines cells with stem cell-like characteristics and Mullerian Inhibiting Substance responsiveness. Proc Natl Acad Sci USA 103, 11154-11159.

Tan, O. L., and Fleming, J. S. (2004). Proliferating cell nuclear antigen immunoreactivity in the ovarian surface epithelium of mice of varying ages and total lifetime ovulation number following ovulation. Biol Reprod 71, 1501-1507.

Tsujimura, A., Koikawa, Y., Salm, S., Takao, T., Coetzee, S., Moscatelli, D., Shapiro, E., Lepor, H., Sun, T. T., and Wilson, E. L. (2002). Proximal location of mouse prostate epithelial stem cells: a model of prostatic homeostasis. J Cell Biol 157, 1257-1265.

Tumbar, T., Guasch, G., Greco, V., Blanpain, C., Lowry, W. E., Rendl, M., and Fuchs, E. (2004). Defining the epithelial stem cell niche in skin. Science 303, 359-363.

Vidrich, A., Buzan, J. M., and Cohn, S. M. (2003). Intestinal stem cells and mucosal gut development. Curr Opin Gastroenterol 19, 583-590.

Wagers, A. J., Sherwood, R. I., Christensen, J. L., and Weissman, I. L. (2002). Little evidence for developmental plasticity of adult hematopoietic stem cells. Science 297, 2256-2259.

Watt, F. M., and Hogan, B. L. (2000). Out of Eden: stem cells and their niches. Science 287, 1427-1430.

Welm, B., Behbod, F., Goodell, M. A., and Rosen, J. M. (2003). Isolation and characterization of functional mammary gland stem cells. Cell Prolif 36 Suppl 1, 17-32.

Welm, B. E., Tepera, S. B., Venezia, T., Graubert, T. A., Rosen, J. M., and Goodell, M. A. (2002). Sca-1 (pos) cells in the mouse mammary gland represent an enriched progenitor cell population. Dev Biol 245, 42-56.

Williams, E. D., Lowes, A. P., Williams, D., and Williams, G. T. (1992). A stem cell niche theory of intestinal crypt maintenance based on a study of somatic mutation in colonic mucosa. Am J Pathol 141, 773-776.

Wong, M. H. (2004). Regulation of intestinal stem cells. J Investig Dermatol Symp Proc 9, 224-228.

Wright, D. E., Wagers, A. J., Gulati, A. P., Johnson, F. L., and Weissman, I. L. (2001). Physiological migration of hematopoietic stem and progenitor cells. Science 294, 1933-1936.

Wu, W. Y., and Morris, R. J. (2005). In vivo labeling and analysis of epidermal stem cells. Methods Mol Biol 289, 73-78.

Wulf, G. G., Wang, R. Y., Kuehnle, I., Weidner, D., Marini, F., Brenner, M. K., Andreeff, M., and Goodell, M. A. (2001). A leukemic stem cell with intrinsic drug efflux capacity in acute myeloid leukemia. Blood 98, 1166-1173.

Zhan, Y., Fujino, A., MacLaughlin, D. T., Manganaro, T. F., Szotek, P. P., Arango, N. A., Teixeira, J., and Donahoe, P. K. (2006). Mullerian inhibiting substance regulates its receptor/SMAD signaling and causes mesenchymal transition of the coelomic epithelial cells early in Mullerian duct regression. Development 133, 2359-2369.

SEQUENCES

```
SEQ ID NO: 15: nucleic acid sequence of human MIS mRNA
(Accession ID; NM 000479.3 GeneID:157266297)
    1 gcatgttgac acatcaggcc cagctctatc actggggagg gagataggct gccagggaca 61 gaaagggctc tttgagaagg ccactctgcc tggagtgggg gcgccgggca ctgtccccca 121 aggtcgcggc agaggagata ggggtctgtc ctgcacaaac accccacctt ccactcggct 181 cacttaaggc aggcagccca gccoctggca gcacccacga tgcgggacct gcctctcacc 241 agcctggccc tagtgctgtc tgccctgggg gctctgctgg ggactgaggc cctcagagca 301 gaggagccag ctgtgggcac cagtggcctc atcttccgag aagacttgga ctggcctcca 361 ggcagcccac aagagcctct gtgcctggtg gcactgggcg gggacagcaa tggcagcagc 421 tccccctgc gggtggtggg ggctctaagc gcctatgagc aggccttcct gggggccgtg 481 cagagggccc gctgggccc ccgagacctg gccaccttcg gggtctgcaa caccggtgac 541 aggcaggctg ccttgcoctc tctacggcgg ctgggggcct ggctgcggga ccctgggggg 601 cagcgcctgg tggtcctaca cctggaggaa gtgacctggg agccaacacc ctcgctgagg 661 ttccaggagc ccccgcctgg aggagctggc ccccagagc tggcgctgct ggtgctgtac 721 cctgggcctg gccctgaggt cactgtgacg agggctgggc tgccgggtgc ccagagcctc 781 tgcccctccc gagacacccg ctacctggtg ttagcggtgg accgccctgc gggggcctgg 841 cgcggctccg ggctggcctt gaccctgcag ccccgcggag aggactcccg gctgagtacc 901 gcccggctgc aggcactgct gttcggcgac gaccaccgct gcttcacacg gatgacoccg 961 gccctgctcc tgctgccgcg gtccgagccc gcgccgctgc ctgcgcacgg ccagctggac 1021 accgtgccct tcccgccgcc caggccatcc gcggaactcg aggagtcgcc acccagcgca 1081 gaccccttcc tggagacgct cacgcgcctg gtgcgggcgc tgcgggtccc cccggcccgg 1141 gcctccgcgc cgcgcctggc cctggatccg gacgcgctgg ccggcttccc gcagggccta 1201 gtcaacctgt cggacccccgc ggcgctggag cgcctactcg acggcgagga gccgctgctg 1261 ctgctgctga ggcccactgc ggccaccacc ggggatcctg cgcccctgca cgacoccacg 1321 tcggcgccgt gggccacggc cctggcgcgc cgcgtggctg ctgaactgca agcggcggct 1381 gccgagctgc gaagcctccc gggtctgcct ccggccacag ccccgctgct ggcgcgcctg 1441 ctcgcgctct gcccaggtgg ccccggcggc ctcggcgatc ccctgcgagc gctgctgctc 1501 ctgaaggcgc tgcagggcct gcgcgtggag tggcgcgggc gggatccgcg cgggccgggt 1561 cgggcacagc gcagcgcggg ggccaccgcc gccgacgggc cgtgcgcgct gcgcgagctc 1621 agcgtagacc tccgcgccga gcgctccgta ctcatccccg agacctacca ggccaacaat 1681 tgccagggcg tgtgcggctg gcctcagtcc gaccgcaacc cgcgctacgg caaccacgtg 1741 gtgctgctgc tgaagatgca ggcccgtggg gccgccctgg cgcgccacc ctgctgcgtg 1801 cccaccgcct acgcgggcaa gctgctcatc agcctgtcgg aggagcgcat cagcgcgcac
```

```
1861 cacgtgccca acatggtggc caccgagtgt ggctgccggt gacccctgcg ccgcgcggac 1921 tcctgccccg agggtccgga cgcgcccag ctcgcgcccc ttcccatatt tattcggacc 1981 ccaagcatcg ccccaataaa gaccagcaag caaccggcaa aaaaaaaaa aaaaaaaaa 2041 aaaaaaaaaa aaaaaaaaaa aaaaa
```

SEQ ID NO: 16: amino acid sequence of human MIS protein
MRDLPLTSLALVLSALGALLGTEALRAEEPAVGTSGLIFREDLD

WPPGSPQEPLCLVALGGDSNGSSSPLRVVGALSAYEQAFLGAVQRARWGPRDLATFGV

CNTGDRQAALPSLRRLGAWLRDPGGQRLVVLHLEEVTWEPTPSLRFQEPPPGGAGPPE

LALLVLYPGPGPEVTVTRAGLPGAQSLCPSRDTRYLVLAVDRPAGAWRGSGLALTLQP

RGEDSRLSTARLQALLFGDDHRCFTRMTPALLLLPRSEPAPLPAHGQLDTVPFPPPRP

SAELEESPPSADPFLETLTRLVRALRVPPARASAPRLALDPDALAGFPQGLVNLSDPA

ALERLLDGEEPLLLLLRPTAATTGDPAPLHDPTSAPWATALARRVAAELQAAAAELRS

LPGLPPATAPLLARLLALCPGGPGGLGDPLRALLLLKALQGLRVEWRGRDPRGPGRAQ

RSAGATAADGPCALRELSVDLRAERSVLIPETYQANNCQGVCGWPQSDRNPRYGNHVV

LLLKMQARGAALARPPCCVPTAYAGKLLISLSEERISAHHVPNMVATECGCR

SEQ ID NO: 17: nucleic acid sequence of human MIS Receptor II (MISRII)
```
    1 atctgaagaa agatttggcc aggggcagct gtgctggctt atgctcttct ccttctgctg 61 ctgccatcct ccagcaagat gctagggtct ttggggcttt ggcattact tcccacagct 121 gtggaagcac cccaaacag gcgaacctgt gtgttctttg aggcccctgg agtgcgggga 181 agcacaaaga cactgggaga gctgctagat acaggcacag agctccccag agctatccgc 241 tgcctctaca gccgctgctg ctttgggatc tggaacctga cccaagaccg gcacaggtg 301 gaaatgcaag gatgccgaga cagtgatgag ccaggctgtg agtccctcca ctgtgaccca 361 agtccccgag cccaccccag ccctggctcc actctcttca cctgctcctg tggcactgac 421 ttctgcaatg ccaattacag ccatctgcct cctccaggga gccctgggac tcctggctcc 481 cagggtcccc aggctgcccc aggtgagtcc atctggatgg cactggtgct gctggggctg 541 ttcctcctcc tcctgctgct gctgggcagc atcatcttgg ccctgctaca gcgaaagaac 601 tacagagtgc gaggtgagcc agtgccagag ccaaggccag actcaggcag ggactggagt 661 gtggagctgc aggagctgcc tgagctgtgt ttctcccagg taatccggga aggaggtcat 721 gcagtggttt gggccgggca gctgcaagga aaactggttg ccatcaaggc cttcccaccg 781 aggtctgtgg ctcagttcca agctgagaga gcattgtacg aacttccagg cctacagcac 841 gaccacattg tccgatttat cactgccagc cgggggggtc ctggccgcct gctctctggg 901 cccctgctgg tactggaact gcatcccaag ggctccctgt gccactactt gacccagtac 961 accagtgact ggggaagttc cctgcggatg gcactgtccc tggcccaggg cctggcattt 1021 ctccatgagg agcgctggca gaatggccaa tataaaccag gtattgccca ccgagatctg 1081 agcagccaga atgtgctcat tcgggaagat ggatcgtgtg ccattggaga cctgggcctt 1141 gccttggtgc tccctggcct cactcagccc cctgcctgga cccctactca accacaaggc 1201 ccagctgcca tcatggaagc tggcacccag aggtacatgg caccagagct cttggacaag 1261 actctggacc tacaggattg ggcatggcc ctccgacgag ctgatattta ctctttggct 1321 ctgctcctgt gggagatact gagccgctgc ccagatttga ggcctgacag cagtccacca 1381 cccttccaac tggcctatga ggcagaactg ggcaatacccc ctacctctga tgagctatgg 1441 gccttggcag tgcaggagag gaggcgtccc tacatcccat ccacctggcg ctgctttgcc 1501 acagaccctg atgggctgag ggagctccta gaagactgtt gggatgcaga cccagaagca
```

-continued

```
1561 cggctgacag ctgagtgtgt acagcagcgc ctggctgcct tggcccatcc tcaagagagc 1621 caccccttc cagagagctg tccacgtggc tgcccacctc tctgcccaga agactgtact 1681 tcaattcctg ccctaccat cctccctgt aggcctcagc ggagtgcctg ccacttcagc 1741 gttcagcaag gccttgttc caggaatcct cagcctgcct gtacccttc tcctgtgtaa 1801 atatgcagtt tatgtgtcat caatgtacat gccaacataa atatggcgat tgtat
```

SEQ ID NO: 18: amino acid sequence of human MIS Receptor II (MISRII)
MLGSLGLWALLPTAVEAPPNRRTCVFFEAPGVRGSTKTLGELLD

TGTELPRAIRCLYSRCCFGIWNLTQDRAQVEMQGCRDSDEPGCESLHCDPSPRAHPSP

GSTLFTCSCGTDFCNANYSHLPPPGSPGTPGSQGPQAAPGESIWMALVLLGLFLLLLL

LLGSIILALLQRKNYRVRGEPVPEPRPDSGRDWSVELQELPELCFSQVIREGGHAVVW

AGQLQGKLVAIKAFPPRSVAQFQAERALYELPGLQHDHIVRFITASRGGPGRLLSGPL

LVLELHPKGSLCHYLTQYTSDWGSSLRMALSLAQGLAFLHEERWQNGQYKPGIAHRDL

SSQNVLIREDGSCAIGDLGLALVLPGLTQPPAWTPTQPQGPAAIMEAGTQRYMAPELL

DKTLDLQDWGMALRRADIYSLALLLWEILSRCPDLRPDSSPPPFQLAYEAELGNTPTS

DELWALAVQERRRPYIPSTWRCFATDPDGLRELLEDCWDADPEARLTAECVQQRLAAL

AHPQESHPFPESCPRGCPPLCPEDCTSIPAPTILPCRPQRSACHFSVQQGPCSRNPQP

ACTLSPV

SEQ ID NO: 19: nucleic acid sequence for human BCRP1
```
   1 gtcagcgctg cctgagctcg tccctggat gtccgggtct ccccaggcgg ccacccgccg 61 gctcccatcg tgacctccag ccgcagcgcc tcccacgccg gccgccgcgc gaggggagcg 121 ctcgggcgcg ccgggtgtgg ttgggggaag gggttgtgcc gcgcgcgggc tgcgtgctgt 181 gcccactcaa aaggttccgg gcgcgcagga gggaagaggc agtgcccgcc actcccactg 241 agattgagag acgcggcaag gaggcagcct gtggaggaac tgggtaggat ttaggaacgc 301 accgtgcaca tgcttggtgg tcttgttaag tggaaactgc tgctttagag tttgtttgga 361 aggtccgggt gactcatccc aacatttaca tccttaattg ttaaagcgct gcctccgagc 421 gcacgcatcc tgagatcctg agcctttggt taagaccgag ctctattaag ctgaaaagat 481 aaaaactctc cagatgtctt ccagtaatgt cgaagttttt atcccagtgt cacaaggaaa 541 caccaatggc ttccccgcga cagcttccaa tgacctgaag gcatttactg aaggagctgt 601 gttaagtttt cataacatct gctatcgagt aaaactgaag agtggctttc taccttgtcg 661 aaaaccagtt gagaaagaaa tattatcgaa tatcaatggg atcatgaaac tggtctcaa 721 cgccatcctg ggacccacag gtggaggcaa atcttcgtta ttagatgtct tagctgcaag 781 gaaagatcca agtggattat ctggagatgt tctgataaat ggagcaccgc gacctgccaa 841 tttcaaatgt aattcaggtt acgtggtaca agatgatgtt gtgatgggca ctctgacggt 901 gagagaaaac ttacagttct cagcagctct tcggcttgca caactatga cgaatcatga 961 aaaaacgaa cggattaaca gggtcattca agagttaggt ctggataaag tggcagactc 1021 caaggttgga actcagttta tccgtggtgt gtctggagga gaaagaaaaa ggactagtat 1081 aggaatggag cttatcactg atccttccat cttgttcttg gatgagccta aactggcctt 1141 agactcaagc acagcaaatg ctgtcctttt gctcctgaaa aggatgtcta agcagggacg 1201 aacaatcatc ttctccattc atcagcctcg atattccatc ttcaagttgt ttgatagcct 1261 cacccttattg gcctcaggaa gacttatgtt ccacgggcct gctcaggagg ccttgggata 1321 ctttgaatca gctggttatc actgtgaggc ctataataac cctgcagact tcttcttgga
```

-continued

```
1381 catcattaat ggagattcca ctgctgtggc attaaacaga gaagaagact ttaaagccac 1441 agagatcata gagccttcca agcaggataa gccactcata gaaaaattag cggagattta 1501 tgtcaactcc tccttctaca aagagacaaa agctgaatta catcaacttt ccggggggtga 1561 gaagaagaag aagatcacag tcttcaagga gatcagctac accacctcct tctgtcatca 1621 actcagatgg gtttccaagc gttcattcaa aaacttgctg ggtaatcccc aggcctctat 1681 agctcagatc attgtcacag tcgtactggg actggttata ggtgccattt actttgggct 1741 aaaaaatgat tctactggaa tccagaacag agctggggtt ctcttcttcc tgacgaccaa 1801 ccagtgtttc agcagtgttt cagccgtgga actctttgtg gtagagaaga agctcttcat 1861 acatgaatac atcagcggat actacagagt gtcatcttat ttccttggaa aactgttatc 1921 tgatttatta cccatgagga tgttaccaag tattatattt acctgtatag tgtacttcat 1981 gttaggattg aagccaaagg cagatgcctt cttcgttatg atgtttaccc ttatgatggt 2041 ggcttattca gccagttcca tggcactggc catagcagca ggtcagagtg tggtttctgt 2101 agcaacactt ctcatgacca tctgttttgt gtttatgatg attttttcag gtctgttggt 2161 caatctcaca accattgcat cttggctgtc atggcttcag tacttcagca ttccacgata 2221 tggatttacg gctttgcagc ataatgaatt tttgggacaa aacttctgcc caggactcaa 2281 tgcaacagga aacaatcctt gtaactatgc aacatgtact ggcgaagaat atttggtaaa 2341 gcagggcatc gatctctcac cctggggctt gtggaagaat cacgtggcct tggcttgtat 2401 gattgttatt ttcctcacaa ttgcctacct gaaattgtta tttcttaaaa aatattctta 2461 aatttcccct taattcagta tgatttatcc tcacataaaa aagaagcact ttgattgaag 2521 tattcaatca agttttttg ttgttttctg ttcccttgcc atcacactgt tgcacagcag 2581 caattgtttt aaagagatac attttagaa atcacaacaa actgaattaa acatgaaaga 2641 acccaagaca tcatgtatcg catattagtt aatctcctca gacagtaacc atggggaaga 2701 aatctggtct aatttattaa tctaaaaaag gagaattgaa ttctggaaac tcctgacaag 2761 ttattactgt ctctggcatt tgtttcctca tctttaaaat gaataggtag gttagtagcc 2821 cttcagtctt aatactttat gatgctatgg tttgccatta tttaataaat gacaaatgta 2881 ttaatgctat actggaaatg taaaattgaa aatatgttgg aaaaaagatt ctgtcttata 2941 gggtaaaaaa agccaccgtg atagaaaaaa aatcttttg ataagcacat taaagttaat 3001 agaacttact gatattcctg tctagtggta taatatctca ggaatcttgg ctgagggttt 3061 ggaactgtgg gtagagtaga gggccaggag tccagtaata gaattcttgc accatttctg 3121 gaacattcta gctctgggag gtcacgtaac cttcttgggg tagttcagtg gtttagtggt 3181 ttataatcca ggtgtgcgtc agaatcatct gaggaacttt gctaaaatac aaaaatctgg 3241 cctaagtagc tccagatcta ccttcataaa ggaatctgac cactcctgga tttggtaatt 3301 tccaagttct gaaaattta cttaggattt ataactatt aacatctgtc cctacatagg 3361 ttttctttcc tacttatata ccttatgttc tcttcattct aaccttcatc agtaataggg 3421 aaatgtttta atttttatttt tttagttgaa gggtaatgta ccaaaaaata tagttcagtg 3481 aattaaaatg aacacacatg tgcaaccatc aattcaggtc aagaaataga agattgtagc 3541 acacaaaagc ctactcagcc attctcccag tcactacttc cttccttacc cctgggttat 3601 ttttgaaatg acacttgatg tatttccctc tgttgctgtt atgagaacat tgctacagcc 3661 aagtgttgtg tttctgtgtg cataggttga tacttaatta tctccccact ttttaataaa 3721 cttttaattt ggaaataatt ttagattgac agaaagttg caaagatagt gaggaaagtt 3781 cctgtctact ctttgctcag cttcccttaa tgttaacatt ttatatagca agatgcattt
```

-continued

```
3841 gtcaaagcta acaagttaac attggtacaa tcactgttaa ttaaactgca cacaatattc 3901 agatttcacc acttttccac taatattctt tcattgttct aggattcaat tcaggagacc 3961 acatttcatc tagccctctt ttttaaaagt aaatacttttt cagcacttac aggagttaac 4021 tgagctgggg catcatggtg tatagacgcc ctgacactgg tcatcttgga attcatttag 4081 tttgtcagtg ggtgccctga cattctgtca caacatcaat ttgggaacat ggcattatat 4141 ttttatcttt gaacttttt cttttggat gacatttgat taatgcgtca tcttggaaca 4201 cattatcttt tttcttggtt atgtgatcag gaagattaat cagttttttcc tgttcttggt 4261 ataattcctg cttttcacat acctgtccct tacagttctc tatatatacc cttcccttat 4321 tacacagaga gaaatatcta tctatacttt ttacacaaaa tatacttcaa aagaaacaaa 4381 acagccacaa ttattaactt tttaaataaa tgagaattta attatatcct aaaaaaaaaa 4441 aaaaa
```

SEQ ID NO: 20: Amino acid sequence for BCRP1 (Accession No: NP 004818)
MSSSNVEVFIPVSQGNTNGFPATASNDLKAFTEGAVLSFHNICY

RVKLKSGFLPCRKPVEKEILSNINGIMKPGLNAILGPTGGGKSSLLDVLAARKDPSGL

SGDVLINGAPRPANFKCNSGYVVQDDVVMGTLTVRENLQFSAALRLATTMTNHEKNER

INRVIQELGLDKVADSKVGTQFIRGVSGGERKRTSIGMELITDPSILFLDEPTTGLDS

STANAVLLLLKRMSKQGRTIIFSIHQPRYSIFKLFDSLTLLASGRLMFHGPAQEALGY

FESAGYHCEAYNNPADFFLDIINGDSTAVALNREEDFKATEIIEPSKQDKPLIEKLAE

IYVNSSFYKETKAELHQLSGGEKKKKITVFKEISYTTSFCHQLRWVSKRSFKNLLGNP

QASIAQIIVTVVLGLVIGAIYFGLKNDSTGIQNRAGVLFFLTTNQCFSSVSAVELFVV

EKKLFIHEYISGYYRVSSYFLGKLLSDLLPMRMLPSIIFTCIVYFMLGLKPKADAFFV

MMFTLMMVAYSASSMALAIAAGQSVVSVATLLMTICFVFMMIFSGLLVNLTTIASWLS

WLQYFSIPRYGFTALQHNEFLGQNFCPGLNATGNNPCNYATCTGEEYLVKQGIDLSPW

GLWKNHVALACMIVIFLTIAYLKLLFLKKYS

---

The invention claimed is:

1. A method for collecting a population of ovarian cancer stem cells, the method comprising
   (i) contacting a biopsy tissue sample comprising a population of ovarian cancer cells with an anti-EpCam, an anti-cytokeratin-8 and an anti-β-catenin antibody, antibody derivative or fragment thereof;
   (ii) separating the ovarian cancer cells that are positive for binding the combination of anti-EpCam, anti-cytokeratin-8, and anti-β-catenin antibodies, from the ovarian cancer cells that do not bind all three of the antibodies;
   (iii) collecting the ovarian cancer cells that are positive for the binding of the combination of anti-EpCam, anti-cytokeratin-8, and anti-β-catenin antibodies, wherein the isolated ovarian cancer cells comprises ovarian cancer stem cells.

2. The method of claim 1, further comprising measuring the expression of breast cancer-resistance protein 1 (BCRP1) and/or the ability of the ovarian cells to efflux a lipophilic dye, and collecting the population of ovarian cells which are positive for BCRP1 expression and/or the ability to efflux a lipophic dye.

3. The method of claim 1, wherein the biopsy tissue sample comprises ovarian cancer cells.

4. The method of claim 3, wherein the ovarian cancer cells are selected from the group comprising, vulvar epidermal carcinoma cells, cervical carcinoma cells, endometrial adenocarcinoma cells and ovarian adenocarcinoma cells.

5. The method of claim 1, wherein the biopsy tissue sample is obtained from a human subject.

6. The method of claim 1, wherein the biopsy tissue sample is obtained from a mammal.

7. The method of claim 1, wherein the ovarian cancer stem cell population has multi-drug resistance sensitivity.

8. The method of claim 7, wherein the ovarian cancer stem cell population is resistant to paclitaxel, cisplatin, doxorubicin.

9. The method of claim 7, wherein the ovarian cancer stem cell population is sensitive to a BCRP1 inhibitor.

10. The method of claim 8, wherein the BCRP1 inhibitor is verapamil.

11. The method of claim 7, wherein the ovarian cancer stem cell population is sensitive to recombinant mullerian inhibiting substance (MIS).

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatagccac aggccaaagt                                                20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggccacatg attcttccac                                                20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctggttttt gctggtttat gc                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttggggata cttgtgctgc cg                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgaactgaag cctctggaat gc                                              22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcgtaagcaa ctgcctgaac atc                                             23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aacctgagcc acaatgaacc g                                               21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctgaacaaa gatgctgctg tcac                                            24

```
<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagcactggt gttctgttgc ctac                                              24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccatctgagt gagcacctta tcc                                               23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttatacaatg gtcgatggag c                                                 21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcaggcgct cttgattgc                                                    19

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgactcagc tatacactta catcag                                            26

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caggtctttc agtgattctc c                                                 21

<210> SEQ ID NO 15
```

<211> LENGTH: 2065
<212> TYPE: DNA
<213> ORGANISM: Homo sapiens

<400> SEQUENCE: 15

```
gcatgttgac acatcaggcc cagctctatc actggggagg gagataggct gccagggaca        60
gaaagggctc tttgagaagg ccactctgcc tggagtgggg gcgccgggca ctgtccccca       120
aggtcgcggc agaggagata ggggtctgtc ctgcacaaac accccacctt ccactcggct       180
cacttaaggc aggcagccca gcccctggca gcacccacga tgcgggacct gcctctcacc       240
agcctggccc tagtgctgtc tgccctgggg gctctgctgg ggactgaggc cctcagagca       300
gaggagccag ctgtgggcac cagtggcctc atcttccgag aagacttgga ctggcctcca       360
ggcagcccac aagagcctct gtgcctggtg gcactgggcg gggacagcaa tggcagcagc       420
tcccccctgc gggtggtggg ggctctaagc gcctatgagc aggccttcct ggggccgtg       480
cagagggccc gctggggccc ccgagacctg gccaccttcg gggtctgcaa caccggtgac       540
aggcaggctg ccttgccctc tctacggcgg ctggggcct ggctgcggga ccctgggggg       600
cagcgcctgg tggtcctaca cctggaggaa gtgacctggg agccaacacc ctcgctgagg       660
ttccaggagc cccgcctgg aggagctggc ccccagagc tggcgctgct ggtgctgtac        720
cctgggcctg gccctgaggt cactgtgacg agggctgggc tgccgggtgc ccagagcctc       780
tgcccctccc gagacacccg ctacctggtg ttagcggtgg accgccctgc ggggggcctgg      840
cgcggctccg ggctggcctt gaccctgcag ccccgcggag aggactcccg gctgagtacc       900
gcccggctgc aggcactgct gttcggcgac gaccaccgct gcttcacacg gatgaccccg       960
gccctgctcc tgctgccgcg gtccgagccc gcgccgctgc ctgcgcacgg ccagctggac      1020
accgtgccct cccgccgcc caggccatcc gcggaactcg aggagtcgcc acccagcgca       1080
gaccccttcc tggagacgct cacgcgcctg gtgcgggcgc tgcgggtccc ccggcccgg       1140
gcctccgcgc cgcgcctggc cctggatccg gacgcgctgg ccggcttccc gcagggccta      1200
gtcaacctgt cggaccccgc ggcgctggag cgcctactcg acggcgagga gccgctgctg      1260
ctgctgctga ggcccactgc ggccaccacc ggggatcctg cgcccctgca cgaccccacg      1320
tcggcgccgt gggccacggc cctggcgcgc gcgtggctg ctgaactgca agcggcggct       1380
gccgagctgc gaagcctccc gggtctgcct ccggccacag ccccgctgct ggcgcgcctg      1440
ctcgcgctct gccaggtgg ccccggcggc ctcggcgatc ccctgcgagc gctgctgctc       1500
ctgaaggcgc tgcagggcct gcgcgtggag tggcgcgggc gggatccgcg cgggccgggt      1560
cgggcacagc gcagcgcggg ggccaccgcc gccgacgggc cgtgcgcgct gcgcgagctc      1620
agcgtagacc tccgcgccga gcgctccgta ctcatccccg agacctacca ggccaacaat      1680
tgccagggcg tgtgcggctg gcctcagtcc gaccgcaacc cgcgctacgg caaccacgtg      1740
gtgctgctgc tgaagatgca ggccgtgggg ccgccctgg gcgcccacc ctgctgcgtg        1800
cccaccgcct acgcgggcaa gctgctcatc agcctgtcgg aggagcgcat cagcgcgcac      1860
cacgtgccca acatggtggc caccgagtgt ggctgccggt gacccctgcg ccgcgcggac      1920
tcctgccccg agggtccgga cgcgcccag ctcgcgcccc ttcccatatt tattcggacc      1980
ccaagcatcg ccccaataaa gaccagcaag caaccggcaa aaaaaaaaaa aaaaaaaaa      2040
aaaaaaaaaa aaaaaaaaaa aaaaa                                           2065
```

<210> SEQ ID NO 16
<211> LENGTH: 560

<212> TYPE: PRT
<213> ORGANISM: Homo sapiens

<400> SEQUENCE: 16

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
130                 135                 140

Ser Leu Arg Phe Gln Glu Pro Pro Gly Gly Ala Gly Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Arg Pro
            340                 345                 350

Thr Ala Ala Thr Thr Gly Asp Pro Ala Pro Leu His Asp Pro Thr Ser
        355                 360                 365

Ala Pro Trp Ala Thr Ala Leu Ala Arg Arg Val Ala Ala Glu Leu Gln
    370                 375                 380

Ala Ala Ala Ala Glu Leu Arg Ser Leu Pro Gly Leu Pro Pro Ala Thr
385                 390                 395                 400

```
Ala Pro Leu Leu Ala Arg Leu Leu Ala Leu Cys Pro Gly Gly Pro Gly
            405                 410                 415
Gly Leu Gly Asp Pro Leu Arg Ala Leu Leu Leu Lys Ala Leu Gln
            420                 425                 430
Gly Leu Arg Val Glu Trp Arg Gly Arg Asp Pro Arg Gly Pro Gly Arg
            435                 440                 445
Ala Gln Arg Ser Ala Gly Ala Thr Ala Ala Asp Gly Pro Cys Ala Leu
450                 455                 460
Arg Glu Leu Ser Val Asp Leu Arg Ala Glu Arg Ser Val Leu Ile Pro
465                 470                 475                 480
Glu Thr Tyr Gln Ala Asn Asn Cys Gln Gly Val Cys Gly Trp Pro Gln
            485                 490                 495
Ser Asp Arg Asn Pro Arg Tyr Gly Asn His Val Val Leu Leu Leu Lys
            500                 505                 510
Met Gln Ala Arg Gly Ala Ala Leu Ala Arg Pro Pro Cys Cys Val Pro
            515                 520                 525
Thr Ala Tyr Ala Gly Lys Leu Leu Ile Ser Leu Ser Glu Glu Arg Ile
            530                 535                 540
Ser Ala His His Val Pro Asn Met Val Ala Thr Glu Cys Gly Cys Arg
545                 550                 555                 560

<210> SEQ ID NO 17
<211> LENGTH: 1855
<212> TYPE: DNA
<213> ORGANISM: Homo sapiens

<400> SEQUENCE: 17
atctgaagaa agatttggcc aggggcagct gtgctggctt atgctcttct ccttctgctg      60
ctgccatcct ccagcaagat gctagggtct ttggggcttt gggcattact tcccacagct     120
gtggaagcac ccccaaacag gcgaacctgt gtgttctttg aggcccctgg agtgcgggga     180
agcacaaaga cactgggaga gctgctagat acaggcacag agctccccag agctatccgc     240
tgcctctaca gccgctgctg ctttgggatc tggaacctga cccaagaccg ggcacaggtg     300
gaaatgcaag gatgccgaga cagtgatgag ccaggctgtg agtccctcca ctgtgaccca     360
agtccccgag cccaccccag ccctggctcc actctcttca cctgctcctg tggcactgac     420
ttctgcaatg ccaattacag ccatctgcct cctccaggga gccctgggac tcctggctcc     480
cagggtcccc aggctgcccc aggtgagtcc atctggatgg cactggtgct gctggggctg     540
ttcctcctcc tcctgctgct gctgggcagc atcatcttgg ccctgctaca gcgaaagaac     600
tacagagtgc gaggtgagcc agtgccagag ccaaggccag actcaggcag ggactggagt     660
gtggagctgc aggagctgcc tgagctgtgt ttctcccagg taatccggga aggaggtcat     720
gcagtggttt gggccgggca gctgcaagga aaactggttg ccatcaaggc cttcccaccg     780
aggtctgtgg ctcagttcca agctgagaga gcattgtacg aacttccagg cctacagcac     840
gaccacattg tccgatttat cactgccagc cggggggtc ctggccgcct gctctctggg     900
cccctgctgg tactggaact gcatcccaag ggctccctgt gccactactt gacccagtac     960
accagtgact ggggaagttc cctgcggatg gcactgtccc tggcccaggg cctggcattt    1020
ctccatgagg agcgctggca gaatggccaa tataaaccag gtattgccca ccgagatctg    1080
agcagccaga atgtgctcat tcgggaagat ggatcgtgtg ccattggaga cctgggcctt    1140
gccttggtgc tccctggcct cactcagccc cctgcctgga ccctactca accacaaggc    1200
```

```
ccagctgcca tcatggaagc tggcacccag aggtacatgg caccagagct cttggacaag   1260
actctggacc tacaggattg gggcatggcc ctccgacgag ctgatattta ctctttggct   1320
ctgctcctgt gggagatact gagccgctgc ccagatttga ggcctgacag cagtccacca   1380
cccttccaac tggcctatga ggcagaactg ggcaataccc ctacctctga tgagctatgg   1440
gccttggcag tgcaggagag gaggcgtccc tacatcccat ccacctggcg ctgctttgcc   1500
acagaccctg atgggctgag ggagctccta gaagactgtt gggatgcaga cccagaagca   1560
cggctgacag ctgagtgtgt acagcagcgc ctggctgcct tggcccatcc tcaagagagc   1620 caccccttc cagagagctg tccacgtggc tgcccacctc tctgcccaga agactgtact   1680
tcaattcctg cccctaccat cctcccctgt aggcctcagc ggagtgcctg ccacttcagc   1740
gttcagcaag gccttgttc caggaatcct cagcctgcct gtacccttc tcctgtgtaa   1800 atatgcagtt tatgtgtcat caatgtacat gccaacataa atatggcgat tgtat         1855
```

<210> SEQ ID NO 18
<211> LENGTH: 573
<212> TYPE: PRT
<213> ORGANISM: Homo sapiens

<400> SEQUENCE: 18

```
Met Leu Gly Ser Leu Gly Leu Trp Ala Leu Leu Pro Thr Ala Val Glu
 1               5                  10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
        50                  55                  60

Trp Asn Leu Thr Gln Asp Arg Ala Gln Val Glu Met Gln Gly Cys Arg
 65                  70                  75                  80

Asp Ser Asp Glu Pro Gly Cys Glu Ser Leu His Cys Asp Pro Ser Pro
                 85                  90                  95

Arg Ala His Pro Ser Pro Gly Ser Thr Leu Phe Thr Cys Ser Cys Gly
                100                 105                 110

Thr Asp Phe Cys Asn Ala Asn Tyr Ser His Leu Pro Pro Pro Gly Ser
            115                 120                 125

Pro Gly Thr Pro Gly Ser Gln Gly Pro Gln Ala Ala Pro Gly Glu Ser
        130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
                180                 185                 190

Trp Ser Val Glu Leu Gln Glu Leu Pro Glu Leu Cys Phe Ser Gln Val
            195                 200                 205

Ile Arg Glu Gly Gly His Ala Val Val Trp Ala Gly Gln Leu Gln Gly
        210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
```

```
           260                 265                 270
Ser Gly Pro Leu Leu Val Leu Glu Leu His Pro Lys Gly Ser Leu Cys
        275                 280                 285
His Tyr Leu Thr Gln Tyr Thr Ser Asp Trp Gly Ser Ser Leu Arg Met
    290                 295                 300
Ala Leu Ser Leu Ala Gln Gly Leu Ala Phe Leu His Glu Glu Arg Trp
305                 310                 315                 320
Gln Asn Gly Gln Tyr Lys Pro Gly Ile Ala His Arg Asp Leu Ser Ser
                325                 330                 335
Gln Asn Val Leu Ile Arg Glu Asp Gly Ser Cys Ala Ile Gly Asp Leu
            340                 345                 350
Gly Leu Ala Leu Val Leu Pro Gly Leu Thr Gln Pro Pro Ala Trp Thr
        355                 360                 365
Pro Thr Gln Pro Gln Gly Pro Ala Ala Ile Met Glu Ala Gly Thr Gln
    370                 375                 380
Arg Tyr Met Ala Pro Glu Leu Leu Asp Lys Thr Leu Asp Leu Gln Asp
385                 390                 395                 400
Trp Gly Met Ala Leu Arg Arg Ala Asp Ile Tyr Ser Leu Ala Leu Leu
                405                 410                 415
Leu Trp Glu Ile Leu Ser Arg Cys Pro Asp Leu Arg Pro Asp Ser Ser
            420                 425                 430
Pro Pro Pro Phe Gln Leu Ala Tyr Glu Ala Glu Leu Gly Asn Thr Pro
        435                 440                 445
Thr Ser Asp Glu Leu Trp Ala Leu Ala Val Gln Glu Arg Arg Arg Pro
    450                 455                 460
Tyr Ile Pro Ser Thr Trp Arg Cys Phe Ala Thr Asp Pro Asp Gly Leu
465                 470                 475                 480
Arg Glu Leu Leu Glu Asp Cys Trp Asp Ala Asp Pro Glu Ala Arg Leu
                485                 490                 495
Thr Ala Glu Cys Val Gln Gln Arg Leu Ala Ala Leu Ala His Pro Gln
            500                 505                 510
Glu Ser His Pro Phe Pro Glu Ser Cys Pro Arg Gly Cys Pro Pro Leu
        515                 520                 525
Cys Pro Glu Asp Cys Thr Ser Ile Pro Ala Pro Thr Ile Leu Pro Cys
    530                 535                 540
Arg Pro Gln Arg Ser Ala Cys His Phe Ser Val Gln Gln Gly Pro Cys
545                 550                 555                 560
Ser Arg Asn Pro Gln Pro Ala Cys Thr Leu Ser Pro Val
                565                 570

<210> SEQ ID NO 19
<211> LENGTH: 4445
<212> TYPE: DNA
<213> ORGANISM: Homo sapiens

<400> SEQUENCE: 19
gtcagcgctg cctgagctcg tccctggat gtccgggtct ccccaggcgg ccaccgccg      60 gctcccatcg tgacctccag ccgcagcgcc tcccacgccg ccgccgcgc gaggggagcg    120 ctcgggcgcg ccgggtgtgg ttgggggaag gggttgtgcc gcgcgcgggc tgcgtgctgt    180
gcccactcaa aaggttccgg gcgcgcagga gggaagaggc agtgcccgcc actcccactg    240
agattgagag acgcggcaag gaggcagcct gtggaggaac tgggtaggat ttaggaacgc    300
accgtgcaca tgcttggtgg tcttgttaag tggaaactgc tgcttttagag tttgtttgga    360
```

-continued

```
aggtccgggt gactcatccc aacatttaca tccttaattg ttaaagcgct gcctccgagc    420
gcacgcatcc tgagatcctg agcctttggt taagaccgag ctctattaag ctgaaaagat    480
aaaaactctc cagatgtctt ccagtaatgt cgaagttttt atcccagtgt cacaaggaaa    540
caccaatggc ttccccgcga cagcttccaa tgacctgaag gcatttactg aaggagctgt    600
gttaagtttt cataacatct gctatcgagt aaaactgaag agtggctttc taccttgtcg    660
aaaaccagtt gagaaagaaa tattatcgaa tatcaatggg atcatgaaac ctggtctcaa    720
cgccatcctg ggacccacag gtggaggcaa atcttcgtta ttagatgtct tagctgcaag    780
gaaagatcca agtggattat ctggagatgt tctgataaat ggagcaccgc gacctgccaa    840
tttcaaatgt aattcaggtt acgtggtaca agatgatgtt gtgatgggca ctctgacggt    900
gagagaaaac ttacagttct cagcagctct tcggcttgca acaactatga cgaatcatga    960
aaaaaacgaa cggattaaca gggtcattca agagttaggt ctggataaag tggcagactc   1020
caaggttgga actcagttta tccgtggtgt gtctggagga gaaagaaaaa ggactagtat   1080
aggaatggag cttatcactg atccttccat cttgttcttg gatgagccta caactggctt   1140
agactcaagc acagcaaatg ctgtcctttt gctcctgaaa aggatgtcta agcagggacg   1200
aacaatcatc ttctccattc atcagcctcg atattccatc ttcaagttgt ttgatagcct   1260
caccttattg gcctcaggaa gacttatgtt ccacgggcct gctcaggagg ccttgggata   1320
ctttgaatca gctggttatc actgtgaggc ctataataac cctgcagact tcttcttgga   1380
catcattaat ggagattcca ctgctgtggc attaaacaga gaagaagact taaagccac    1440 agagatcata gagccttcca agcaggataa gccactcata gaaaaattag cggagattta   1500
tgtcaactcc tccttctaca agagacaaa agctgaatta catcaacttt ccggggtga    1560 gaagaagaag aagatcacag tcttcaagga gatcagctac accacctcct ctgtcatca   1620 actcagatgg gtttccaagc gttcattcaa aaacttgctg ggtaatcccc aggcctctat   1680
agctcagatc attgtcacag tcgtactggg actggttata ggtgccattt actttgggct   1740
aaaaaatgat tctactggaa tccagaacag agctggggtt ctcttcttcc tgacgaccaa   1800
ccagtgtttc agcagtgttt cagccgtgga actctttgtg gtagagaaga agctcttcat   1860
acatgaatac atcagcggat actacagagt gtcatcttat ttccttggaa aactgttatc   1920
tgatttatta cccatgagga tgttaccaag tattatattt acctgtatag tgtacttcat   1980
gttaggattg aagccaaagg cagatgcctt cttcgttatg atgtttaccc ttatgatggt   2040
ggcttattca gccagttcca tggcactggc catagcagca ggtcagagtg tggtttctgt   2100
agcaacactt ctcatgacca tctgttttgt gtttatgatg atttttttcag gtctgttggt   2160 caatctcaca accattgcat cttggctgtc atggcttcag tacttcagca ttccacgata   2220
tggatttacg gctttgcagc ataatgaatt tttgggacaa aacttctgcc caggactcaa   2280
tgcaacagga aacaatcctt gtaactatgc aacatgtact ggcgaagaat atttggtaaa   2340
gcagggcatc gatctctcac cctggggctt gtggaagaat cacgtggcct tggcttgtat   2400
gattgttatt ttcctcacaa ttgcctacct gaaattgtta tttcttaaaa aatattctta   2460
aatttcccct taattcagta tgatttatcc tcacataaaa aagaagcact ttgattgaag   2520
tattcaatca agttttttg ttgttttctg ttcccttgcc atcacactgt tgcacagcag   2580 caattgttttt aaagagatac attttttagaa atcacaacaa actgaattaa acatgaaaga   2640
acccaagaca tcatgtatcg catattagtt aatctcctca gacagtaacc atggggaaga   2700
aatctggtct aatttattaa tctaaaaaag gagaattgaa ttctggaaac tcctgacaag   2760
```

```
ttattactgt ctctggcatt tgtttcctca tctttaaaat gaataggtag gttagtagcc    2820
cttcagtctt aatactttat gatgctatgg tttgccatta tttaataaat gacaaatgta    2880
ttaatgctat actggaaatg taaaattgaa aatatgttgg aaaaaagatt ctgtcttata    2940
gggtaaaaaa agccaccgtg atagaaaaaa aatcttttg ataagcacat taaagttaat    3000
agaacttact gatattcctg tctagtggta taatatctca ggaatcttgg ctgagggttt    3060
ggaactgtgg gtagagtaga gggccaggag tccagtaata gaattcttgc accatttctg    3120
gaacattcta gctctgggag gtcacgtaac cttcttgggg tagttcagtg gtttagtggt    3180
ttataatcca ggtgtgcgtc agaatcatct gaggaacttt gctaaaatac aaaaatctgg    3240
cctaagtagc tccagatcta ccttcataaa ggaatctgac cactcctgga tttggtaatt    3300
tccaagttct gaaaattta cttaggattt aataactatt aacatctgtc cctacatagg    3360
ttttctttcc tacttatata ccttatgttc tcttcattct aaccttcatc agtaataggg    3420
aaatgtttta atttatttt tttagttgaa gggtaatgta ccaaaaaata tagttcagtg    3480
aattaaaatg aacacacatg tgcaaccatc aattcaggtc aagaaataga agattgtagc    3540
acacaaaagc ctactcagcc attctcccag tcactacttc cttccttacc cctgggttat    3600
ttttgaaatg acacttgatg tatttccctc tgttgctgtt atgagaacat tgctacagcc    3660
aagtgttgtg tttctgtgtg cataggttga tacttaatta tctccccact tttaataaa    3720 cttttaattt ggaaataatt ttagattgac agaaaagttg caaagatagt gaggaaagtt    3780
cctgtctact ctttgctcag cttccccttaa tgttaacatt ttatatagca agatgcattt    3840
gtcaaagcta acaagttaac attggtacaa tcactgttaa ttaaactgca cacaatattc    3900
agatttcacc acttttccac taatattctt tcattgttct aggattcaat tcaggagacc    3960
acatttcatc tagccctctt ttttaaaagt aaatactttt cagcacttac aggagttaac    4020
tgagctgggg catcatggtg tatagacgcc ctgacactgg tcatcttgga attcatttag    4080
tttgtcagtg ggtgccctga cattctgtca caacatcaat ttgggaacat ggcattatat    4140
ttttatcttt gaactttttt cttttttggat gacatttgat taatgcgtca tcttggaaca    4200
cattatcttt tttcttggtt atgtgatcag gaagattaat cagttttcc tgttcttggt    4260 ataattcctg cttttcacat acctgtccct tacagttctc tatatatacc cttcccttat    4320
tacacagaga gaaatatcta tctatacttt ttacacaaaa tatacttcaa agaaacaaa    4380 acagccacaa ttattaactt tttaaataaa tgagaattta attatatcct aaaaaaaaaa    4440
aaaaa                                                                 4445

<210> SEQ ID NO 20
<211> LENGTH: 655
<212> TYPE: PRT
<213> ORGANISM: Homo sapiens

<400> SEQUENCE: 20

Met Ser Ser Ser Asn Val Glu Val Phe Ile Pro Val Ser Gln Gly Asn
  1               5                  10                  15

Thr Asn Gly Phe Pro Ala Thr Ala Ser Asn Asp Leu Lys Ala Phe Thr
             20                  25                  30

Glu Gly Ala Val Leu Ser Phe His Asn Ile Cys Tyr Arg Val Lys Leu
         35                  40                  45

Lys Ser Gly Phe Leu Pro Cys Arg Lys Pro Val Glu Lys Glu Ile Leu
     50                  55                  60
```

```
Ser Asn Ile Asn Gly Ile Met Lys Pro Gly Leu Asn Ala Ile Leu Gly
 65                  70                  75                  80

Pro Thr Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Gln Asp Asp
            115                 120                 125

Val Val Met Gly Thr Leu Thr Val Arg Glu Asn Leu Gln Phe Ser Ala
            130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
            195                 200                 205

Leu Asp Glu Pro Thr Thr Gly Leu Asp Ser Ser Thr Ala Asn Ala Val
210                 215                 220

Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
            245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
            275                 280                 285

Asn Pro Ala Asp Phe Phe Leu Asp Ile Ile Asn Gly Asp Ser Thr Ala
            290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
            325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
            355                 360                 365

Tyr Thr Thr Ser Phe Cys His Gln Leu Arg Trp Val Ser Lys Arg Ser
            370                 375                 380

Phe Lys Asn Leu Leu Gly Asn Pro Gln Ala Ser Ile Ala Gln Ile Ile
385                 390                 395                 400

Val Thr Val Leu Gly Leu Val Ile Gly Ala Ile Tyr Phe Gly Leu
            405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
            435                 440                 445

Val Val Glu Lys Lys Leu Phe Ile His Glu Tyr Ile Ser Gly Tyr Tyr
            450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
```

-continued

```
                485                     490                     495
Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
        530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
            565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
            595                 600                 605

Thr Gly Glu Glu Tyr Leu Val Lys Gln Gly Ile Asp Leu Ser Pro Trp
            610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655
```